United States Patent
Bakos et al.

(10) Patent No.: US 12,431,230 B2
(45) Date of Patent: Sep. 30, 2025

(54) INTERCONNECTION OF DRUG ADMINISTRATION SYSTEMS

(71) Applicant: JANSSEN PHARMACEUTICALS, INC., Titusville, NJ (US)

(72) Inventors: Gregory J. Bakos, Mason, OH (US); Michael A. Baratta, West Chester, PA (US); Yueheng Dou, Fall River, MA (US); Jason L. Harris, Lebanon, OH (US); Emma Louise Hubert, San Jose, CA (US); Monica A. Kapil, San Jose, CA (US); Peter Krulevitch, Milpitas, CA (US); Wouter Jacques Noel Lequieu, Lievegem (BE); Dolores Perez, Eaton, PA (US); Whitney Phillips, Camas, WA (US); Frederick E. Shelton, Cincinnati, OH (US); Hong Yan, Livermore, CA (US)

(73) Assignee: JANSSEN PHARMACEUTICALS, INC., Titusville, NJ (US)

( * ) Notice: Subject to any disclaimer, the term of this patent is extended or adjusted under 35 U.S.C. 154(b) by 284 days.

(21) Appl. No.: 17/763,085

(22) PCT Filed: Sep. 24, 2020

(86) PCT No.: PCT/IB2020/058966
§ 371 (c)(1),
(2) Date: Mar. 23, 2022

(87) PCT Pub. No.: WO2021/059210
PCT Pub. Date: Apr. 1, 2021

(65) Prior Publication Data
US 2022/0336074 A1    Oct. 20, 2022

Related U.S. Application Data

(60) Provisional application No. 62/905,441, filed on Sep. 25, 2019, provisional application No. 62/905,442, (Continued)

(51) Int. Cl.
*G16H 20/13* (2018.01)
*G16H 20/17* (2018.01)
(Continued)

(52) U.S. Cl.
CPC ............ *G16H 20/13* (2018.01); *G16H 20/17* (2018.01); *H04L 63/0421* (2013.01); *H04W 12/037* (2021.01)

(58) Field of Classification Search
CPC ........ G16H 20/13; G16H 20/17; G16H 20/10; G16H 40/63; G16H 40/40; H04L 63/0421;
(Continued)

(56) References Cited

U.S. PATENT DOCUMENTS

| 2,879,367 A | 3/1959 | McLean |
| 4,946,069 A | 8/1990 | Fuchs |

(Continued)

FOREIGN PATENT DOCUMENTS

| AU | 2012261518 A1 | 12/2012 |
| EP | 2572740 | 3/2013 |

(Continued)

OTHER PUBLICATIONS

"Diet Coke and Mentos Explained," Weebly, dated no later than Mar. 16, 2020, 2 pages (available at <https://dietcoke-and-mentos.weebly.com/>).

(Continued)

*Primary Examiner* — Christopher A Revak
(74) *Attorney, Agent, or Firm* — Craig M. Brown; Johnson &Johnson

(57) ABSTRACT

In general, interconnection of drug administration systems is provided. In an exemplary embodiment, a drug administration device and a remotely located server can establish a unique key for wireless communication between the device and the server. The drug administration device can be configured to sense information relating to at least one of the device and a drug and can be configured to anonymize data indicative of the sensed information using the key stored in (Continued)

memory of the device. The drug administration device can also be configured to use the key in decrypting data received from the server.

25 Claims, 13 Drawing Sheets

Related U.S. Application Data filed on Sep. 25, 2019, provisional application No. 62/905,443, filed on Sep. 25, 2019, provisional application No. 62/905,445, filed on Sep. 25, 2019, provisional application No. 63/020,928, filed on May 6, 2020.

(51) Int. Cl.
 *H04L 9/40* (2022.01)
 *H04W 12/037* (2021.01)

(58) Field of Classification Search
 CPC ......... H04W 12/037; A61M 2005/208; A61M 2205/3553; A61M 2205/505; A61M 2205/52; A61M 5/1723; A61M 5/14244; A61M 5/20; A61M 11/005; A61M 11/041; A61M 15/0066; A61M 15/0085; A61M 15/009; A61M 15/08; A61M 2205/3584
 See application file for complete search history.

(56) References Cited

U.S. PATENT DOCUMENTS

| | | | |
|---|---|---|---|
| 5,363,842 | A | 11/1994 | Mishelevich et al. |
| 5,508,675 | A | 4/1996 | Mahagan |
| 6,321,942 | B1 | 11/2001 | Krampen et al. |
| 7,143,925 | B2 | 12/2006 | Shelton, IV et al. |
| 7,299,949 | B2 | 11/2007 | Greinger-Pert |
| 7,601,118 | B2 | 10/2009 | Smith et al. |
| 7,908,374 | B2 | 3/2011 | Takase et al. |
| 8,317,070 | B2 | 11/2012 | Hueil et al. |
| 8,332,240 | B1 | 12/2012 | Garver et al. |
| 8,393,514 | B2 | 3/2013 | Shelton, IV et al. |
| 8,585,659 | B2 | 11/2013 | Shay |
| 8,696,616 | B2 | 4/2014 | Baynham et al. |
| 9,061,097 | B2 | 6/2015 | Holt et al. |
| 9,129,054 | B2 | 9/2015 | Nawana et al. |
| 9,168,000 | B2 | 10/2015 | Dunki-Jacobs et al. |
| 9,314,808 | B2 | 4/2016 | Allsop |
| 9,427,580 | B2 | 8/2016 | Bork et al. |
| 9,555,950 | B2 | 1/2017 | Le Maner et al. |
| 9,812,831 | B2 | 11/2017 | Zanotto et al. |
| 9,968,737 | B2 | 5/2018 | Pananen et al. |
| 9,980,140 | B1 | 5/2018 | Spencer et al. |
| 10,157,339 | B2 | 12/2018 | Hill et al. |
| 10,398,852 | B2 | 9/2019 | Taylor et al. |
| 10,456,534 | B2 | 10/2019 | Reisacher et al. |
| 10,569,071 | B2 | 2/2020 | Harris et al. |
| 10,716,564 | B2 | 7/2020 | Shelton, IV et al. |
| 10,896,245 | B2 | 1/2021 | Crothall et al. |
| 10,987,468 | B2 | 4/2021 | Mazlish et al. |
| 2002/0014951 | A1 | 2/2002 | Kramer et al. |
| 2002/0038392 | A1 | 3/2002 | De La Huerga |
| 2002/0042596 | A1 | 4/2002 | Hartlaub et al. |
| 2002/0077852 | A1 | 6/2002 | Ford et al. |
| 2002/0091454 | A1 | 7/2002 | Vasko |
| 2003/0135388 | A1 | 7/2003 | Martucci et al. |
| 2004/0158349 | A1 | 8/2004 | Bonney et al. |
| 2005/0027791 | A1 | 2/2005 | Bos et al. |
| 2005/0055244 | A1* | 3/2005 | Mullan .................. G16H 40/63 705/2 |
| 2006/0047538 | A1 | 3/2006 | Condurse et al. |
| 2007/0251835 | A1 | 11/2007 | Mehta et al. |
| 2007/0294432 | A1 | 12/2007 | Takase et al. |
| 2008/0139907 | A1 | 6/2008 | Rao et al. |
| 2008/0154177 | A1 | 6/2008 | Moubayed et al. |
| 2009/0069787 | A1 | 3/2009 | Estes et al. |
| 2009/0163519 | A1 | 6/2009 | Vermeulen et al. |
| 2009/0202387 | A1 | 8/2009 | Moubayed et al. |
| 2009/0204075 | A1* | 8/2009 | Simpson ............... A61M 5/162 604/151 |
| 2011/0230837 | A1 | 9/2011 | Dlugos, Jr. et al. |
| 2011/0275986 | A1 | 11/2011 | Kamen et al. |
| 2011/0295337 | A1 | 12/2011 | Albrecht et al. |
| 2012/0165620 | A1 | 6/2012 | Tanis et al. |
| 2012/0330684 | A1 | 12/2012 | Bashen et al. |
| 2013/0146643 | A1 | 6/2013 | Jacobs et al. |
| 2013/0221065 | A1 | 8/2013 | Schmid et al. |
| 2013/0256377 | A1 | 10/2013 | Aronhalt et al. |
| 2014/0081659 | A1 | 3/2014 | Nawana et al. |
| 2014/0243635 | A1 | 8/2014 | Arefieg |
| 2014/0275748 | A1 | 9/2014 | Schmid et al. |
| 2014/0288511 | A1 | 9/2014 | Tan-Malecki et al. |
| 2015/0129634 | A1 | 5/2015 | Dunki-Jacobs et al. |
| 2015/0133995 | A1 | 5/2015 | Shelton, IV et al. |
| 2015/0133996 | A1 | 5/2015 | Shelton, IV et al. |
| 2015/0134076 | A1 | 5/2015 | Shelton, IV et al. |
| 2015/0134077 | A1 | 5/2015 | Shelton, IV et al. |
| 2015/0248674 | A1* | 9/2015 | Han ......................... G07F 7/00 705/43 |
| 2015/0269355 | A1* | 9/2015 | Tidor ..................... G16H 10/20 705/3 |
| 2015/0272575 | A1 | 10/2015 | Leimbach et al. |
| 2015/0274344 | A1 | 10/2015 | Sullivan et al. |
| 2015/0290390 | A1 | 10/2015 | Ring et al. |
| 2015/0297845 | A1 | 10/2015 | Shahaf et al. |
| 2015/0351758 | A1 | 12/2015 | Shelton, IV et al. |
| 2015/0374919 | A1 | 12/2015 | Gibson |
| 2016/0045674 | A1 | 2/2016 | Blei et al. |
| 2016/0166768 | A1 | 6/2016 | Edwards et al. |
| 2017/0043092 | A1 | 2/2017 | Murakami et al. |
| 2017/0173262 | A1 | 6/2017 | Veltz |
| 2017/0296213 | A1 | 10/2017 | Swensgard et al. |
| 2018/0060527 | A1 | 3/2018 | Kalyanpur et al. |
| 2018/0075202 | A1 | 3/2018 | Davis et al. |
| 2018/0189638 | A1 | 7/2018 | Nurvitadhi et al. |
| 2018/0318526 | A1 | 11/2018 | Yang et al. |
| 2018/0359085 | A1* | 12/2018 | Dervyn .................. G16H 40/67 |
| 2018/0361085 | A1 | 12/2018 | Malhotra et al. |
| 2019/0022306 | A1 | 1/2019 | Gibson et al. |
| 2019/0167908 | A1 | 6/2019 | Fitzgibbon et al. |
| 2019/0180856 | A1 | 6/2019 | Aradottir et al. |
| 2019/0200844 | A1 | 7/2019 | Shelton, IV et al. |
| 2019/0200981 | A1 | 7/2019 | Harris et al. |
| 2019/0201046 | A1 | 7/2019 | Shelton, IV et al. |
| 2019/0201114 | A1 | 7/2019 | Shelton, IV et al. |
| 2019/0201140 | A1 | 7/2019 | Shelton, IV et al. |
| 2019/0206004 | A1 | 7/2019 | Shelton, IV et al. |
| 2019/0206555 | A1 | 7/2019 | Shelton, IV et al. |
| 2019/0207857 | A1 | 7/2019 | Shelton, IV et al. |
| 2019/0272912 | A1 | 9/2019 | Van Orden et al. |
| 2019/0328965 | A1 | 10/2019 | Moberg |
| 2019/0365986 | A1 | 12/2019 | Coiner et al. |
| 2020/0238004 | A1 | 7/2020 | McCullough |
| 2020/0261643 | A1 | 8/2020 | Boyaval et al. |
| 2020/0261657 | A1 | 8/2020 | Gibson et al. |
| 2020/0289740 | A1 | 9/2020 | Tamtoro et al. |
| 2020/0390977 | A1 | 12/2020 | Sanchez |
| 2021/0077713 | A1 | 3/2021 | McCullough et al. |
| 2022/0218900 | A1 | 7/2022 | Gibson et al. |
| 2022/0400377 | A1* | 12/2022 | Alt ............................ G09C 5/00 |
| 2023/0120569 | A1 | 4/2023 | Stonecipher |
| 2023/0372607 | A1 | 11/2023 | Damestani et al. |
| 2024/0157062 | A1* | 5/2024 | Urbanek ............... A61M 5/5086 |

FOREIGN PATENT DOCUMENTS

| | | |
|---|---|---|
| EP | 2918222 | 9/2015 |
| EP | 3734605 A1 * 11/2020 | ......... G06F 21/6245 |
| JP | 2004-348756 A | 12/2004 |
| JP | 2008-21295 A | 1/2008 |
| JP | 2015-210765 A | 11/2015 |

(56) References Cited

FOREIGN PATENT DOCUMENTS

| | | | |
|---|---|---|---|
| JP | 2018-506401 A | 3/2018 | |
| WO | WO 2009/081262 | 7/2009 | |
| WO | 2011053829 A1 | 5/2011 | |
| WO | WO 2011/150032 | 12/2011 | |
| WO | 2014081780 A1 | 5/2014 | |
| WO | WO 2014/152704 | 9/2014 | |
| WO | 2015061386 A1 | 4/2015 | |
| WO | 2015061389 A1 | 4/2015 | |
| WO | 2015119906 A1 | 8/2015 | |
| WO | 2015171777 A1 | 11/2015 | |
| WO | 2015187797 A1 | 12/2015 | |
| WO | 2015187799 A1 | 12/2015 | |
| WO | 2015187802 A1 | 12/2015 | |
| WO | 2015187805 A1 | 12/2015 | |
| WO | WO 2015/187793 | 12/2015 | |
| WO | 2016003813 A1 | 1/2016 | |
| WO | WO 2016/001924 | 1/2016 | |
| WO | 2016061220 A1 | 4/2016 | |
| WO | 2016100055 A1 | 6/2016 | |
| WO | 2016100781 A1 | 6/2016 | |
| WO | 2016/120207 A1 | 8/2016 | |
| WO | WO-2016151364 A1 * | 9/2016 | ........... A61B 5/4842 |
| WO | WO 2016/040512 | 3/2017 | |
| WO | WO 2017/051271 | 3/2017 | |
| WO | WO 2017/089317 | 6/2017 | |
| WO | 2017139741 A1 | 8/2017 | |
| WO | 2017177094 A2 | 10/2017 | |
| WO | 2017200989 A1 | 11/2017 | |
| WO | 2019/096720 A1 | 5/2019 | |
| WO | WO 2019/099568 | 5/2019 | |
| WO | WO-2023091743 A1 * | 5/2023 | ........... A61B 5/0022 |

OTHER PUBLICATIONS

"Dual Component Epoxy Cartridges K-Series Syringe," Adhesive Dispensing Ltd., dated no later than Mar. 21, 2020, 2 pages (available at <https://www.adhesivedispensing.net/Dual_Component_K_Series_Dispensing_s/236.htm>).

"Molecular Sieve vs Silica Gel: What's the Difference?", Multisorb Fixation Group, dated no later than Mar. 24, 2020, 2 pages (available at <https://www.multisorb.com/blog/pharmaceuticals/molecular-sieve-vs-silica-gel-whats-the-difference/>).

"Orbeez® Toys—Add Water to Make Them Grow!", Maya Toys, dated no later than Mar. 24, 2020, 2 pages (available at <https://mayatoys.net/pages/orbeez>).

"Philips Medication Dispenser," Philips Lifeline, dated no later than Mar. 17, 2020, 6 pages (available at <https://www.lifeline.philips.com/pill-dispenser/health-mdp.html>).

"Study Shows High Altitude and Medication May Not Mix, " healthNEWS, University of Cincinnati Academic Health Center, Jan. 14, 1999, 1 page (available at <http://healthnews.uc.edu/news/?/153/>).

"The Companion Dual Chamber Reconstitution Syringe," Credence MedSystems, Inc, dated no later than Mar. 18, 2020, 3 pages <available at <https://www.credencemed.com/dual-chamber/>).

"VapourSoft® Technology," Bespak Europe Ltd., dated no later than Mar. 16, 2020, 2 pages (available at <https://bespak.com/products/injection-devices/vapoursoft-technology/>).

International Search Report and Written Opinion for PCT Application No. PCT/IB2020/058966 mailed Dec. 10, 2020 (16 pages).

Jae Hung Park et al., "Biodegradable Polymers for Microencapsulation of Drugs," Molecules 2005, 10, p. 146-161.

Man Chiu Fung, "Experimental and numerical study of spray characteristics of nasal spray devices," School of Aerospace, Mechanical and Manufacturing Engineering Science, Engineering and Technology Portfolio, RMIT University, Aug. 2013 (179 pages).

Rafi, "14 List of Chemicals That Glow Under Black Light—Application," Jan. 24, 2018, 3 pages (available at <https://azchemistry.com/list-of-chemicals-that-glow-under-black-light>).

Japanese Patent Office "Decision of Rejection" for corresponding Japanese Patent Application Serial No. 2022518969, dated Dec. 10, 2024, with English language translation, 8 pp.

* cited by examiner

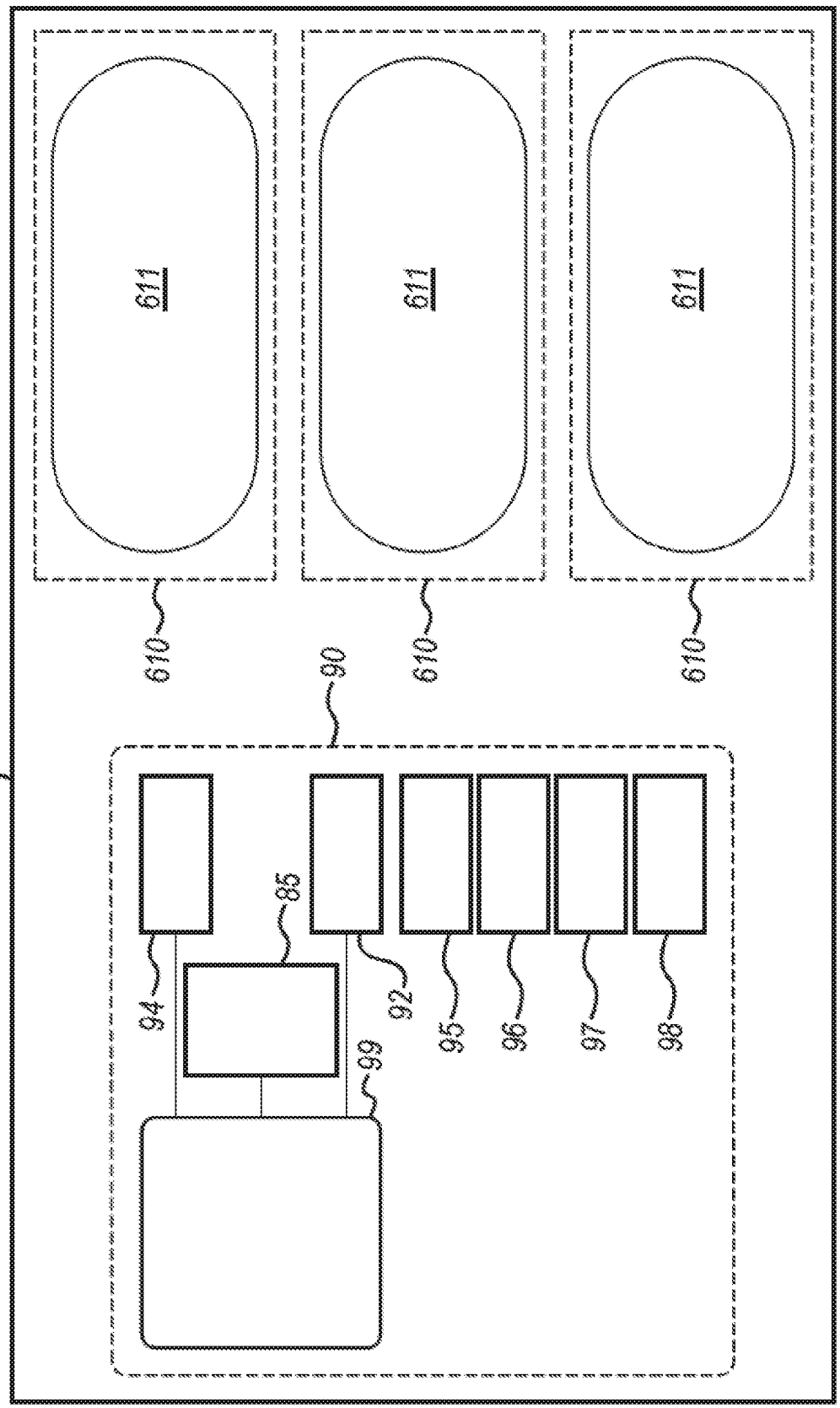

INTERCONNECTION OF DRUG ADMINISTRATION SYSTEMS

CROSS REFERENCE TO RELATED APPLICATIONS

This application is the U.S. national stage of PCT Application No. PCT/IB2020/058966, filed Sep. 24, 2020, which claims priority to U.S. Provisional Patent Application Nos. 62/905,441, filed Sep. 25, 2019; 62/905,442, filed Sep. 25, 2019; 62/905,443, filed Sep. 25, 2019; 62/905,445, filed Sep. 25, 2019; and 63/020,928, filed May 6, 2020, the entire contents of each of which are hereby incorporated by reference in their entirety.

FIELD

The embodiments described herein relate to a device for administering and/or provision of a drug. The present disclosure further relates to a system in which the device can be used, and a method of administration, and a further method associated with the system.

BACKGROUND

Pharmaceutical products (including large and small molecule pharmaceuticals, hereinafter "drugs") are administered to patients in a variety of different ways for the treatment of specific medical indications. Regardless of the manner of the administration, care must be taken when administering drugs to avoid adverse effects on the patient. For example, care must be taken not to administer more than a safe amount of the drug to the patient. This requires consideration of the amount of dose given and the time frame over which the dose is delivered, sometimes in relation to previous doses, or doses of other drugs. Moreover, care must be taken not to inadvertently administer an incorrect drug to the patient, or drugs that have degraded due to their age or storage conditions. All of these considerations can be conveyed in guidance associated with the specific drugs or drug combinations. However, this guidance is not always followed correctly, for example due to mistakes, such as human error. This can lead to adverse effects on the patient or result in inappropriate drug administration, for example insufficient or excessive volume of drug being administered for the specific medical indication.

In relation to how a drug is administered to the patient, there are various dosage forms that can be used. For example, these dosage forms may include parenteral, inhalational, oral, ophthalmic, nasal, topical, and suppository forms of one or more drugs.

The dosage forms can be administered directly to the patient via a drug administration device. There are a number of different types of drug administration devices commonly available for delivery of the various dosage forms including: syringes, injection devices (e.g., autoinjectors, jet injectors, and infusion pumps), nasal spray devices, and inhalers.

It can be desirable to monitor compliance with the guidance that is associated with the drugs that are administered to a patient in various dosage forms. This can provide assurance that correct procedures are being followed and avoid the adoption of incorrect and potentially dangerous approaches. Further, this can also enable optimization of the administration of the drug to the patient.

Additionally, data associated with a patient's medical history, current medical condition, and/or therapeutic treatments, such as use of a drug administration device, can include private, sensitive information that is usually only shared between a patient and an appropriate medical professional. Data encryption allows data to be shared between users and computer systems in a secure, anonymized manner. Data encryption can be performed using a key-based cryptographic system to ensure that data, such as private medical data, can be shared without risk of exposing the nature or contents of the data to unintended users. Key-based cryptographic systems enable secure data transmission using a public key/private key architecture such that anyone can encrypt data using a public key, but the encrypted data can only be decrypted with the recipient's private key. However, it can be difficult for a patient-controlled device to be properly set up for effective communication due to any number of factors, such as patient unfamiliarity with the device and the need for medical-related information to be communicated in a timely fashion to avoid harm to the patient.

Patients typically administer drugs according to the guidance but often do so without any sort of notification or feedback about the administration of the drug. As such, a patient may forget to or may incorrectly administer a drug based on that patient's interpretation of the guidance and/or may do so without any awareness of their own physiological conditions. Incorrectly administering a drug or failing to follow the medical professional's guidance can have serious, even life-threatening, consequences for the patient.

Patients who do administer a drug may experience negative side effects or adverse clinical outcomes associated with administering the drug and must usually initiate communication with the appropriate medical professional who prescribed the drug in order to discuss alternate drugs, drug administration devices, and/or guidance which may alleviate the side effects or adverse conditions the patient is experiencing. The patient may delay providing feedback to an appropriate medical professional which can worsen the negative conditions the patient may be experiencing, may inadvertently not report relevant information, and/or may contribute additional delays to adjust or reconfigure the patient's drug administration device with new drug dosage or delivery schedule settings that may alleviate the issues the patient is experiencing.

Further, the large number of patients with a given condition represent a potentially useful resource for accumulating data on physiological responses. However, it is difficult to collect all of this data so possible trends and correlations can be missed.

SUMMARY

In one aspect, a drug administration device configured to retain a drug therein is provided that in one embodiment includes a sensor configured to sense information relating to at least one of the drug administration device and the drug. The drug administration device also includes a memory configured to store data therein. The stored data includes a key established with a remotely located server. The key is unique to the drug administration device and to the remotely located server. The drug administration device also includes a communications interface configured to wirelessly transmit data indicative of the sensed information to a remotely located communications interface. The drug administration device also includes a processor configured to use the key to anonymize the data indicative of the sensed information prior to the transmission of the data indicative of the sensed information.

The drug administration device can have any number of variations. For example, the drug administration device can include one of a syringe, an injector, an inhaler, a nasal spray device, and an infusion pump. For another example, the processor can be configured to use the key in anonymizing all data transmitted from the communications interface to the remotely located communications interface. For yet another example, the processor can be configured to repeatedly use the key to anonymize multiple sets of data indicative of information sensed by the sensor.

For still another example, the communications interface can be configured to wirelessly receive data from the remotely located communications interface, and the processor can be configured to use the key in decrypting the data received from the remotely located communications interface. In at least some embodiments, the processor can be configured to use the key in decrypting all data received from the remotely located communications interface.

For another example, the communications interface can be configured to wirelessly receive data from the remotely located communications interface, the data can include information regarding proper disposal of the drug delivery device after the drug has been delivered from the drug delivery device. In at least some embodiments, the processor can be configured to cause a notification of the information regarding proper disposal information to be provided to a user of the drug administration device.

For still another example, the drug delivery device can include a label including information regarding proper disposal of the drug delivery device after the drug has been delivered from the drug delivery device.

For yet another example, the processor can be configured to control delivery of the drug from the drug administration mechanism based at least in part on the sensed information. For yet another example, the drug can include at least one of infliximab, golimumab, ustekinumab, daratumumab, guselkumab, epoetin alfa, risperidone, esketamine, ketamine, and paliperidone palmitate.

In another embodiment, a drug administration device includes a memory configured to store therein an algorithm including at least one variable parameter, a communications interface configured to wirelessly receive data from a remotely located communications interface, and a processor configured to use the algorithm in controlling delivery of a drug from the drug administration device to a patient. The processor is also configured to change the at least one variable parameter of the algorithm stored in the memory based on the data received from the remotely located communications interface.

The drug administration device can have any number of variations. For example, the drug administration device can include one of a syringe, an injector, an inhaler, a nasal spray device, and an infusion pump. For another example, the drug administration device can include a drug holder configured to retain the drug therein, and controlling delivery of the drug from the drug administration device to the patient can include controlling release of the drug from the drug holder. For yet another example, the drug administration device can be an autoinjector configured to automatically advance a needle into a patient, the at least one variable parameter can include a rate at which the needle is to be automatically advanced into the patient, the data received from the remotely located communications interface can include another rate at which the needle is to be automatically advanced into the patient, and changing the at least one variable parameter can include replacing the rate with the updated rate in the algorithm. For another example, the at least one variable parameter can include at least one of a rate of delivery of the drug from the drug administration device to the patient, a timing between doses of the drug being delivered from the drug administration device to the patient, and a temperature of the drug. For still another example, the data received from the remotely located communications interface can be based on a physician requested change to the algorithm input at a remotely located computer system.

For another example, the processor can also be configured to cause a request to be transmitted from the communications interface to the remotely located communications interface, the request can request an update of the algorithm, and the data received from the remotely located communication interface can be in response to the request. In at least some embodiments, the communications interface can receive a response to the request from the remotely located communications interface that indicates no update to the algorithm is needed, and the processor does not change the at least one variable parameter of the algorithm stored in the memory.

For still another example, the processor can be configured to, after using the algorithm in controlling delivery of the drug from the drug administration device, use the algorithm in controlling another delivery of the drug from the drug administration device to the patient.

For another example, the drug administration device can include a sensor configured to sense information relating to at least one of the drug administration device and the drug. In at least some embodiments, the communications interface can be configured to transmit data indicative of the sensed information to the remotely located communications interface, and the data received from the remotely located communications interface can be based at least in part on the data indicative of the sensed information. In at least some embodiments, the processor can also be configured to change the at least one variable parameter of the algorithm stored in the memory based on the sensed information without first transmitting data indicative of the sensed information to the remotely located communications interface.

For yet another example, the data received from the remotely located communications interface can be automatically transmitted to the communications interface without being in response to a request from the communications interface for an update of the algorithm.

For still another example, the communications interface can also be configured to wirelessly receive algorithm data from the remotely located communications interface, and the processor can also be configured to change the algorithm stored in the memory based on the data received from the remotely located communications interface. In at least some embodiments, changing the algorithm can include adding at least one additional variable parameter to the algorithm.

For another example, the drug can include at least one of infliximab, golimumab, ustekinumab, daratumumab, guselkumab, epoetin alfa, risperidone, esketamine, ketamine, and paliperidone palmitate.

In another embodiment, a drug administration device includes a memory configured to store an algorithm, a communications interface configured to wirelessly receive data from a remotely located communications interface, a drug holder configured to retain a drug therein, and a processor configured to control delivery of a dose of the drug from the drug holder to a patient by executing the algorithm. The processor is configured to adjust the algorithm stored in the memory based on the data received from the remotely located communications interface, and to control delivery of a subsequent dose of the drug holder to the patient by executing the adjusted algorithm.

The drug administration device can have any number of variations. For example, the drug administration device can include one of a syringe, an injector, an inhaler, a nasal spray device, and an infusion pump. For another example, the algorithm can include at least one variable parameter, and the processor adjusting the algorithm can include changing the at least one variable parameter of the algorithm. For yet another example, adjusting the algorithm can include adding at least one variable parameter to the algorithm. For another example, the drug can include at least one of infliximab, golimumab, ustekinumab, daratumumab, guselkumab, epoetin alfa, risperidone, esketamine, ketamine, and paliperidone palmitate.

In one embodiment, a drug administration device includes a drug holder configured to retain a drug therein, a display, and a processor. The processor is configured to cause the display to show at least one of a reminder of a current need to manually administer a dose of the drug to the patient from the drug holder, a summary of previously scheduled doses of the drug to the patient from the drug holder, and an indication of correlation between a timing of previously delivered doses of the drug to the patient from the drug holder and a timing of at least one medical event experienced by the patient.

The drug administration device can have any number of variations. For example, the drug administration device can include one of a syringe, an injector, an inhaler, a nasal spray device, and an infusion pump. For another example, the processor of the device can be configured to cause the display to show at least the reminder. For yet another example, the processor of the device can be configured to cause the display to show at least the summary, and the summary can include at least one of an indication of any missed doses among the previously scheduled doses, an indication of any successfully delivered doses among the previously scheduled doses, an indication of timing of the previously delivered doses compared to a predetermined delivery schedule for the doses, an indication of the drug's intended treatment effect on the patient, and an indication of an estimated remaining duration of the drug's effect on the patient. For still another example, the processor can be configured to cause the display to show at least the indication of correlation.

For another example, the device can include a communications interface configured to wirelessly receive data from a remotely located communications interface, and the processor can be configured to cause the display to show information indicative of the data received from the remotely located communications interface. In at least some embodiments, the data received from the remotely located communications interface can include medical history information of the patient. In at least some embodiments, the data received from the remotely located communications interface can include help information regarding correct use of the drug administration device, and the processor can also be configured to cause the display to show information indicative of the help information.

For yet another example, the device can include a sensor configured to sense information relating to at least one of the drug administration device and the drug, and the processor can be configured to cause the display to show information indicative of the sensed information. In at least some embodiments, the device can include a communications interface configured to wirelessly transmit data indicative of the sensed information to a remotely located communications interface and to subsequently wirelessly receive data from the remotely located communications interface based at least in part on the transmitted data, and the processor can be configured to cause the display to show information indicative of the data received from the remotely located communications interface. For another example, the drug can include at least one of infliximab, golimumab, ustekinumab, daratumumab, guselkumab, epoetin alfa, risperidone, esketamine, ketamine, and paliperidone palmitate.

In another aspect, a drug administration system is provided that in one embodiment includes a server including a communication interface configured to wirelessly receive data and wirelessly transmit data, a memory configured to store a key therein, and a processor. The system also includes a drug administration device including a memory configured to store the key therein. The key is unique to the drug administration device and the server. The drug administration device includes a communications interface configured to wirelessly transmit data to the communication interface of the server and to wirelessly receive data from the communications interface of the server. The drug administration device also includes a processor configured to use the key to anonymize all data transmitted to the communications interface of the server prior to the transmission thereof. The processor of the server is configured to use the key to anonymize all data transmitted to the communications interface of the drug administration device prior to the transmission thereof.

The system can vary in any number of ways. For example, the data transmitted to communications interface of the server can include data in response to a data request received from the server. For still another example, the drug administration device can include one of a syringe, an injector, an inhaler, a nasal spray device, and an infusion pump.

For another example, the drug administration device can also include a sensor configured to sense information relating to at least one of the drug administration device and the drug, and the data transmitted to the communications interface of the server can include data indicative of the sensed information. In at least some embodiments, the processor of the drug administration device can be configured to control delivery of the drug from the drug administration device to a patient based at least in part on the sensed information.

For another example, the processor of the server can be configured to use the key to decrypt all data received from the communications interface of the drug administration device, and the processor of the drug administration device can be configured to use the key to decrypt all data received from the communications interface of the server. For yet another example, the processor of the server can be configured to automatically cause the data received from the communications interface of the drug administration device to be uploaded into at least one of an Electronic Health Record (EHR) of a patient associated with the drug administration device and a patient monitoring form for the drug's Risk Evaluation and Mitigation Strategies (REMS). For another example, the drug can include at least one of infliximab, golimumab, ustekinumab, daratumumab, guselkumab, epoetin alfa, risperidone, esketamine, ketamine, and paliperidone palmitate.

In another embodiment, a drug administration system includes a drug administration device configured to retain a drug therein for delivery to a patient, a display, a communications interface configured to wirelessly receive data indicative of medical information regarding the patient, and a processor. The processor is configured to cause the display to show at least one of a reminder of a current need to manually administer a dose of a drug to a patient from a drug administration device configured to retain a drug therein, a summary of previously scheduled doses of the drug to the patient from the drug administration device, and an indication of correlation between a timing of previously delivered doses of the drug to the patient from the drug administration device and a timing of at least one medical event experienced by the patient.

The drug administration system can have any number of variations. For example, the drug administration device can include one of a syringe, an injector, an inhaler, a nasal spray device, and an infusion pump. For another example, the system can include a communications interface configured to wirelessly receive data from a remotely located communications interface, and the processor can be configured to cause the display to show information indicative of the data received from the remotely located communications interface.

For yet another example, the system can include a sensor configured to sense information relating to at least one of the drug administration device and the drug, and the processor can be configured to cause the display to show information indicative of the sensed information. In at least some embodiments, the system can include a communications interface configured to wirelessly transmit data indicative of the sensed information to a remotely located communications interface and to subsequently wirelessly receive data from the remotely located communications interface based at least in part on the transmitted data, and the processor can be configured to cause the display to show information indicative of the data received from the remotely located communications interface. In at least some embodiments, the drug administration device of the system can include the communications interface.

For still another example, the drug administration device can include the display and the processor. For yet another example, a server can include the display and the processor. For another example, a mobile device can include the display and the processor. For yet another example, the drug can include at least one of infliximab, golimumab, ustekinumab, daratumumab, guselkumab, epoetin alfa, risperidone, esketamine, ketamine, and paliperidone palmitate.

In another aspect, a drug administration method is provided that in one embodiment includes establishing a unique key for wireless communications between a drug administration device and a server located remotely from the drug administration device. The key is stored in a memory of the drug administration device and in a memory of the server. The method also includes sensing, with a sensor of the drug administration device, information relating to at least one of the drug administration device and the drug. The method also includes anonymizing, with a processor of the drug administration device, data indicative of the sensed information using the key stored in the memory of the drug administration device. The method also includes using the key stored in the memory of the drug administration device in decrypting, with the processor of the drug administration device, data received from the server.

The method can have any number of variations. For example, the method can further include controlling, with the processor of the drug administration device, delivery of the drug from the drug administration device based at least in part on the sensed information. For another example, the drug administration device can include one of a syringe, an injector, an inhaler, a nasal spray device, and an infusion pump. For another example, the drug can include at least one of infliximab, golimumab, ustekinumab, daratumumab, guselkumab, epoetin alfa, risperidone, esketamine, ketamine, and paliperidone palmitate.

For yet another example, the data can include information regarding proper disposal of the drug delivery device after the drug has been delivered from the drug delivery device. In at least some embodiments, the method can include causing, using the processor, a notification of the information regarding proper disposal information to be provided to a user of the drug administration device.

In another embodiment, a drug administration method includes executing, using a processor of a drug administration device, an algorithm to control delivery of a dose of a drug from the drug administration device to a patient. The algorithm is stored in a memory of the drug administration device. The method also includes wirelessly receiving at a communications interface of the drug administration device data from a communications interface located remotely from the drug administration device. The method also includes changing, using the processor, at least one variable parameter of the algorithm stored in the memory based on the data received from the remotely located communications interface. The method also includes executing, using the processor, the changed algorithm to control delivery of another dose of the drug from the drug administration device to the patient.

The method can have any number of variations. For example, the drug can include at least one of infliximab, golimumab, ustekinumab, daratumumab, guselkumab, epoetin alfa, risperidone, esketamine, ketamine, and paliperidone palmitate.

In another aspect, a sensor configured to sense information relating to a physiological parameter of a patient is provided and in one embodiment includes a memory configured to store data therein, the stored data including a key established with a remotely located server and that is unique to the sensor and the remotely located server; a communications interface configured to wirelessly transmit data indicative of the sensed information to a remotely located communications interface; and a processor configured to use the key to anonymize the data indicative of the sensed information prior to the transmission of the data indicative of the sensed information.

The sensor can have any number of variations. For example, the processor can be configured to use the key in anonymizing all data transmitted from the communications interface to the remotely located communications interface. For another example, the processor can be configured to repeatedly use the key to anonymize multiple sets of data indicative of information sensed by the sensor. In at least some embodiments, the sensor can be configured to obtain information relating to the physiological parameter of the patient at least once every 24 hours.

For yet another example, the communications interface of the sensor can be configured to wirelessly receive data from the remotely located communications interface, and the processor can be configured to use the key in decrypting the data received from the remotely located communications interface. In at least some embodiments, the processor can be configured to use the key in decrypting all data received from the remotely located communications interface.

For still another example, the physiological parameter measured by the sensor can be at least one of blood glucose level, blood oxygen level, body weight, blood pressure, heart rate, and sleep duration. For yet another example, the drug can include at least one of infliximab, golimumab, ustekinumab, daratumumab, guselkumab, epoetin alfa, risperidone, esketamine, ketamine, and paliperidone palmitate.

For another example, a sensor system can include the sensor and can include a server including a communications interface configured to wirelessly receive data, a memory configured to store a key therein, and a processor.

The sensor system can have any number of variations. For example, the processor of the server can be configured to use the key to anonymize all data transmitted to the communications interface of the sensor prior to the transmission thereof. In at least some embodiments, the processor of the server can be configured to use the key to decrypt all data received from the communications interface of the sensor, and the processor of the sensor can be configured to use the key to decrypt all data received from the communications interface of the server. The data transmitted to the communications interface of the server can include data in response to a data request received from the server.

For another example, the sensor system can further include a plurality of sensors, and the sensor can be one of the plurality of sensors. In at least some embodiments, the plurality of sensors can include sensors configured to measure different physiological parameters of the same patient. The plurality of sensors can further include sensors configured to measure corresponding physiological parameters on a plurality of patients. The server can be configured to store the data indicative of the sensed information along with an indication of the physiological parameter and the patient. The server can be configured to receive and store data indicative of information relating to a drug administration device associated with each patient. The server can be configured to receive and store data indicative of the nutritional intake of each patient. For yet another example, the drug can include at least one of infliximab, golimumab, ustekinumab, daratumumab, guselkumab, epoetin alfa, risperidone, esketamine, ketamine, and paliperidone palmitate.

In another aspect, a method of sensing information relating to a physiological parameter of a patient is provided that in one embodiment includes establishing a unique key for wireless communications between a sensor and a server located remotely from the sensor, the key being stored in a memory of the sensor and in a memory of the server; sensing, with the sensor, the information relating to a physiological parameter of a patient; anonymizing, with a processor of the sensor, data indicative of the sensed information using the key stored in the memory of the sensor; and using the key stored in the memory of the sensor in decrypting, with the processor of the sensor, data received from the server.

The method can have any number of variations. For example, the drug can include at least one of infliximab, golimumab, ustekinumab, daratumumab, guselkumab, epoetin alfa, risperidone, esketamine, ketamine, and paliperidone palmitate.

BRIEF DESCRIPTION OF DRAWINGS

The present invention is described by way of reference to the accompanying figures which are as follows:

FIG. 6 is a schematic view of a housing for a dosage form;

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Examples of various types of drug administration devices, namely: an autoinjector 100, an infusion pump 200, an inhaler 300, and a nasal spray device 400, are described below with reference to the hereinbefore referenced figures.

Autoinjector

Figure 1:
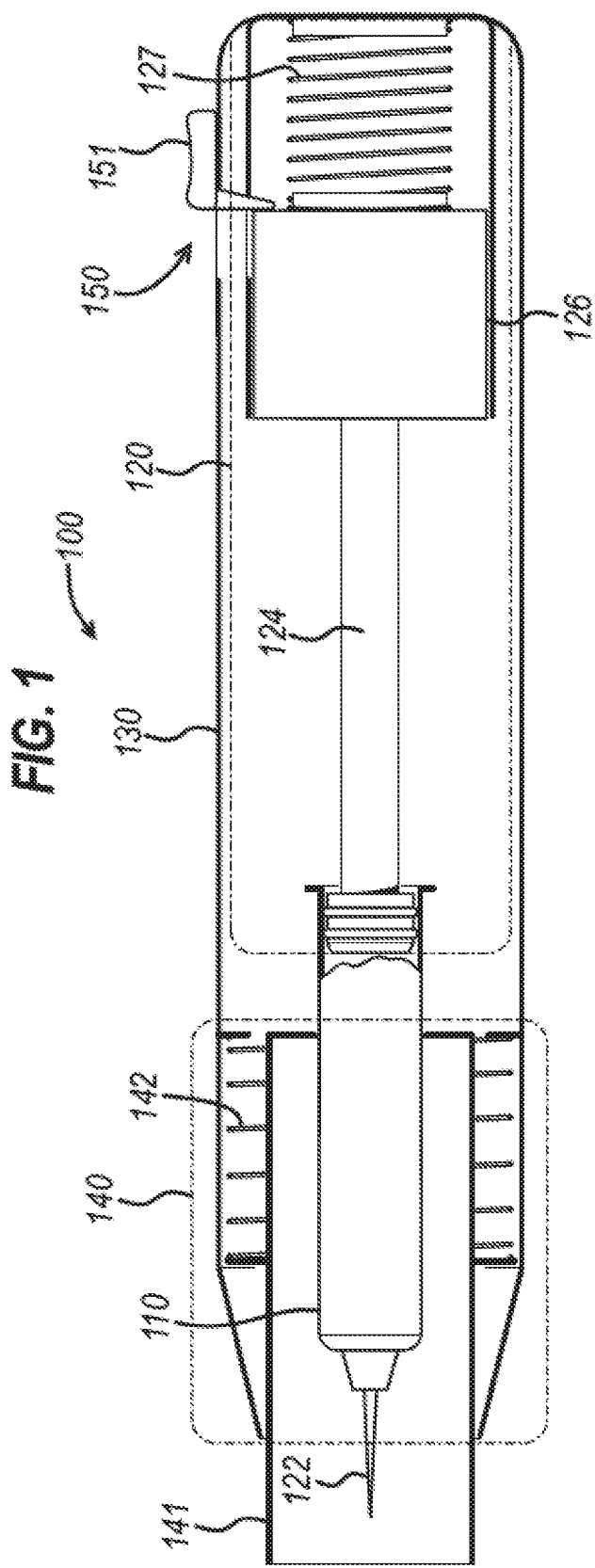
FIG. 1 is a schematic view of a first type of drug administration device, namely an autoinjector.

FIG. 1 is a schematic exemplary view of a first type of drug delivery device, namely an injection device, in this example an autoinjector 100, useable with embodiments described herein. The autoinjector 100 comprises a drug holder 110 which retains a drug to be dispensed and a dispensing mechanism 120 which is configured to dispense a drug from the drug holder 110 so that it can be administered to a patient. The drug holder 110 is typically in the form of a container which contains the drug, for example it may be provided in the form of a syringe or a vial, or be any other suitable container which can hold the drug. The autoinjector 100 comprises a discharge nozzle 122, for example a needle of a syringe, which is provided at a distal end of the drug holder 110. The dispensing mechanism 120 comprises a drive element 124, which itself may also comprise a piston and/or a piston rod, and drive mechanism 126. The dispensing mechanism 120 is located proximal to the end of the drug holder 110 and towards the proximal end of the autoinjector 100.

The autoinjector 100 comprises a housing 130 which contains the drug holder 110, drive element 124 and drive mechanism 126 within the body of the housing 130, as well as containing the discharge nozzle 122, which, prior to injection, would typically be contained fully within the housing, but which would extend out of the housing 130 during an injection sequence to deliver the drug. The dispensing mechanism 120 is arranged so that the drive element 124 is advanced through the drug holder 110 in order to dispense the drug through the discharge nozzle 122, thereby allowing the autoinjector to administer a drug retained in drug holder 110 to a patient. In some instances, a user may advance the drive element 124 through the drug holder 110 manually. In other instances, the drive mechanism 126 may include a stored energy source 127 which advances the drive element 124 without user assistance. The stored energy source 127 may include a resilient biasing member such as a spring, or a pressurized gas, or electronically powered motor and/or gearbox.

The autoinjector 100 includes a dispensing mechanism protection mechanism 140. The dispensing mechanism protection mechanism 140 typically has two functions. Firstly, the dispensing mechanism protection mechanism 140 can function to prevent access to the discharge nozzle 122 prior to and after injection. Secondly, the autoinjector 100 can function, such that when put into an activated state, e.g., the dispensing mechanism protection mechanism 140 is moved to an unlocked position, the dispensing mechanism 120 can be activated.

The protection mechanism 140 covers at least a part of the discharge nozzle 122 when the drug holder 110 is in its retracted position proximally within the housing 130. This is to impede contact between the discharge nozzle 122 and a user. Alternatively, or in addition, the protection mechanism 140 is itself configured to retract proximally to expose the discharge nozzle 122 so that it can be brought into contact with a patient. The protection mechanism 140 comprises a shield member 141 and return spring 142. Return spring 142 acts to extend the shield member 141 from the housing 130, thereby covering the discharge nozzle 122 when no force is applied to the distal end of the protection mechanism 140. If a user applies a force to the shield member 141 against the action of the return spring 142 to overcome the bias of the return spring 142, the shield member 141 retracts within the housing 130, thereby exposing the discharge nozzle 122. The protection mechanism 140 may alternatively, or in addition, comprise an extension mechanism (not shown) for extending the discharge nozzle 122 beyond the housing 130, and may further comprise a retracting mechanism (not shown) for retracting the discharge nozzle 122 within the housing 130. The protection mechanism 140 may alternatively, or in addition, comprise a housing cap and/or discharge nozzle boot, which can be attached to the autoinjector 100. Removal of the housing cap would typically also remove the discharge nozzle boot from the discharge nozzle 122.

The autoinjector 100 also includes a trigger 150. The trigger 150 comprises a trigger button 151 which is located on an external surface of the housing 130 so that it is accessible by a user of the autoinjector 100. When the trigger 150 is pressed by a user, it acts to release the drive mechanism 126 so that, via the drive element 124, the drug is then driven out of the drug holder 110 via the discharge nozzle 122.

The trigger 150 may also cooperate with the shield member 141 in such a way that the trigger 150 is prevented from being activated until the shield member 141 has been retracted proximally sufficiently into the housing 130 into an unlocked position, for example by pushing a distal end of the shield member 141 against the skin of a patient. When this has been done, the trigger 150 becomes unlocked, and the autoinjector 100 is activated such that the trigger 150 can be depressed and the injection and/or drug delivery sequence is then initiated. Alternatively, retraction of the shield member 141 alone in a proximal direction into the housing 130 can act to activate the drive mechanism 126 and initiate the injection and/or drug delivery sequence. In this way, the autoinjector 100 has device operation prevention mechanism which prevents dispensing of the drug by, for example, preventing accidental release of the dispensing mechanism 120 and/or accidental actuation of the trigger 150.

While the foregoing description relates to one example of an autoinjector, this example is presented purely for illustration, the present invention is not limited solely to such an autoinjector. A person skilled in the art understands that various modifications to the described autoinjector may be implemented within the scope of the present disclosure.

Autoinjectors of the present disclosure can be used to administer any of a variety of drugs, such as any of epinephrine, Rebif, Enbrel, Aranesp, atropine, pralidoxime chloride, and diazepam.

Infusion Pump

In other circumstances, patients can require precise, continuous delivery of medication or medication delivery on a regular or frequent basis at set periodic intervals. Infusion pumps can provide such controlled drug infusion, by facilitating the administering of the drug at a precise rate that keeps the drug concentration within a therapeutic margin, without requiring frequent attention by a healthcare professional or the patient.

Figure 2:
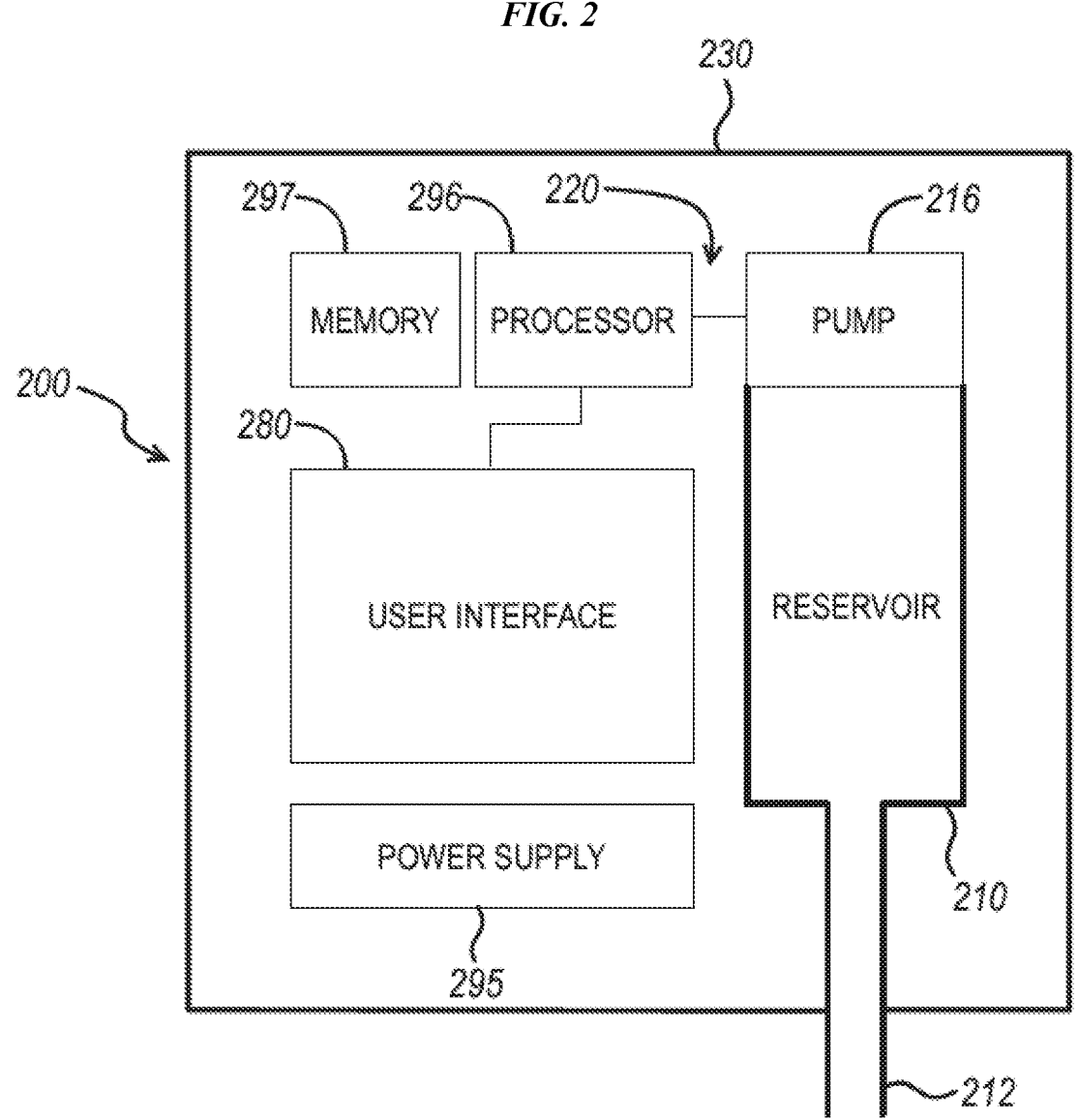
FIG. 2 is a schematic view of a second type of drug administration device, namely an infusion pump.

FIG. 2 is a schematic exemplary view of a second type of drug delivery device, namely an infusion pump 200, useable with the embodiments described herein. The infusion pump 200 comprises a drug holder 210 in the form of a reservoir for containing a drug to be delivered, and a dispensing mechanism 220 comprising a pump 216 adapted to dispense a drug contained in the reservoir, so that the drug can be delivered to a patient. These components of the infusion pump are located within housing 230. The dispensing mechanism 220 further comprises an infusion line 212. The drug is delivered from the reservoir upon actuation of the pump 216 via the infusion line 212, which may take the form of a cannula. The pump 216 may take the form of an elastomeric pump, a peristaltic pump, an osmotic pump, or a motor-controlled piston in a syringe. Typically, the drug is delivered intravenously, although subcutaneous, arterial and epidural infusions may also be used.

Infusion pumps of the present disclosure can be used to administer any of a variety of drugs, such as any of insulin, antropine sulfate, avibactam sodium, bendamustine hydrochloride, carboplatin, daptomycin, epinephrine, levetiracetam, oxaliplatin, paclitaxel, pantoprazole sodium, treprostinil, vasopressin, voriconazole, and zoledronic acid.

The infusion pump 200 further comprises control circuitry, for example a processor 296 in addition to a memory 297 and a user interface 280, which together provide a triggering mechanism and/or dosage selector for the pump 200. The user interface 280 may be implemented by a display screen located on the housing 230 of the infusion pump 200. The control circuitry and user interface 280 can be located within the housing 230, or external thereto and communicate via a wired or wireless interface with the pump 216 to control its operation.

Actuation of the pump 216 is controlled by the processor 296 which is in communication with the pump 216 for controlling the pump's operation. The processor 296 may be programmed by a user (e.g., patient or healthcare professional), via a user interface 280. This enables the infusion pump 200 to deliver the drug to a patient in a controlled manner. The user can enter parameters, such as infusion duration and delivery rate. The delivery rate may be set by the user to a constant infusion rate or as set intervals for periodic delivery, typically within pre-programmed limits. The programmed parameters for controlling the pump 216 are stored in and retrieved from the memory 297 which is in communication with the processor 296. The user interface 280 may take the form of a touch screen or a keypad.

A power supply 295 provides power to the pump 216, and may take the form of an energy source which is integral to the pump 216 and/or a mechanism for connecting the pump 216 to an external source of power.

The infusion pump 200 may take on a variety of different physical forms depending on its designated use. It may be a stationary, non-portable device, e.g., for use at a patient's bedside, or it may be an ambulatory infusion pump which is designed to be portable or wearable. An integral power supply 295 is particularly beneficial for ambulatory infusion pumps.

While the foregoing description relates to one example of an infusion pump, this example is provided purely for illustration. The present disclosure is not limited to such an infusion pump. A person skilled in the art understands that various modifications to the described infusion pump may be implemented within the scope of the present disclosure. For example, the processor may be pre-programmed, such that it is not necessary for the infusion pump to include a user interface.

Inhaler

Figure 3:
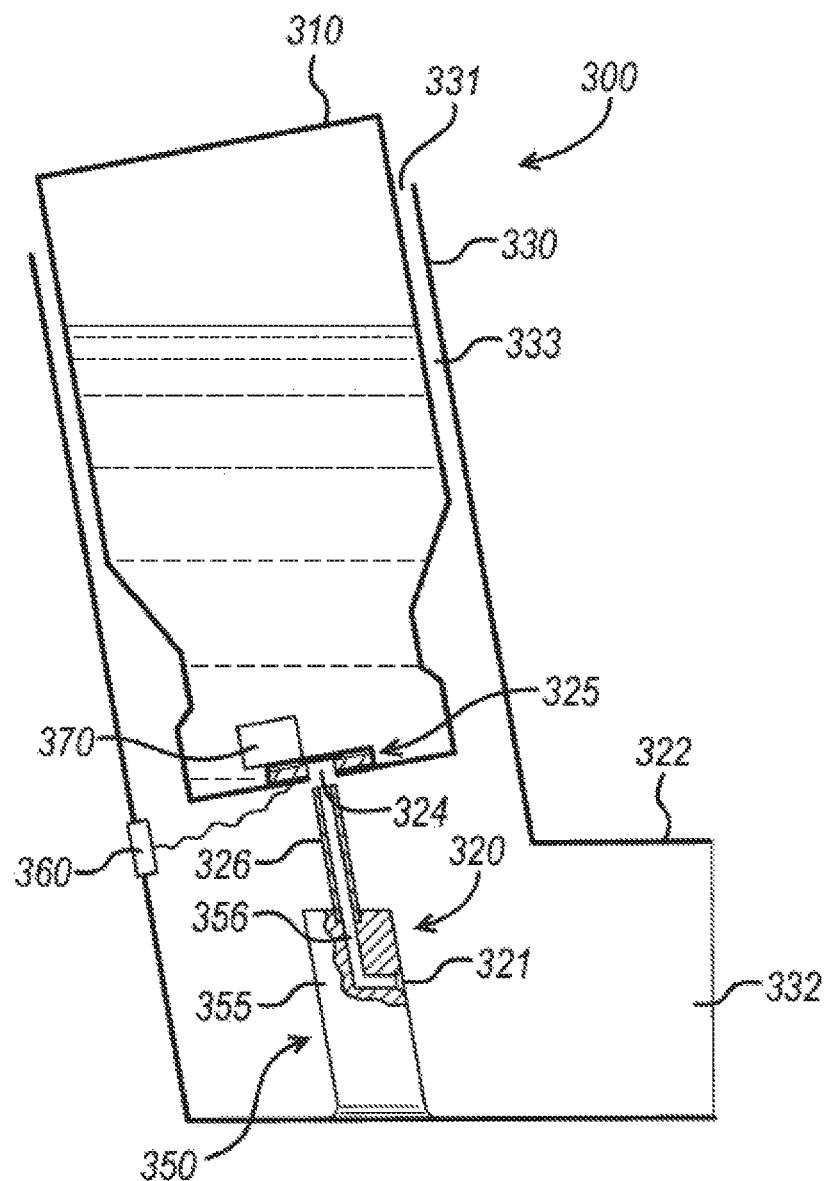
FIG. 3 is a schematic view of a third type of drug administration device, namely an inhaler.

FIG. 3 is a schematic view of a third type of drug administration device, namely an inhaler 300. Inhaler 300 includes a drug holder 310 in the form of a canister. The drug holder 310 contains a drug that would typically be in solution or suspension with a suitable carrier liquid. The inhaler 300 further comprises a dispensing mechanism 320, which includes a pressurized gas for pressurizing the drug holder 310, a valve 325 and nozzle 321. The valve 325 forms an outlet of the drug holder 310. The valve 325 comprises a narrow opening 324 formed in the drug holder 310 and a movable element 326 that controls the opening 324. When the movable element 326 is in a resting position, the valve 325 is in a closed or unactuated state in which the opening 324 is closed and the drug holder 310 is sealed. When the movable element 326 is actuated from the resting position to an actuated position, the valve 325 is actuated into an open state in which the opening 324 is open. Actuation of the movable element 326 from the resting position to the actuated position comprises moving the movable element 326 into the drug holder 310. The movable element 326 is resiliently biased into the resting position. In the open state of the valve 325, the pressurized gas propels the drug in solution or suspension with the suitable liquid out of the drug holder 310 through the opening 324 at high speed. The high speed passage of the liquid through the narrow opening 324 causes the liquid to be atomized, that is, to transform from a bulk liquid into a mist of fine droplets of liquid and/or into a gas cloud. A patient may inhale the mist of fine droplets and/or the gas cloud into a respiratory passage. Hence, the inhaler 300 is capable of delivering a drug retained within the drug holder 310 into a respiratory passage of a patient.

The drug holder 310 is removably held within a housing 330 of the inhaler 300. A passage 333 formed in the housing 330 connects a first opening 331 in the housing 330 and a second opening 332 in the housing 330. The drug holder 310 is received within the passage 333. The drug holder 310 is slidably insertable through the first opening 331 of the housing 330 into the passage 333. The second opening 332 of the housing 330 forms a mouthpiece 322 configured to be placed in a patient's mouth or a nosepiece configured to be placed in a patient's nostril, or a mask configured to be placed over the patient's mouth and nose. The drug holder 310, the first opening 331 and the passage 333 are sized such that air can flow through the passage 333, around the drug holder 310, between the first opening 331 and the second opening 332. The inhaler 300 may be provided with a dispensing mechanism protection mechanism 140 in the form of a cap (not shown) which can be fitted to the mouthpiece 322.

Inhaler 300 further comprises a trigger 350 including a valve actuation feature 355 configured to actuate the valve 325 when the trigger 350 is activated. The valve actuation feature 355 is a projection of the housing 330 into the passage 333. The drug holder 310 is slidably movable within the passage 333 from a first position into a second position. In the first position, an end of the movable element 326 in the resting position abuts the valve actuation feature 355. In the second position, the drug holder 310 can be displaced towards the valve actuation feature 355 such that the valve actuation feature 355 moves the movable element 326 into the drug holder 310 to actuate the valve 325 into the open state. The user's hand provides the necessary force to move the drug holder 310 from the first position to the second position against the resiliently biased movable element 326. The valve actuation feature 355 includes an inlet 356, which is connected to the nozzle 321. The inlet 356 of the valve actuation feature 355 is sized and positioned to couple to the opening 324 of the valve 325 such that the ejected mist of droplets and/or gas cloud can enter the inlet 356 and exit from the nozzle 321 into the passage 333. The nozzle 321 assists in the atomization of the bulk liquid into the mist of droplets and/or gas cloud.

The valve 325 provides a metering mechanism 370. The metering mechanism 370 is configured to close the valve after a measured amount of liquid, and therefore, drug, has passed through the opening 324. This allows a controlled dose to be administered to the patient. Typically, the measured amount of liquid is pre-set, however, the inhaler 300 may be equipped with a dosage selector 360 that is user operable to change the defined amount of liquid.

While the foregoing description relates to one particular example of an inhaler, this example is purely illustrative. The description should not be seen as limited only to such an inhaler. A person skilled in the art understands that numerous other types of inhaler and nebulizers may be used with the present disclosure. For example, the drug may be in a powdered form, the drug may be in liquid form, or the drug may be atomized by other forms of dispensing mechanism 320 including ultrasonic vibration, compressed gas, a vibrating mesh, or a heat source.

The inhalers of the present disclosure can be used to administer any of a variety of drugs, such as any of mometasone, fluticasone, ciclesonide, budesonide, beclomethasone, vilanterol, salmeterol, formoterol, umeclidinium, glycopyrrolate, tiotropium, aclidinium, indacaterol, salmeterol, and olodaterol.

Nasal Spray Device

Figure 4:
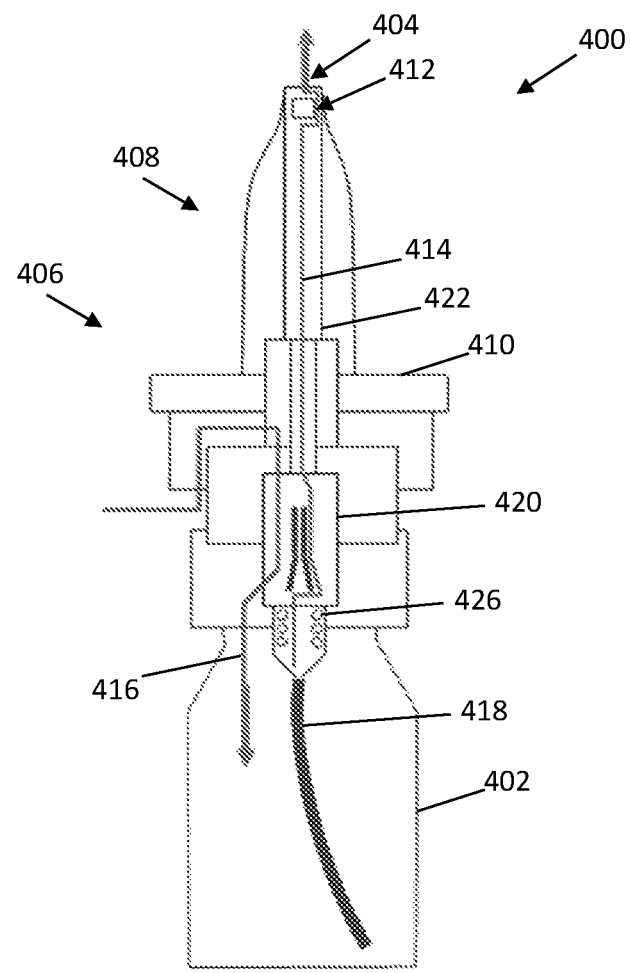
FIG. 4 is a schematic view of a fourth type of drug administration device, namely a nasal spray device.

FIG. 4 is a schematic view of a fourth type of drug administration device, namely a nasal spray device 400. The nasal spray device 400 is configured to expel a drug into a nose of a patient. The nasal spray device 400 includes a drug holder 402 configured to contain a drug therein for delivery from the device 400 to a patient. The drug holder 102 can have a variety of configurations, such as a bottle reservoir, a cartridge, a vial (as in this illustrated embodiment), a blow-fill-seal (BFS) capsule, a blister pack, etc. In an exemplary embodiment, the drug holder 402 is a vial. An exemplary vial is formed of one or more materials, e.g., glass, polymer(s), etc. In some embodiments, a vial can be formed of glass. In other embodiments, a vial can be formed of one or more polymers. In yet other embodiments, different portions of a vial can be formed of different materials. An exemplary vial can include a variety of features to facilitate sealing and storing a drug therein, as described herein and illustrated in the drawings. However, a person skilled in the art will appreciate that the vials can include only some of these features and/or can include a variety of other features known in the art. The vials described herein are merely intended to represent certain exemplary embodiments.

An opening 404 of the nasal spray device 400 through which the drug exits the nasal spray device 400 is formed in in a dispensing head 406 of the nasal spray device 400 in a tip 408 of the dispensing head 406. The tip 408 is configured to be inserted into a nostril of a patient. In an exemplary embodiment, the tip 408 is configured to be inserted into a first nostril of the patient during a first stage of operation of the nasal spray device 400 and into a second nostril of the patient during a second stage of operation of the nasal spray device 400. The first and second stages of operation involve two separate actuations of the nasal spray device 400, a first actuation corresponding to a first dose of the drug being delivered and a second actuation corresponding to a second dose of the drug being delivered. In some embodiments, the nasal spray device 400 is configured to be actuated only once to deliver one nasal spray. In some embodiments, the nasal spray device 400 is configured to be actuated three or more times to deliver three or more nasal sprays, e.g., four, five, six, seven, eight, nine, ten, etc.

The dispensing head 406 includes a depth guide 410 configured to contact skin of the patient between the patient's first and second nostrils, such that a longitudinal axis of the dispensing head 406 is substantially aligned with a longitudinal axis of the nostril in which the tip 408 is inserted. A person skilled in the art will appreciate that the longitudinal axes may not be precisely aligned but nevertheless be considered to be substantially aligned due to any number of factors, such as manufacturing tolerances and sensitivity of measurement equipment.

In an exemplary embodiment, as in FIG. 4, the dispensing head 406 has a tapered shape in which the dispensing head 406 has a smaller diameter at its distal end than at its proximal end where the opening 404 is located. The opening 404 having a relatively small diameter facilitates spray of the drug out of the opening 404, as will be appreciated by a person skilled in the art. A spray chamber 412 through which the drug is configured to pass before exiting the opening 404 is located within a proximal portion of the tapered dispensing head 406, distal to the opening 404. When the drug passes through the spray chamber 412 at speed, the spray chamber 412 facilitates production of a fine mist that exits through the opening 404 with a consistent spray pattern. Arrow 414 in FIG. 4 illustrates a path of travel of the drug from the drug holder 402 and out of the opening 404.

In some embodiments, the dispensing head 406 can include two tips 408 each having an opening 404 therein such that the nasal spray device 400 is configured to simultaneously deliver doses of drug into two nostrils in response to a single actuation.

The dispensing head 406 is configured to be pushed toward the drug holder 402, e.g., depressed by a user pushing down on the depth guide 410, to actuate the nasal spray device 400. In other words, the dispensing head 406 is configured as an actuator to be actuated to drive the drug from the drug holder 402 and out of the nasal spray device 400. In an exemplary embodiment, the nasal spray device 400 is configured to be self-administered such that the user who actuates the nasal spray device 400 is the patient receiving the drug from the nasal spray device 400, although another person can actuate the nasal spray device 400 for delivery into another person.

The actuation, e.g., depressing, of the dispensing head 406 is configured to cause venting air to enter the drug holder 402, as shown by arrow 416 in FIG. 4. The air entering the drug holder 402 displaces drug in the drug holder through a tube 418 and then into a metering chamber 420, which displaces drug proximally through a cannula 422, through the spray chamber 412, and then out of the opening 404. In response to release of the dispensing head 406, e.g., a user stops pushing downward on the dispensing head 406, a bias spring 426 causes the dispensing head 406 to return to its default, resting position to position the dispensing head 406 relative to the drug holder 402 for a subsequent actuation and drug delivery.

While the foregoing description relates to one particular example of a nasal spray device, this example is purely illustrative. The description should not be seen as limited only to such a nasal spray device. A person skilled in the art understands that the nasal spray device 400 can include different features in different embodiments depending upon various requirements. For example, the nasal spray device 400 can lack the depth guide 410 and/or may include any one or more of a device indicator, a sensor, a communications interface, a processor, a memory, and a power supply.

The nasal spray devices of the present disclosure can be used to administer any of a variety of drugs, such as any of ketamine (e.g., Ketalar®), esketamine (e.g., Spravato®, Ketanest®, and Ketanest-S®), naloxone (e.g., Narcan®), and sumatriptan (e.g., Imitrex®).

Drug Administration Device

As will be appreciated from the foregoing, various components of drug delivery devices are common to all such devices. These components form the essential components of a universal drug administration device. A drug administration device delivers a drug to a patient, where the drug is provided in a defined dosage form within the drug administration device.

Figure 5A:
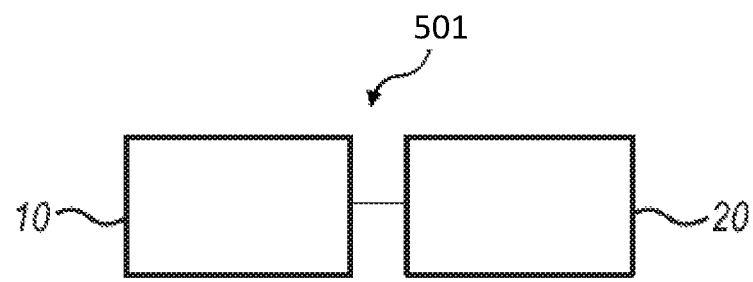
FIG. 5A is a schematic view of a general drug administration device.
Figure 5B:
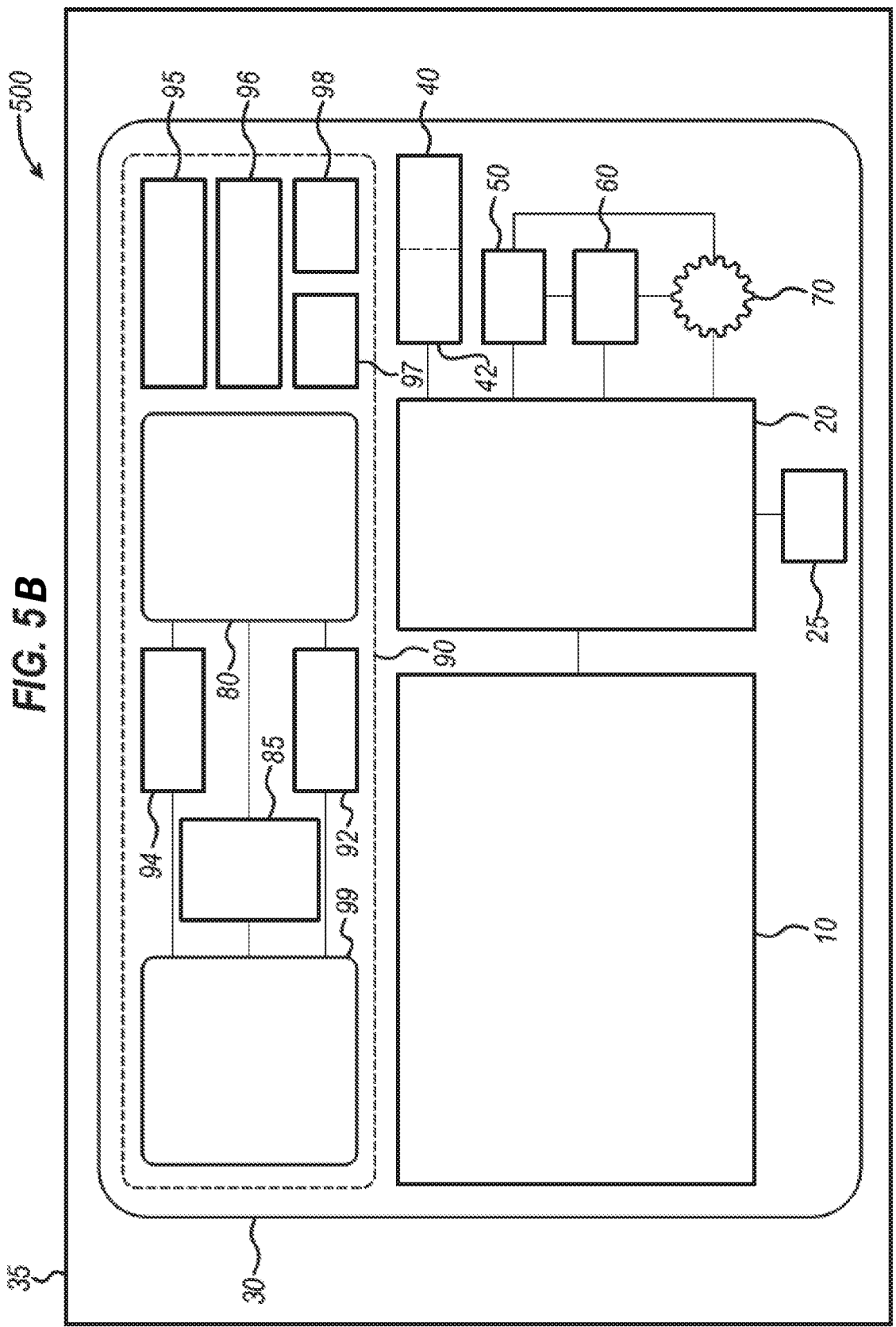
FIG. 5B is a schematic view of a universal drug administration device.

FIG. 5A is a generalized schematic view of such a universal drug administration device 501, and FIG. 5B is an exemplary embodiment of such a universal drug administration device 500. Examples of the universal drug administration device 500 include injection devices (e.g., autoinjectors, jet injectors, and infusion pumps), nasal spray devices, and inhalers.

As shown in FIG. 5A, drug administration device 501 includes in general form the features of a drug holder 10 and a dispensing mechanism 20. The drug holder 10 holds a drug in a dosage form to be administered. The dispensing mechanism 20 is configured to release the dosage form from the drug holder 10 so that the drug can be administered to a patient.

FIG. 5B shows a further universal drug administration device 500 which includes a number of additional features. A person skilled in the art understands that these additional features are optional for different embodiments, and can be utilized in a variety of different combinations such that the additional features may be present or may be omitted from a given embodiment of a particular drug administration device, depending upon requirements, such as the type of drug, dosage form of the drug, medical indication being treated with the drug, safety requirements, whether the device is powered, whether the device is portable, whether the device is used for self-administration, and many other requirements which will be appreciated by a person skilled in the art. Similar to the universal device of FIG. 5A, the drug administration device 500 comprises a housing 30 which accommodates the drug holder 10 and dispensing mechanism 20.

The device 500 is provided with a triggering mechanism 50 for initiating the release of the drug from the drug holder 10 by the dispensing mechanism 20. The device 500 includes the feature of a metering/dosing mechanism 70 which measures out a set dose to be released from the drug holder 10 via the dispensing mechanism 20. In this manner, the drug administration device 500 can provide a known dose of determined size. The device 500 comprises a dosage selector 60 which enables a user to set the dose volume of drug to be measured out by the metering mechanism 70. The dose volume can be set to one specific value of a plurality of predefined discrete dose volumes, or any value of a predefined dose volume within a range of dose volumes.

The device 500 can comprise a device operation prevention mechanism 40 or 25 which when in a locked state will prevent and/or stop the dispensing mechanism 20 from releasing the drug out of the drug holder 10, and when in an unlocked state will permit the dispensing mechanism 20 to release the drug dosage from out of the drug holder 10. This can prevent accidental administration of the drug, for example to prevent dosing at an incorrect time, or for preventing inadvertent actuation. The device 500 also includes a dispensing mechanism protection mechanism 42 which prevents access to at least a part of the dispensing mechanism 20, for example for safety reasons. Device operation prevention mechanism 40 and dispensing mechanism protection mechanism 42 may be the same component.

The device 500 can include a device indicator 85 which is configured to present information about the status of the drug administration device and/or the drug contained therein. The device indicator 85 may be a visual indicator, such as a display screen, or an audio indicator. The device 500 includes a user interface 80 which can be configured to present a user of the device 500 with information about the device 500 and/or to enable the user to control the device 500. The device 500 includes a device sensor 92 which is configured to sense information relating to the drug administration device and/or the drug contained therein, for example dosage form and device parameters. As an example, in embodiments which include a metering mechanism 70 and a dosage selector 60, the embodiment may further include one or more device sensors 92 configured to sense one or more of: the dose selected by a user using dosage selector 60, the dose metered by the metering mechanism 70 and the dose dispensed by the dispensing mechanism 20. Similarly, an environment sensor 94 is provided which is configured to sense information relating to the environment in which the device 500 is present, such as the temperature of the environment, the humidity of the environment, location, and time. There may be a dedicated location sensor 98 which is configured to determine the geographical location of the device 500, e.g., via satellite position determination, such as GPS. The device 500 also includes a communications interface 99 which can communicate externally data which has been acquired from the various sensors about the device and/or drug.

If required, the device 500 comprises a power supply 95 for delivering electrical power to one or more electrical components of the device 500. The power supply 95 can be a source of power which is integral to device 500 and/or a mechanism for connecting device 500 to an external source of power. The drug administration device 500 also includes a device computer system 90 including processor 96 and memory 97 powered by the power supply 95 and in communication with each other, and optionally with other electrical and control components of the device 500, such as the environment sensor 94, location sensor 98, device sensor 92, communications interface 99, and/or indicator 85. The processor 96 is configured to obtain data acquired from the environment sensor 94, device sensor 92, communications interface 99, location sensor 98, and/or user interface 80 and process it to provide data output, for example to indicator 85 and/or to communications interface 99.

In some embodiments, the drug administration device 500 is enclosed in packaging 35. The packaging 35 may further include a combination of a processor 96, memory 97, user interface 80, device indicator 85, device sensor 92, location sensor 98 and/or environment sensors 94 as described herein, and these may be located externally on the housing of the device 500.

A person skilled in the art will appreciate that the universal drug administration device 500 comprising the drug holder 10 and dispensing mechanism 20 can be provided with a variety of the optional features described above, in a number of different combinations. Moreover, the drug administration device 500 can include more than one drug holder 10, optionally with more than one dispensing mechanism 20, such that each drug holder has its own associated dispensing mechanism 20.

Drug Dosage Forms

Conventionally, drug administration devices utilize a liquid dosage form. It will be appreciated, however that other dosage forms are available.

One such common dosage form is a tablet. The tablet may be formed from a combination of the drug and an excipient that are compressed together. Other dosage forms are pastes, creams, powders, ear drops, and eye drops.

Further examples of drug dosage forms include dermal patches, drug eluting stents and intrauterine devices. In these examples, the body of the device comprises the drug and may be configured to allow the release of the drug under certain circumstances. For example, a dermal patch may comprise a polymeric composition containing the drug. The polymeric composition allows the drug to diffuse out of the polymeric composition and into the skin of the patient. Drug eluting stents and intrauterine devices can operate in an analogous manner. In this way, the patches, stents and intrauterine devices may themselves be considered drug holders with an associated dispensing mechanism.

Any of these dosage forms can be configured to have the drug release initiated by certain conditions. This can allow the drug to be released at a desired time or location after the dosage form has been introduced into the patient. In particular, the drug release may be initiated by an external stimulus. Moreover, these dosage forms can be contained prior to administration in a housing, which may be in the form of packaging. This housing may contain some of the optional features described above which are utilized with the universal drug administration device 500.

The drug administered by the drug administration devices of the present disclosure can be any substance that causes a change in an organism's physiology or psychology when consumed. Examples of drugs that the drug administration devices of the present disclosure can administer include 5-alpha-reductase inhibitors, 5-aminosalicylates, 5HT3 receptor antagonists, ACE inhibitors with calcium channel blocking agents, ACE inhibitors with thiazides, adamantane antivirals, adrenal cortical steroids, adrenal corticosteroid inhibitors, adrenergic bronchodilators, agents for hypertensive emergencies, agents for pulmonary hypertension, aldosterone receptor antagonists, alkylating agents, allergenics, alpha-glucosidase inhibitors, alternative medicines, amebicides, aminoglycosides, aminopenicillins, aminosalicylates, AMPA receptor antagonists, amylin analogs, analgesic combinations, analgesics, androgens and anabolic steroids, Angiotensin Converting Enzyme Inhibitors, angiotensin II inhibitors with calcium channel blockers, angiotensin II inhibitors with thiazides, angiotensin receptor blockers, angiotensin receptor blockers and neprilysin inhibitors, anorectal preparations, anorexiants, antacids, anthelmintics, anti-angiogenic ophthalmic agents, anti-CTLA-4 monoclonal antibodies, anti-infectives, anti-PD-1 monoclonal antibodies, antiadrenergic agents (central) with thiazides, antiadrenergic agents (peripheral) with thiazides, antiadrenergic agents, centrally acting, antiadrenergic agents, peripherally acting, antiandrogens, antianginal agents, antiarrhythmic agents, antiasthmatic combinations, antibiotics/antineoplastics, anticholinergic antiemetics, anticholinergic antiparkinson agents, anticholinergic bronchodilators, anticholinergic chronotropic agents, anticholinergics/antispasmodics, anticoagulant reversal agents, anticoagulants, anticonvulsants, antidepressants, antidiabetic agents, antidiabetic combinations, antidiarrheals, antidiuretic hormones, antidotes, antiemetic/antivertigo agents, antifungals, antigonadotropic agents, antigout agents, antihistamines, antihyperlipidemic agents, antihyperlipidemic combinations, antihypertensive combinations, antihyperuricemic agents, antimalarial agents, antimalarial combinations, antimalarial quinolones, antimanic agents, antimetabolites, antimigraine agents, antineoplastic combinations, antineoplastic detoxifying agents, antineoplastic interferons, antineoplastics, antiparkinson agents, antiplatelet agents, antipseudomonal penicillins, antipsoriatics, antipsychotics, antirheumatics, antiseptic and germicides, antithyroid agents, antitoxins and antivenins, antituberculosis agents, antituberculosis combinations, antitussives, antiviral agents, antiviral boosters, antiviral combinations, antiviral interferons, anxiolytics, sedatives, and hypnotics, aromatase inhibitors, atypical antipsychotics, azole antifungals, bacterial vaccines, barbiturate anticonvulsants, barbiturates, BCR-ABL tyrosine kinase inhibitors, benzodiazepine anticonvulsants, benzodiazepines, beta blockers with calcium channel blockers, beta blockers with thiazides, beta-adrenergic blocking agents, beta-lactamase inhibitors, bile acid sequestrants, biologicals, bisphosphonates, bone morphogenetic proteins, bone resorption inhibitors, bronchodilator combinations, bronchodilators, calcimimetics, calcineurin inhibitors, calcitonin, calcium channel blocking agents, carbamate anticonvulsants, carbapenems, carbapenems/beta-lactamase inhibitors, carbonic anhydrase inhibitor anticonvulsants, carbonic anhydrase inhibitors, cardiac stressing agents, cardioselective beta blockers, cardiovascular agents, catecholamines, cation exchange resins, CD20 monoclonal antibodies, CD30 monoclonal antibodies, CD33 monoclonal antibodies, CD38 monoclonal antibodies, CD52 monoclonal antibodies, CDK 4/6 inhibitors, central nervous system agents, cephalosporins, cephalosporins/beta-lactamase inhibitors, cerumenolytics, CFTR combinations, CFTR potentiators, CGRP inhibitors, chelating agents, chemokine receptor antagonist, chloride channel activators, cholesterol absorption inhibitors, cholinergic agonists, cholinergic muscle stimulants, cholinesterase inhibitors, CNS stimulants, coagulation modifiers, colony stimulating factors, contraceptives, corticotropin, coumarins and indandiones, cox-2 inhibitors, decongestants, dermatological agents, diagnostic radiopharmaceuticals, diarylquinolines, dibenzazepine anticonvulsants, digestive enzymes, dipeptidyl peptidase 4 inhibitors, diuretics, dopaminergic antiparkinsonism agents, drugs used in alcohol dependence, echinocandins, EGFR inhibitors, estrogen receptor antagonists, estrogens, expectorants, factor Xa inhibitors, fatty acid derivative anticonvulsants, fibric acid derivatives, first generation cephalosporins, fourth generation cephalosporins, functional bowel disorder agents, gallstone solubilizing agents, gamma-aminobutyric acid analogs, gamma-aminobutyric acid reuptake inhibitors, gastrointestinal agents, general anesthetics, genitourinary tract agents, GI stimulants, glucocorticoids, glucose elevating agents, glycopeptide antibiotics, glycoprotein platelet inhibitors, glycylcyclines, gonadotropin releasing hormones, gonadotropin-releasing hormone antagonists, gonadotropins, group I antiarrhythmics, group II antiarrhythmics, group III antiarrhythmics, group IV antiarrhythmics, group V antiarrhythmics, growth hormone receptor blockers, growth hormones, guanylate cyclase-C agonists, *H. pylori* eradication agents, H2 antagonists, hedgehog pathway inhibitors, hematopoietic stem cell mobilizer, heparin antagonists, heparins, HER2 inhibitors, herbal products, histone deacetylase inhibitors, hormones, hormones/antineoplastics, hydantoin anticonvulsants, hydrazide derivatives, illicit (street) drugs, immune globulins, immunologic agents, immunostimulants, immunosuppressive agents, impotence agents, in vivo diagnostic biologicals, incretin mimetics, inhaled anti-infectives, inhaled corticosteroids, inotropic agents, insulin, insulin-like growth factors, integrase strand transfer inhibitor, interferons, interleukin inhibitors, interleukins, intravenous nutritional products, iodinated contrast media, ionic iodinated contrast media, iron products, ketolides, laxatives, leprostatics, leukotriene modifiers, lincomycin derivatives, local injectable anesthetics, local injectable anesthetics with corticosteroids, loop diuretics, lung surfactants, lymphatic staining agents, lysosomal enzymes, macrolide derivatives, macrolides, magnetic resonance imaging contrast media, mast cell stabilizers, medical gas, meglitinides, metabolic agents, methylxanthines, mineralocorticoids, minerals and electrolytes, miscellaneous agents, miscellaneous analgesics, miscellaneous antibiotics, miscellaneous anticonvulsants, miscellaneous antidepressants, miscellaneous antidiabetic agents, miscellaneous antiemetics, miscellaneous antifungals, miscellaneous antihyperlipidemic agents, miscellaneous antihypertensive combinations, miscellaneous antimalarials, miscellaneous antineoplastics, miscellaneous antiparkinson agents, miscellaneous antipsychotic agents, miscellaneous antituberculosis agents, miscellaneous antivirals, miscellaneous anxiolytics, sedatives and hypnotics, miscellaneous bone resorption inhibitors, miscellaneous cardiovascular agents, miscellaneous central nervous system agents, miscellaneous coagulation modifiers, miscellaneous diagnostic dyes, miscellaneous diuretics, miscellaneous genitourinary tract agents, miscellaneous GI agents, miscellaneous hormones, miscellaneous metabolic agents, miscellaneous ophthalmic agents, miscellaneous otic agents, miscellaneous respiratory agents, miscellaneous sex hormones, miscellaneous topical agents, miscellaneous uncategorized agents, miscellaneous vaginal agents, mitotic inhibitors, monoamine oxidase inhibitors, mouth and throat products, mTOR inhibitors, mucolytics, multikinase inhibitors, muscle relaxants, mydriatics, narcotic analgesic combinations, narcotic analgesics, nasal anti-infectives, nasal antihistamines and decongestants, nasal lubricants and irrigations, nasal preparations, nasal steroids, natural penicillins, neprilysin inhibitors, neuraminidase inhibitors, neuromuscular blocking agents, neuronal potassium channel openers, next generation cephalosporins, nicotinic acid derivatives, NK1 receptor antagonists, NNRTIs, non-cardioselective beta blockers, non-iodinated contrast media, non-ionic iodinated contrast media, non-sulfonylureas, Nonsteroidal anti-inflammatory drugs, NS5A inhibitors, nucleoside reverse transcriptase inhibitors (NRTIs), nutraceutical products, nutritional products, ophthalmic anesthetics, ophthalmic anti-infectives, ophthalmic anti-inflammatory agents, ophthalmic antihistamines and decongestants, ophthalmic diagnostic agents, ophthalmic glaucoma agents, ophthalmic lubricants and irrigations, ophthalmic preparations, ophthalmic steroids, ophthalmic steroids with anti-infectives, ophthalmic surgical agents, oral nutritional supplements, other immunostimulants, other immunosuppressants, otic anesthetics, otic anti-infectives, otic preparations, otic steroids, otic steroids with anti-infectives, oxazolidinedione anticonvulsants, oxazolidinone antibiotics, parathyroid hormone and analogs, PARP inhibitors, PCSK9 inhibitors, penicillinase resistant penicillins, penicillins, peripheral opioid receptor antagonists, peripheral opioid receptor mixed agonists/antagonists, peripheral vasodilators, peripherally acting antiobesity agents, phenothiazine antiemetics, phenothiazine antipsychotics, phenylpiperazine antidepressants, phosphate binders, PI3K inhibitors, plasma expanders, platelet aggregation inhibitors, platelet-stimulating agents, polyenes, potassium sparing diuretics with thiazides, potassium-sparing diuretics, probiotics, progesterone receptor modulators, progestins, prolactin inhibitors, prostaglandin D2 antagonists, protease inhibitors, protease-activated receptor-1 antagonists, proteasome inhibitors, proton pump inhibitors, psoralens, psychotherapeutic agents, psychotherapeutic combinations, purine nucleosides, pyrrolidine anticonvulsants, quinolones, radiocontrast agents, radiologic adjuncts, radiologic agents, radiologic conjugating agents, radiopharmaceuticals, recombinant human erythropoietins, renin inhibitors, respiratory agents, respiratory inhalant products, rifamycin derivatives, salicylates, sclerosing agents, second generation cephalosporins, selective estrogen receptor modulators, selective immunosuppressants, selective phosphodiesterase-4 inhibitors, selective serotonin reuptake inhibitors, serotonin-norepinephrine reuptake inhibitors, serotoninergic neuroenteric modulators, sex hormone combinations, sex hormones, SGLT-2 inhibitors, skeletal muscle relaxant combinations, skeletal muscle relaxants, smoking cessation agents, somatostatin and somatostatin analogs, spermicides, statins, sterile irrigating solutions, streptogramins, *Streptomyces* derivatives, succinimide anticonvulsants, sulfonamides, sulfonylureas, synthetic ovulation stimulants, tetracyclic antidepressants, tetracyclines, therapeutic radiopharmaceuticals, therapeutic vaccines, thiazide diuretics, thiazolidinediones, thioxanthenes, third generation cephalosporins, thrombin inhibitors, thrombolytics, thyroid drugs, TNF alfa inhibitors, tocolytic agents, topical acne agents, topical agents, topical allergy diagnostic agents, topical anesthetics, topical anti-infectives, topical anti-rosacea agents, topical antibiotics, topical antifungals, topical antihistamines, topical antineoplastics, topical antipsoriatics, topical antivirals, topical astringents, topical debriding agents, topical depigmenting agents, topical emollients, topical keratolytics, topical non-steroidal anti-inflammatories, topical photochemotherapeutics, topical rubefacient, topical steroids, topical steroids with anti-infectives, transthyretin stabilizers, triazine anticonvulsants, tricyclic antidepressants, trifunctional monoclonal antibodies, ultrasound contrast media, upper respiratory combinations, urea anticonvulsants, urea cycle disorder agents, urinary anti-infectives, urinary antispasmodics, urinary pH modifiers, uterotonic agents, vaccine combinations, vaginal anti-infectives, vaginal preparations, vasodilators, vasopressin antagonists, vasopressors, VEGF/VEGFR inhibitors, viral vaccines, viscosupplementation agents, vitamin and mineral combinations, vitamins, or VMAT2 inhibitors. The drug administration devices of the present disclosure may administer a drug selected from epinephrine, Rebif, Enbrel, Aranesp, atropine, pralidoxime chloride, diazepam, insulin, antropine sulfate, avibactam sodium, bendamustine hydrochloride, carboplatin, daptomycin, epinephrine, levetiracetam, oxaliplatin, paclitaxel, pantoprazole sodium, treprostinil, vasopressin, voriconazole, zoledronic acid, mometasone, fluticasone, ciclesonide, budesonide, beclomethasone, vilanterol, salmeterol, formoterol, umeclidinium, glycopyrrolate, tiotropium, aclidinium, indacaterol, salmeterol, and olodaterol.

As mentioned above, any of a variety of drugs can be delivered using a drug administration device. Examples of drugs that can be delivered using a drug administration device as described herein include Remicade® (infliximab), Stelara® (ustekinumab), Simponi® (golimumab), Simponi Aria® (golimumab), Darzalex® (daratumumab), Tremfya® (guselkumab), Eprex® (epoetin alfa), Risperdal Constra® (risperidone), Invega Sustenna® (paliperidone palmitate), Spravato® (esketamine), ketamine, and Invega Trinza® (paliperidone palmitate).

Drug Housing

As described above, a dosage form can be provided in a holder that is appropriate for the particular dosage form being utilized. For example, a drug in a liquid dosage form can be held prior to administration within a holder in the form of a vial with a stopper, or a syringe with a plunger. A drug in solid or powder dosage form, e.g., as tablets, may be contained in a housing which is arranged to hold the tablets securely prior to administration.

The housing may comprise one or a plurality of drug holders, where each holder contains a dosage form, e.g., the drug can be in a tablet dosage form and the housing can be in the form of a blister pack, where a tablet is held within each of a plurality of holders. The holders being in the form of recesses in the blister pack.

FIG. 6 depicts a housing 630 that comprises a plurality of drug holders 610 that each contain a dosage form 611. The housing 630 may have at least one environment sensor 94, which is configured to sense information relating to the environment in which the housing 630 is present, such as the temperature of the environment, time or location. The housing 630 may include at least one device sensor 92, which is configured to sense information relating to the drug of the dosage form 611 contained within the holder 610. There may be a dedicated location sensor 98 which is configured to determine the geographical location of the housing 630, e.g., via satellite position determination, such as GPS.

The housing 630 may include an indicator 85 which is configured to present information about the status of the drug of the dosage form 611 contained within the holder 610 to a user of the drug housing. The housing 630 may also include a communications interface 99 which can communicate information externally via a wired or wireless transfer of data pertaining to the drug housing 630, environment, time or location and/or the drug itself.

If required, the housing 630 may comprise a power supply 95 for delivering electrical power to one or more electrical components of the housing 630. The power supply 95 can be a source of power which is integral to housing 630 and/or a mechanism for connecting the housing 630 to an external source of power. The housing 630 may also include a device computer system 90 including processor 96 and memory 97 powered by the power supply 95 and in communication with each other, and optionally with other electrical and control components of the housing 630, such as the environment sensor 94, location sensor 98, device sensor 92, communications interface 99, and/or indicator 85. The processor 96 is configured to obtain data acquired from the environment sensor 94, device sensor 92, communications interface 99, location sensor 98, and/or user interface 80 and process it to provide data output, for example to indicator 85 and/or to communications interface 99.

The housing 630 can be in the form of packaging. Alternatively, additional packaging may be present to contain and surround the housing 630.

The holder 610 or the additional packaging may themselves comprise one or more of the device sensor 92, the environment sensor 94, the indicator 85, the communications interface 99, the power supply 95, location sensor 98, and device computer system including the processor 96 and the memory 97, as described above.

Electronic Communication

Figure 7:
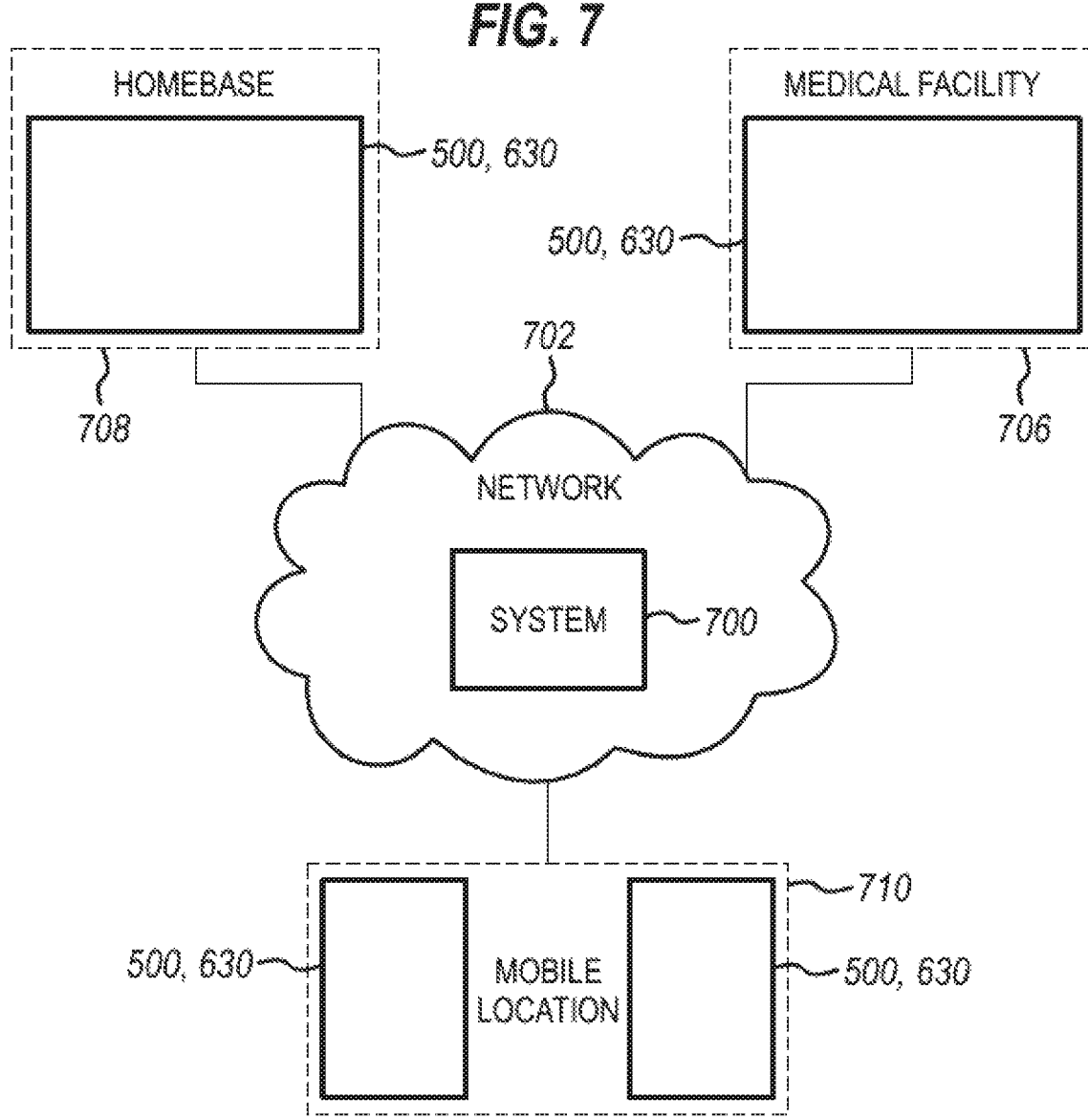
FIG. 7 is a schematic view of one embodiment of a communication network system with which the drug administration devices and housing can operate.

As mentioned above, communications interface 99 may be associated with the drug administration device 500 or drug housing 630, by being included within or on the housing 30, 630, or alternatively within or on the packaging 35. Such a communications interface 99 can be configured to communicate with a remote computer system, such as central computer system 700 shown in FIG. 7. As shown in FIG. 7, the communications interface 99 associated with drug administration device 500 or housing 630 is configured to communicate with a central computer system 700 through a communications network 702 from any number of locations such as a medical facility 706, e.g., a hospital or other medical care center, a home base 708 (e.g., a patient's home or office or a care taker's home or office), or a mobile location 710. The communications interface 99 can be configured to access the system 700 through a wired and/or wireless connection to the network 702. In an exemplary embodiment, the communications interface 99 of FIG. 6 is configured to access the system 700 wirelessly, e.g., through Wi-Fi connection(s), which can facilitate accessibility of the system 700 from almost any location in the world.

A person skilled in the art will appreciate that the system 700 can include security features such that the aspects of the system 700 available to any particular user can be determined based on, e.g., the identity of the user and/or the location from which the user is accessing the system. To that end, each user can have a unique username, password, biometric data, and/or other security credentials to facilitate access to the system 700. The received security parameter information can be checked against a database of authorized users to determine whether the user is authorized and to what extent the user is permitted to interact with the system, view information stored in the system, and so forth.

Computer System

As discussed herein, one or more aspects or features of the subject matter described herein, for example components of the central computer system 700, processor 96, power supply 95, memory 97, communications interface 99, user interface 80, device indicators 85, device sensors 92, environment sensors 94 and location sensors 98, can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communications network, e.g., the Internet, a wireless wide area network, a local area network, a wide area network, or a wired network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein, for example user interface 80 (which can be integrated or separate to the administration device 500 or housing 630), can be implemented on a computer having a display screen, such as for example a cathode ray tube (CRT) or a liquid crystal display (LCD) or a light emitting diode (LED) monitor for displaying information to the user. The display screen can allow input thereto directly (e.g., as a touch screen) or indirectly (e.g., via an input device such as a keypad or voice recognition hardware and software). Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. As described above, this feedback may be provided via one or more device indicators 85 in addition to the user interface 80. The device indicators 85 can interact with one or more of device sensor(s) 92, environment sensor(s) 94 and/or location sensor(s) 98 in order to provide this feedback, or to receive input from the user.

Figure 8:
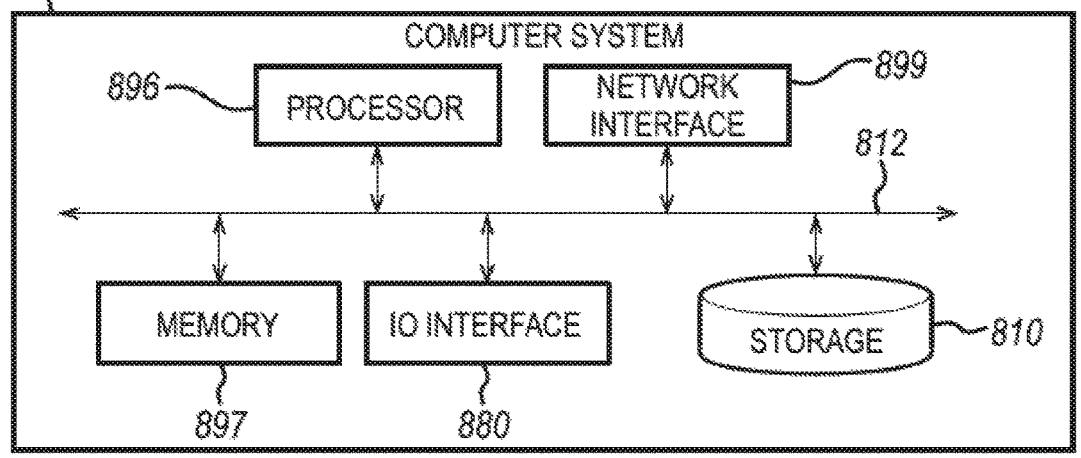
FIG. 8 is a schematic view of one embodiment of a computer system with which the drug administration devices and housing can operate.

FIG. 8 illustrates one exemplary embodiment of the computer system 700, depicted as computer system 800. The computer system includes one or more processors 896 configured to control the operation of the computer system 800. The processor(s) 896 can include any type of microprocessor or central processing unit (CPU), including programmable general-purpose or special-purpose microprocessors and/or any one of a variety of proprietary or commercially available single or multi-processor systems. The computer system 800 also includes one or more memories 897 configured to provide temporary storage for code to be executed by the processor(s) 896 or for data acquired from one or more users, storage devices, and/or databases. The memory 897 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system are coupled to a bus system 812. The illustrated bus system 812 is an abstraction that represents any one or more separate physical busses, communication lines/interfaces, and/or multi-drop or point-to-point connections, connected by appropriate bridges, adapters, and/or controllers. The computer system 800 also includes one or more network interface(s) 899 (also referred to herein as a communications interface), one or more input/output (IO) interface(s) 880, and one or more storage device(s) 810.

The communications interface(s) 899 are configured to enable the computer system to communicate with remote devices, e.g., other computer systems and/or devices 500 or housings 630, over a network, and can be, for example, remote desktop connection interfaces, Ethernet adapters, and/or other local area network (LAN) adapters. The IO interface(s) 880 include one or more interface components to connect the computer system 800 with other electronic equipment. For example, the IO interface(s) 880 can include high speed data ports, such as universal serial bus (USB) ports, 1394 ports, Wi-Fi, Bluetooth, etc. Additionally, the computer system can be accessible to a human user, and thus the IO interface(s) 880 can include displays, speakers, keyboards, pointing devices, and/or various other video, audio, or alphanumeric interfaces. The storage device(s) 810 include any conventional medium for storing data in a non-volatile and/or non-transient manner. The storage device(s) 810 are thus configured to hold data and/or instructions in a persistent state in which the value(s) are retained despite interruption of power to the computer system. The storage device(s) 810 can include one or more hard disk drives, flash drives, USB drives, optical drives, various media cards, diskettes, compact discs, and/or any combination thereof and can be directly connected to the computer system or remotely connected thereto, such as over a network. In an exemplary embodiment, the storage device(s) 810 include a tangible or non-transitory computer readable medium configured to store data, e.g., a hard disk drive, a flash drive, a USB drive, an optical drive, a media card, a diskette, or a compact disc.

The elements illustrated in FIG. 8 can be some or all of the elements of a single physical machine. In addition, not all of the illustrated elements need to be located on or in the same physical machine.

The computer system 800 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XMIL), scripts, controls, and so forth. The computer system 800 can also include a web server for generating and/or delivering the web pages to client computer systems.

As shown in FIG. 7, the computer system 800 of FIG. 8 as described above may form the components of the central computer system 700 which is in communication with one or more of the device computer systems 90 of the one or more individual drug administration devices 500 or housings 630. Data, such as operational data of the devices 500 or housings 630, medical data acquired of patients by such devices 500 or housings 630 can be exchanged between the central and device computer systems 700, 90.

As mentioned the computer system 800 as described above may also form the components of a device computer system 90 which is integrated into or in close proximity to the drug administration device 500 or housing 630. In this regard, the one or more processors 896 correspond to the processor 96, the network interface 799 corresponds to the communications interface 99, the IO interface 880 corresponds to the user interface 80, and the memory 897 corresponds to the memory 97. Moreover, the additional storage 810 may also be present in device computer system 90.

In an exemplary embodiment, the computer system 800 can form the device computer system 90 as a single unit, e.g., contained within a single drug administration device housing 30, contained within a single package 35 for one or more drug administration devices 500, or a housing 630 that comprises a plurality of drug holders 610. The computer system 800 can form the central computer system 700 as a single unit, as a single server, or as a single tower.

The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

The computer system can also include any of a variety of other software and/or hardware components, including by way of example, operating systems and database management systems. Although an exemplary computer system is depicted and described herein, it will be appreciated that this is for sake of generality and convenience. In other embodiments, the computer system may differ in architecture and operation from that shown and described here. For example, the memory 897 and storage device 810 can be integrated together or the communications interface 899 can be omitted if communication with another computer system is not necessary.

Implementations

In at least some implementations, a communications interface, such as the communications interface 99 discussed above, can be configured to communicate in a secure and anonymized manner with a remote computer system, such as central computer system 700 discussed above. In this way, data related to a patient's drug administration device, a drug dispensable or dispensed therefrom, and/or a physiological parameter can be transmitted from the communications interface to the remote computer system without any identifying patient information that would compromise the patient's privacy if the data was intercepted by an unauthorized party. A remembered link can be established between the device that includes the communications interface, e.g., any of the drug administration devices of FIGS. 1-5B, any of the drug housings 30, 630 of FIGS. 5B and 6, the packaging 35 of FIG. 5B, a sensor, etc., and the remote computer system to facilitate this secure, anonymous communication of data. In an exemplary embodiment the remembered link includes an established key stored at each of the device and the remote computer system that is unique to the device and the remote computer system, thereby allowing the remote computer system to receive anonymous data from the device but, using the key, be able to accurately identify the data as being from that particular device and, therefore, as being associated with the particular patient associated with that particular device as previously programmed at the computer system or available thereto from another computer system. The remote computer system may therefore aggregate data received from the device and related to the device, the drug, and/or the patient for evaluation of the patient's condition and treatment and/or for evaluation of the efficacy of the device and/or the drug. The evaluation can be manually performed by a medical professional or can be automated by the remote computer system.

The identification of data as being associated with a particular patient does not necessarily require the identification of the full details of the patient. At a basic level identification of the data as associated with a particular patient can maintain the privacy of the patient so they cannot be uniquely identified but still allow the aggregation of multiple bits of data that are associated with one patient. This enables the collection of anonymous data that can be used for assessing correlations and trends associated with drug administration or other conditions encountered by the patients. This anonymous data can also be used in place of a control group as part of a clinical trial.

The computer system is configured to establish a unique key with each of a plurality of drug administration devices, drug housings, packagings, and/or sensors to allow the computer system to aggregate data from each of the different sources, thereby allowing for data analysis between different patients and/or data analysis between different devices/housings/packagings. Such analysis may be useful for any number of reasons, such as allowing for evaluation of treatments of different patients for optimal clinical outcomes, allowing for evaluation of patients' compliance with their individual medical treatment plans, and/or allowing an insurance company to more effectively correlate drug usage and drug cost.

The remembered link uses encryption to achieve secure, private, and anonymous data communication. In an exemplary implementation the computer system includes a server configured with a key-based security system, such as a public key/private key cryptographic system, to allow for data encryption and decryption. In an exemplary embodiment the server is a remotely located server relative to the drug administration device, housing, or other device in communication therewith. The server thus includes a memory, such as memory 897, and/or a database, such as additional storage 810, configured to store public and private keys for devices configured to communicate with the system. Public and private keys can be generated using cryptographic algorithms by the server. Keys can be used to encrypt data for transmission and to decrypt encrypted data received from a different computing device. In such systems, a public key associated with the intended receiver of the data can be utilized to encrypt data, however, only the recipient's private key can be used to decrypt the encrypted data. In at least some embodiments, the server includes a cryptographic system such as a public key infrastructure (PKI), in which one or more third parties, known as "certificate authorities," can certify ownership of the public and private key pairs. Examples of key-based security systems include the Diffie-Hellman key exchange protocol, the Digital Signature Standard (DSS) protocol, password-authenticated key agreement protocols, the Rivest-Shamir-Adelman (RSA) encryption algorithm, the Cramer-Shoup cryptosystem, and the YAK authenticated key agreement protocol.

More particularly, encryption is achieved with algorithms that use a key to encrypt and decrypt messages by turning text or other data into an unrecognizable digital form and then by restoring it to its original form. The longer the key, the more computing is required to crack the code. Computer keys are made of bits of information of various length. For example, an 8-bit key has 256 (2 to the eighth power) possible values. For another example, a 56-bit key creates 72 quadrillion possible combinations. If the key is 128 bits long, or the equivalent of a 16-character message on a personal computer, a brute-force attack would be 4.7 sextillion (4,700,000,000,000,000,000,000) times more difficult than cracking a 56-bit key. With encryption, unauthorized use of the data is generally prevented, even in the rare event that the data transmitted is intercepted by an unauthorized party.

A unique identification (ID) number or code is registered and stored in the device's memory, e.g., memory 97 of the device 500 of FIG. 5B, etc., such as during the manufacturing process before any use of the device. The ID number/code is unique to the device, although the ID number/code can include additional identifying information, such as a model or model family number or code, that is common to a plurality of devices and that may be useful in analyzing trends among a plurality of related devices. In an exemplary embodiment, the ID number is transmitted to the computer system with the drug administration device, drug, and/or sensor data to facilitate the computer system's identification of the data as coming from that particular device. The computer system can perform this identification in any number of ways, such as by looking up the ID number/code in a lookup table stored at the computer system that correlates ID numbers/codes of devices that may communicate with the device to particular keys so the computer system can identify which previously generated key to use to decrypt the data received from the device. The lookup table can also correlate the ID numbers/codes to particular devices and/or to particular patients associated with the particular devices. The ID number/code may not be encrypted in the data transmitted from the device to the computer system to allow the computer system to read the ID number/code and identify the correct key to use for decryption.

The key generated at the computer system for communication with a particular device, e.g., any of the drug administration devices of FIGS. 1-5B, any of the drug housings 30, 630 of FIGS. 5B and 6, the packaging 35 of FIG. 5B, etc., sensor, is shared with the device and stored at the device in a memory thereof, as discussed above. In some embodiments, instead of the computer system generating the key and transmitting the key to the device for storage at the device, the device can perform the key generation and transmit the key to the computer system for storage thereat. However, the remotely located computer system will typically have greater processing capability than the device, so in an exemplary embodiment key generation occurs at the remotely located computer system. In other embodiments, using certain key generation protocols that will be appreciated by a person skilled in the art, each of the computer system and the device participate in key generation such that a key is transmitted to one or the other of the computer system and the device, which may help improve security since avoiding key transmission prevents the key from being intercepted by an unauthorized party.

As mentioned above, the key stored at the drug administration device can uniquely identify the drug administration device and a patient associated with the drug administration device. In an exemplary embodiment, the drug administration device can store only one key. In such embodiments, only one patient is intended to use the drug administration device. In other exemplary embodiments, the drug administration devices can store a plurality of keys where each of the keys uniquely identifies the drug administration device and one of a plurality of patients associated with the drug administration device. In this way, the drug administration device can be used with each of the plurality of patients and be configured to transmit and receive data specific to only one of the patients based on which of the keys is used in transmitting and receiving data. A drug administration device may be used by multiple patients, for example, if a drug holder of the drug administration device is configured to be removed from the drug administration device after drug is delivered out of the drug holder and to be replaced by a second drug holder containing drug to be delivered from the drug administration device.

The data transmitted from the device to the computer system can include any of a variety of types of data. In an exemplary embodiment the data is indicative of sensed information gathered by one or more sensors configured to sense information relating to at least one of a drug administration device and a drug, such as any one or more of the device sensor 92, environment sensor 94, and location sensor 98 discussed above.

The data transmitted from a sensor to the computer system can include information relating to physiological parameters of the patient. The sensor may be configured to sense a physiological parameter that is one of: blood glucose level, blood oxygen level, body weight, or sleep duration. Further examples of physiological characteristics that can be sensed by sensors are blood pressure, perspiration level, respiratory rate, heart rate, core temperature, tremor detection, metabolic rate, inflammatory response. The physiological parameter may also include nutritional intake. Nutritional intake can be assessed by imaging food consumed by a patient. Alternatively, nutritional intake may be manually recorded by the patient.

The sensors described herein can be configured to gather data regarding a variety of conditions, such as device conditions (e.g., as sensed by the device sensor 92), environmental conditions (e.g., as sensed by the environment sensor 94), and location conditions (e.g., as sensed by the location sensor 98). Examples of conditions include geographic location (e.g., as sensed by a location sensor configured to sense GPS or other location), time (e.g., as sensed by a timer or a clock device such as an atomic clock), date (e.g., as sensed by a timer), temperature (e.g., as sensed by a temperature sensor), ultraviolet (UV) exposure (e.g., as sensed by a UV sensor configured to sense UV level), humidity (e.g., as sensed by a humidity sensor configured to sense humidity level), contact (e.g., as sensed by a contact sensor), and pressure (e.g., as sensed by a pressure sensor).

Using the universal drug administration device 500 of FIG. 5B and the computer system 700 of FIG. 7 by way of example, the drug administration device 500 can utilize the key-based security system to manage data storage and data transmission operations between the device 500 and the system 700. A key can be established between the device 500 and the computer system 700 using any of a variety of key establishment protocols. The key can be stored in the memory 97 of the device 500 and stored in a memory of the computer system 700 to allow the device 500 to encrypt data using the key and to transmit the encrypted data to the computer system 700 securely and in an anonymous manner that does not identify the device 500 or the patient associated therewith. The device's memory 97 can also store therein a unique ID number/code for the device 500. The device's processor 96 can be configured to use the key in encrypting data indicative of information sensed by any one or more of the device's sensors 92, 94, 98. The data can include metadata for the sensed information, such as time and date the data was collected. The device's processor 96 can be configured to cause the encrypted data to be transmitted wirelessly to the system 700 via the communications interface 99 of the device 500. The computer system 700 can then receive the data via its communications interface, identify from the received data the correct key stored in its memory to use in decrypting the received data, and then decrypt the received data using the identified, stored key. In this way, the computer system 700 can be configured to remove the anonymized aspect of the data to allow identification of the device 500 and the patient associated with the data since the key is previously known by the computer system 700 to be associated with that particular device 500 and patient. As noted elsewhere herein, the level of anonymity removal may maintain a degree of privacy of the patient when the precise identity of the patient is not required. Conversely, an unauthorized party that intercepts the data transmitted by the device 500 would not be able to remove the anonymized aspect of the data and, therefore, even in the event that interception occurs, the patient's privacy is maintained. The drug administration device 500 can utilize the generated key to encrypt all data that is transmitted from the device 500 to the system 700. The computer system 700 can also utilize the generated key stored thereat to encrypt any data transmitted therefrom to the device 500, with the device 500 able to decrypt that information using its stored key. Data transmitted from the system 700 to the device 500 can include, for example, a request for the device 500 to transmit sensed information to the system 700 in embodiments in which the device 500 is not configured to automatically transmit sensed information to the system 700, a request for the device 500 to begin drug delivery therefrom, a request for the device 500 to move from a locked state to an unlocked state (e.g., by moving the device operation prevention mechanism 40 or 25 of the device 500 from its locked state to its unlocked state, by changing at least one variable parameter of an algorithm stored on the device 500 to administer a drug dose to the patient from the device 500, etc.) to allow a user to manually cause drug delivery from the device 500, etc.

Figure 9:
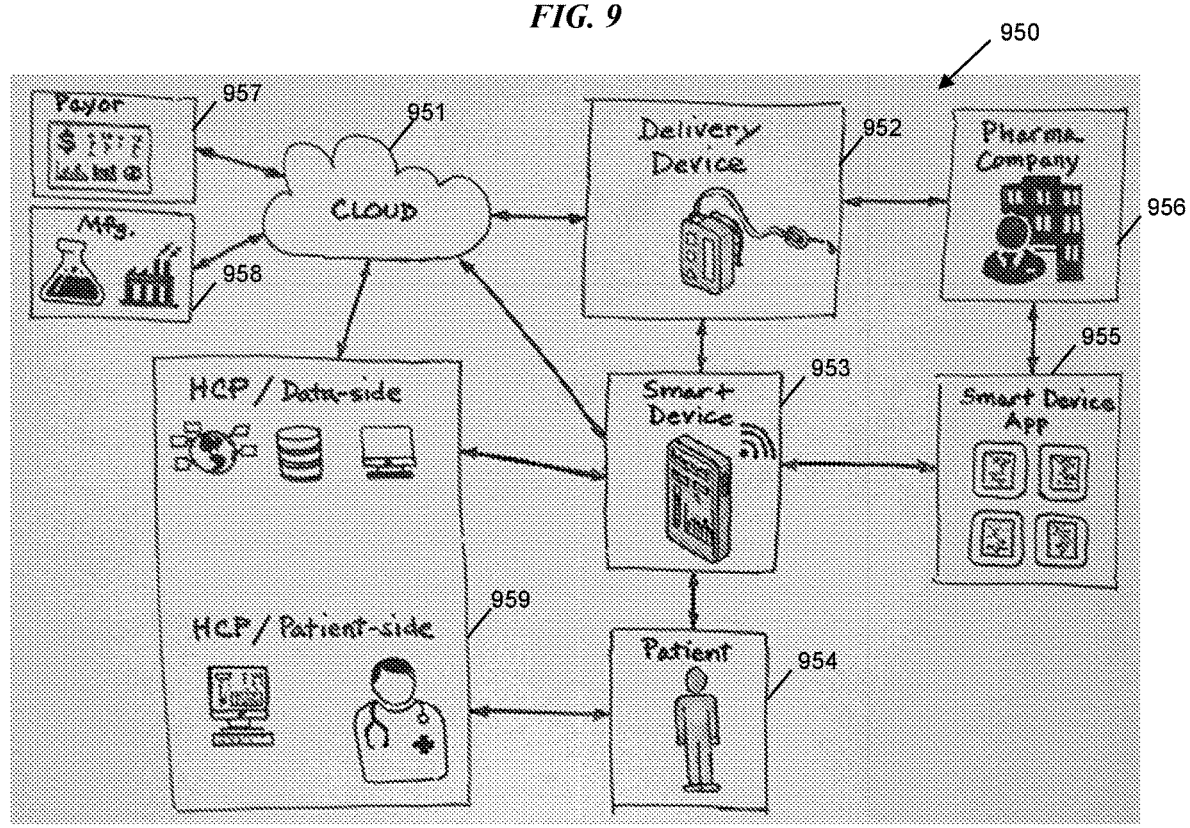
FIG. 9 is a schematic view of one embodiment of a drug administration system including a cloud computing system and a drug administration device.

FIG. 9 illustrates one embodiment of a drug administration system 950 including a cloud computing system 951 configured to communicate with one or more devices in a secure and anonymized manner using a key-based security system. The drug administration system 950 in this illustrated embodiment includes a drug administration device 952 configured to communicate with the cloud computing system 951 using a key-based security system, a smart mobile device 953 configured to communicate with the cloud computing system 951 and the drug administration device 952, a patient 954 configured to have a drug delivered thereto from the drug administration device 952 and to interact with the mobile smart device 953, one or more apps 955 installed on the smart device 953 and configured to facilitate the patient's interaction with the smart device 953 as related to the drug administration device 952, a pharmaceutical company computer system 956 for a pharmaceutical company associated with the drug and configured to communicate electronically with the one or more apps 955 (e.g., to provide software updates thereto, to push informational notifications thereto to provide to the patient 954, etc.) and with the drug administration device 952 (e.g., to push informational notifications thereto related to the drug to provide to the patient 954 via a user interface of the device 952, etc.), a payor database 957 configured to store payor data related to the patient 954 and to be accessible to the cloud computing system 951, a manufacturing database 958 configured to store drug data related to manufacturing of the drug and to be accessible to the cloud computing system 951, and a patient database 959 configured to store patient data related to the patient 954 and to be accessible to the cloud computing system 951, the patient 954, and the smart device 953. The patient database 959 includes data-side health care provider (HCP) data regarding the patient 954 that is configured to be accessible to the cloud computing system 951. The patient database 959 also includes patient-side HCP data regarding the patient 954 that is configured to be accessible to the patient 954, such as via the smart device 953 under patient control.

A key can be established between the drug administration device 952 and the cloud computing system 951 using any of a variety of key establishment protocols. The key can be stored in a memory of the device 952 and stored in a memory of the cloud computing system 951 to allow the device 952 to encrypt data using the key and to transmit the encrypted data to the system 951 securely and in an anonymous manner that does not identify the device 952 or the patient 954 associated therewith. The device's memory can also store therein a unique ID number/code for the device 952. The device's processor can be configured to use the key in encrypting data indicative of information sensed by any one or more of the device's one or more sensors. Alternatively, the device can be the sensor itself and so be configured to use the key in encrypting data indicative of information sensed. The data can include metadata for the sensed information, such as time and date the data was collected. The device's processor can be configured to cause the encrypted data to be transmitted wirelessly to the system 951 via the device's communications interface. The system 951 can then receive the data via its communications interface, identify from the received data the correct key stored in its memory to use in decrypting the received data, and then decrypt the received data using the identified, stored key. In this way, the system 951 can be configured to remove the anonymized aspect of the data to allow identification of the device 952 and the patient 954 associated with the data since the key is previously known by the system 951 to be associated with that particular device 952 and patient. Conversely, an unauthorized party that intercepts the data transmitted by the device 952 would not be able to remove the anonymized aspect of the data and, therefore, even in the event that interception occurs, the patient's privacy is maintained. The drug administration device 952 can utilize the generated key to encrypt all data that is transmitted from the device 952 to the system 951. The system 951 can also utilize the generated key stored thereat to encrypt any data transmitted therefrom to the device 952, with the device 952 being able to decrypt that information using its stored key. Data transmitted from the system 951 to the device 952 can include, for example, a request for the device 952 to transmit sensed information to the system 951 in embodiments in which the device 952 is not configured to automatically transmit sensed information to the system 951 or, for another example, a request for the device 952 to begin drug delivery therefrom to the patient 954 or, for yet another example, a request for the device 952 to move from a locked state to an unlocked state (e.g., by moving a device operation prevention mechanism of the device 952 from its locked state to its unlocked state, by changing at least one variable parameter of an algorithm stored on the device 952 to administer a drug dose to the patient 954 from the device 952, etc.) to allow a user to manually cause drug delivery from the device 952. In at least some embodiments, a key can be similarly established and used between the cloud computing system 951 and each of any one or more of the other computer systems 953, 957, 958, 959 in the system 950 with which the cloud computing system 951 is configured to communicate.

Figure 10:
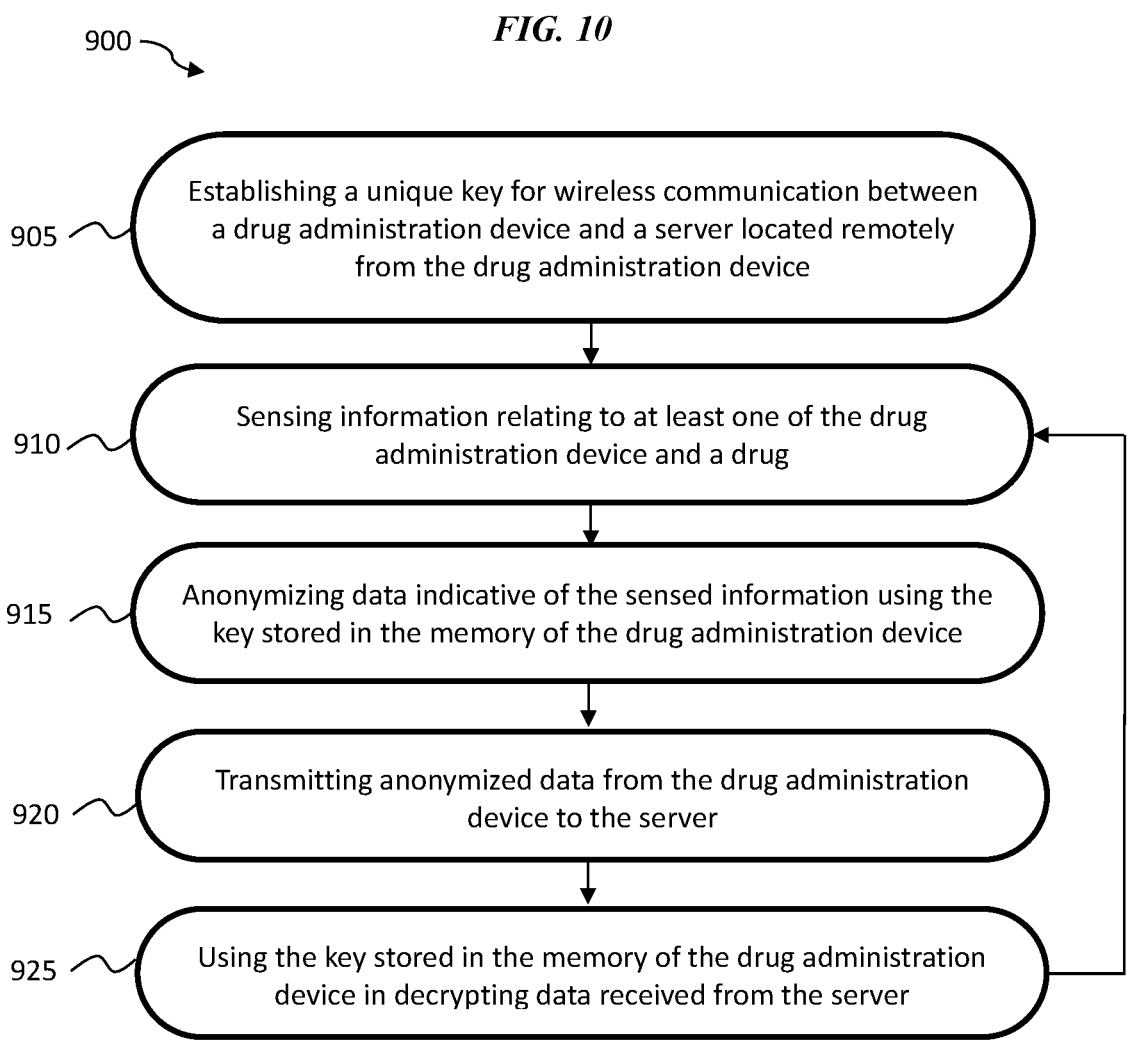
FIG. 10 is a flowchart illustrating one embodiment of a method for administering a drug using a key-based security system.

FIG. 10 is a flow diagram illustrating an exemplary embodiment of a method 900 using a key-based security system. The method 900 is described with respect to the drug administration devices 500 of FIG. 5B and the system 700 of FIG. 7 for ease of explanation, but other devices and systems, such as the sensor per se when not part of the drug administration device, can be similarly implemented as discussed above. The key-based system is used to encrypt and decrypt data that is transmitted and received between the drug administration device 500 and the system 700 so that data can be passed in a secure, private, anonymized manner.

In operation 905, the key-based security system establishes a unique key for wireless communications between the drug administration device 500 and the system 700 located remotely from the device 500. In at least some embodiments, a server configured within the system 700 implements the key-based security system. The unique key is stored in a memory of the remotely located server, as well as in an additional storage that may be configured with the system 700. The system 700 can transmit the key to the device 500 for storage in the memory 97 thereof, or, as discussed above, the device 500 can be configured to generate its own key of a key pair to be used in the key-based security system.

In operation 910, the drug administration device 500 senses using one or more of the sensors 92, 94, 98 information relating to at least one of the drug administration device 500 and the drug to be dispensed therefrom. The sensed information can include, for example, data associated with the dosage amounts and the delivery schedule of the drug to be administered via the drug administration device 500.

In operation 915, the processor 96 of the drug administration device 500 uses the generated key stored in the memory 97 to encrypt and anonymize data indicative of the sensed information. The processor 96 anonymizes and encrypts the data prior to transmission, in operation 920, of the data to the remotely located computer system 700 such that when transmitted, the data is transmitted in a secure, encrypted manner. The transmission in operation 920 also includes the device's unique ID number/code to facilitate the computer system's decryption of the data received from the device 500.

In operation 925, if the drug administration device 500 receives encrypted data from the system 700, the drug administration device 500 uses the key stored in memory 97 to decrypt the data that is received.

In relation to a sensor being configured to sense information relating to a physiological parameter of a patient, the sensor can be configured to obtain information relating to the physiological parameter on a regular basis, e.g., at least once every 24 hours, once every 12 hours, once every three hours, once every hour, once every 30 minutes or once every 10 minutes, etc. This can be chosen in line with the frequency of data required. This data can then be communicated anonymously to a server, as described herein, at a corresponding frequency or a lower frequency as required. The sensor may therefore enable the collection of data in an anonymous manner such that is can be utilized without risk of identifying the original patient and thus assist with patient acceptance relating to the collection of their data.

A single patient may have a plurality of sensors for measuring different parameters, which may be further physiological parameters. These sensors may all be associated with the same patient within the system allowing the aggregation of data on the server in relation to this patient.

Data associated with a single patient, beyond the physiological information obtained by the sensor, may also be obtained. For example, a drug administration device associated with the patient may also communicate data relating to the patient, as described herein, and be aggregated with the physiological information on the server to give an indication of physiological response to certain drug administration device performance.

A plurality of patients may each have at least one sensor for measuring a physiological parameter. The sensors are each associated with their respective patient within the system allowing the storing of data for each patient. This allows the collection of many data points across a range of patients which can assist in finding trends and correlations. In particular, each of the plurality of patients may have a plurality of sensors contributing to more data points assisting further analysis of observed outcomes. Each of the plurality of patients may have a drug administration device associated with them providing further data to the server.

In one embodiment of operation, the sensor configured to sense information relating to a physiological parameter of a patient senses a physiological parameter.

In the next steps, the sensor uses a key to anonymize the data indicative of the sensed physiological parameters and wirelessly transmits the data indicative of the sensed physiological parameter to a remotely located communications interface. This is repeated at a periodic rate of, for example, once every 24 hours. The periodic measurement may be repeated for a duration of at least 24 hours such as 48 hours; 7 days; 14 days; 30 days; 90 days; 120 days; 180 days; 365 days, etc. In this way, it is possible to complete short term tests over hours and days, but also accumulate more data over a longer period of time to enable highly accurate testing. For example, where the monitored physiological parameters comprise blood glucose level and nutritional intake such as carbohydrate intake and body weight, the steps can be repeated for duration of 365 days to provide a highly accurate long term glucose test that would be otherwise unachievable using traditional methods. This could better inform real world treatment algorithms.

When a single patient has first and second sensors each configured to sense a physiological parameter, the first sensor can be configured to sense the blood glucose level of the patient and the second sensor can be configured to sense nutritional intake, e.g., one or more of carbohydrate, protein and fat intake. Monitoring these parameters can be achieved using various sensors, such as a patient sensor 92 as described elsewhere herein. Thus, a glucose test can be created each time a patient eats so a method of glucose tolerance testing is provided that is more convenient and less time consuming than traditional approaches.

Figure 15:
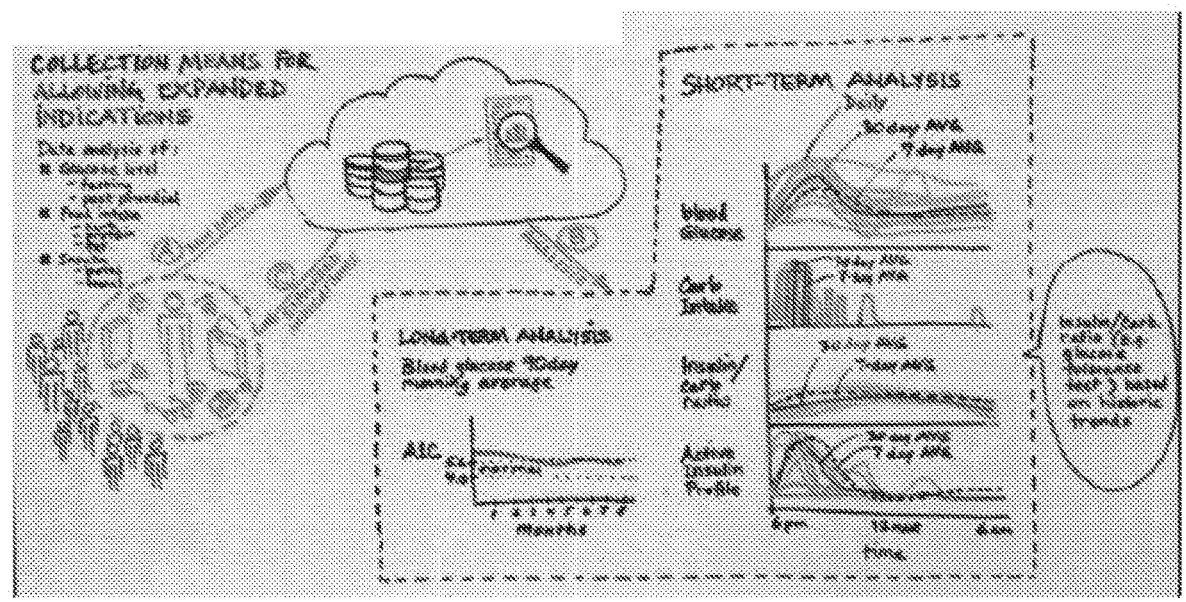
FIG. 15 is a schematic view of one embodiment of a system utilizing a sensor.

FIG. 15 shows one embodiment of a system that accumulates data associated with one patient of a plurality of patients. The system can identify that one patient and so extract recorded data associated with this patient. In this embodiment, the extracted data are blood glucose, carbohydrate intake, and patient response to insulin administration. These data can be analyzed to provide a ratio of response to insulin administration/carb ratio over a 30 day average and a 7 day average in the short term. The sensed data also provide an average blood glucose level over a 90 day average for long term analysis. The ability to extract such data can allow trends to be established for individual patient circumstances. Such patient data can be combined with patients of a similar situation to build up a picture of trends across any particular part of the population. This can benefit optimization of dosing schemes for new patients who do not have any historical data.

Sensor data (and/or other data) received regarding a particular patient can be automatically uploaded into the patient's electronic health record (EHR) and/or into a form required for use with a particular drug such as a patient monitoring form for a particular drug's Risk Evaluation and Mitigation Strategies (REMS), e.g., a REMS for esketamine, ketamine, or other controlled substance. The EHR and/or form may therefore be accurately and timely updated.

Figure 16:
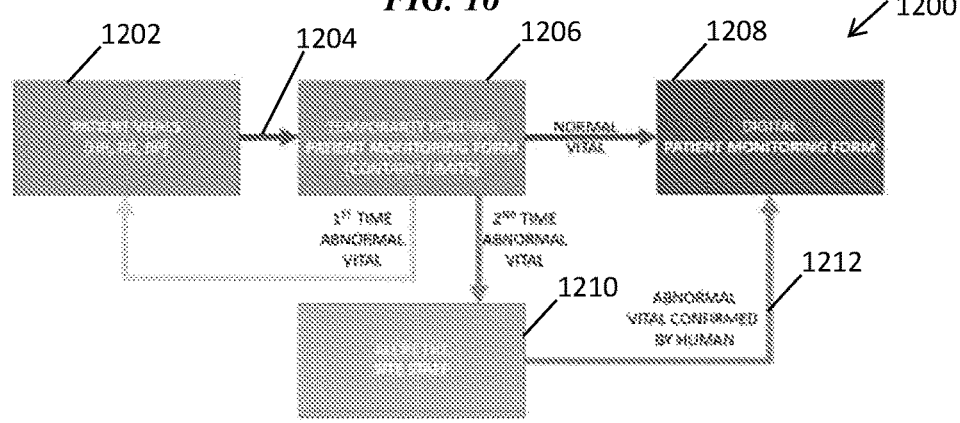
FIG. 16 is a flowchart showing one embodiment of a method of updating a patient monitoring form and identifying one or more abnormal sensed parameters.

FIG. 16 illustrates one embodiment of a method 1200 of updating a patient monitoring form with data sensed by one or more sensors regarding a particular patient. The patient monitoring form can be similarly updated with other data, such as data input to a drug administration device's user interface and communicated to a remote computer system such as the central computer system 700. For example, psychological condition data can be gathered in a variety of ways, such as via patient answers to questions in a questionnaire that are stored at an external device, through user input to one or more questions presented via a drug administration device's user interface such as answers to a psychological stress test such as the Kessler Psychological Distress Scale (K10) or any of a variety of other indices and scales, health care provider assessment notes regarding the patient that are stored at the external device, etc. Psychological condition data can be used, e.g., by a processor, to assess when the drug should be delivered to the user from the drug administration device 500 and to determine how the user is reacting to the current treatment. For example, a trend in improving mental state may be indicative of effective drug treatment for depression such that drug dosage and/or drug dosing frequency may be reduced. For another example, a trend in declining mental state or a static trend in mental state may be indicative that drug dosage and/or drug dosing frequency should be increased for a drug treating depression.

In this illustrated embodiment the sensed parameters include patient heart rate (HR), patient respiratory rate (RR), and patient blood pressure (BP), but as discussed herein, other conditions can be sensed. The one or more sensors gather 1202 data, and the drug administration device 500 communicates 1204 the sensed data to the computer system 700 (or other device as discussed herein). The computer system 700 populates 1206 the received sensed data into a temporary holding patient monitoring form. For each of the sensed parameters, the computer system 700 determines if the sensed data is above a predetermined maximum threshold value or below a predetermined minimum threshold value, as appropriate for the particular condition being measured. If not, the sensed data is considered to be normal, e.g., within acceptable limits, and the computer system 700 populates 1208 the patient monitoring form with the sensed data for that sensed condition. If so, the sensed data is considered to be abnormal, e.g., not within acceptable limits. The computer system 700 determines whether this determination of abnormality is the first determination of abnormality for this sensed parameter for this patient. If this determination of abnormality is the first determination of abnormality for this sensed parameter for this patient, the patient monitoring form is not yet populated 1208 with the sensed data. Instead, after the parameter is sensed 1202 again, the computer system 700 receives the sensed parameter data and populates 1206 the received sensed data into the temporary holding patient monitoring form. If the computer system 700 determines that this sensed data is above the predetermined maximum threshold value or below the predetermined minimum threshold value, as appropriate for the particular condition being measured, so as to be the second instance of abnormal sensed data for this sensed condition, the computer system 700 causes 1210 an alert to be provided to medical personnel, e.g., staff on site with the patient using the drug administration device 500, the patient's medical care provider, etc., for evaluation and possible intervention. The alerted medical personnel confirms 1212 the abnormal sensed data, e.g., by manually reviewing the data on a display screen of the computer system 700, and cause the patient monitoring form to be populated 1208 with the sensed data, e.g., by providing an input to a user interface of the computer system 700 that triggers the populating 1208. The human review of sensed data and confirmation of abnormal sensed data by medical personnel may help allow for insurance reimbursement since human activity is involved. If the computer system 700 determines that this sensed data is not above the predetermined maximum threshold value or below the predetermined minimum threshold value, as appropriate for the particular condition being measured, the first abnormal determination is considered to be an anomaly, and the computer system 700 populates 1208 the patient monitoring form with the sensed data for that sensed condition.

In other embodiments of the method 1200, the temporary holding patient monitoring form can be eliminated. In such embodiments, the patient monitoring form will be populated 1208 with all sensed data, even sensed data that is determined for the first time to be abnormal, which may provide for a more complete patient record.

In other embodiments of the method 1200, medical personnel can be alerted to the first abnormal sensed condition, which may help allow medical intervention to be provided more quickly in the case of an emergency.

In at least some implementations, data communicated in a secure and anonymized manner from a device, such as any of the drug administration devices of FIGS. 1-5B, any of the drug housings 30, 630 of FIGS. 5B and 6, the packaging 35 of FIG. 5B, sensors, etc., to a remote computer system, such as central computer system 700 of FIG. 7, can be used to alter drug delivery. The remote computer system using data received in a secure, anonymized manner as discussed above to alter drug delivery may help ensure that drug delivery from a device is altered based on information verified as being associated with the device since the remote computer system can only decrypt the data if the remote computer system can identify and has the proper key for decryption. In other words, the data is self-verifying for use in drug delivery alteration since the remote computer system can only read and use the received data to alter drug delivery if the remote computer system and the device have previously established a secure, anonymized communication protocol. Data used to alter drug delivery can, however, be transmitted from the device to the remote computer system in a way other than the secure, anonymized communication implementations discussed above.

When delivering drugs, a variety of factors can influence drug administration, absorption, and effect on a patient beyond simply the initial drug dose itself. For example, individual patient physiologies or statuses, physiological effects on a patient of drug administration, surrounding external conditions to the patient, etc. can all influence results of drug administration on a patient. It can thus be beneficial to a patient to allow drug delivery to be adjusted based on a variety of different factors that arise during use of drug administration devices, providing more personalized treatment while also helping a patient receive and/or a doctor deliver specialized care for the specific patient being treated. Additionally, being able to automate as much of the drug delivery adjustment can help ease the process of delivery for both the patient and the doctor while improving patient outcomes.

In an exemplary embodiment, drug delivery can be altered based on an instruction from a remote computer system. An algorithm stored on a drug administration device, e.g., in a memory thereof, is executable on board the device, e.g., by a processor thereof, to administer a dose of a drug to a patient. The algorithm is stored in the form of one or more sets of pluralities of data points defining and/or representing instructions, notifications, signals, etc. to control functions of the device and administration of the drug. Data received by the drug administration device, e.g., as pluralities of data points via a communications interface thereof, is used, e.g., by the device's processor, to change at least one variable parameter of the algorithm. The at least one variable parameter is among the algorithm's data points, e.g., are included in instructions for drug delivery, and are thus each able to be changed by changing one or more of the stored pluralities of data points of the algorithm. After the at least one variable parameter has been changed, subsequent execution of the algorithm administers another dose of the drug according to the changed algorithm. As such, drug delivery over time can be remotely managed for a patient, e.g., by a medical professional providing input for the drug delivery change to the computer system, to increase the beneficial results of the drug. Changing the at least one variable parameter and/or administration of the one or more doses themselves is automated to improve patient outcomes. Thus, the drug administration device can be configured to provide personalized medicine based on the patient to provide a smart system for drug delivery.

It is typically less expensive and/or easier to upgrade the remote computer system than for the patient to upgrade their drug administration device or acquire a new drug administration device, so offloading processing and variable parameter control to the remote computer system may extend the useful life of the drug administration device and/or may allow for a single upgrade to be made (to the remote computer system) instead of multiple upgrades having to be made (to each of the drug administration devices in communication with the remote computer system).

In an exemplary embodiment, the data on which the device's algorithm is modified includes at least data gathered by at least one sensor configured to gather data regarding a characteristic associated with the drug administration device and/or the drug deliverable therefrom. The drug administration device may therefore utilize local processing to customize the delivery of the drug based on information sensed by the device and, in at least some embodiments, based on one or more additional factors such as historical drug delivery and dosage data compiled by the computer system. When the device includes two or more sensors, each of the sensors is, in an exemplary embodiment, configured to gather data regarding a different characteristic to help improve customization of the algorithm by taking multiple factors into account.

Examples of sensors that can sense data used to modify an algorithm are the sensors 92, 94, 98 discussed above. Examples of characteristics that can be sensed by sensors and used to modify an algorithm are physiological characteristics of the patient, physical characteristics of the patient, and situational characteristics of the patient. Any of various different physiological characteristics can be monitored, such as blood sugar level (e.g., using a glucose monitor, etc.), blood pressure (e.g., using a blood pressure monitor, etc.), perspiration level (e.g., using a fluid sensor, etc.), respiratory rate (e.g., using a respiratory monitor, a heat sensor configured to be located near a nose or mouth and to use heat detection on the out-breath or detect in/out airflow movement, a pressure sensor configured to be located near a nose or mouth and to use pressure detection on the out-breath or detect in/out airflow movement, a spirometer, etc.), heart rate (e.g., using a heart rate monitor, etc.), etc. Any number of different situational characteristics can be monitored, such as core temperature (e.g., using a temperature sensor), tremor detection (using an accelerometer, etc.), fall detection (using an accelerometer, etc.), irregular gait detection (using an accelerometer, etc.), time of day (e.g., using a timer, etc.), date (e.g., using a timer, etc.), patient activity level (e.g., using a motion sensor, etc.), blood pressure (e.g., using a blood pressure monitor, etc.), metabolic rate (e.g., using heart rate as discussed herein, etc.), altitude (e.g., using an altimeter, etc.), temperature of the drug (e.g., using a temperature sensor), viscosity of the drug (e.g., using a viscometer, etc.), GPS information (e.g., using a location sensor, etc.), weather information (e.g., using a temperature sensor, humidity sensor, etc.), room or external temperature (e.g., using a temperature sensor), angular rate (e.g., using an inertial measurement unit (IMU) or MARG (magnetic, angular rate, and gravity) sensor), body orientation (e.g., using an IU, etc.), current of a motor used in delivering the drug (e.g., using a current sensor), blood oxygenation level (e.g., using a blood oxygen sensor), sun exposure (e.g., using a UV sensor, etc.), osmolality (e.g., using a blood monitor, etc.), air quality (e.g., using a UV sensor, etc.), inflammatory response, one or more images and/or videos of the patient and/or an environment in which the patient is located (for example, to analyze food intake; to determine whether solid food or liquid is being consumed; to determine a location or activity of the patient, to determine a condition of the patient such as skin reaction, breathing, eye dilation, sedation, disassociation, voice characteristics such as tone and pitch; etc.), user-input data such as general well-being, pain score, or a cycle time between flare ups of a particular ailment, etc. Any of various different physical characteristics can be monitored, such as temperature, metabolic demand, cognitive function, atmospheric contaminant percentage, metabolic demand such as measured using at least one of food intake and BMR (basal metabolic rate), weight, one or more images and/or videos of the patient and/or an environment in which the patient is located (for example, to analyze food intake, to determine whether solid food or liquid is being consumed, to determine a location or activity of the patient, to determine a condition of the patient such as skin reaction, etc.), etc. U.S. Patent Pub. No. 2011/0295337 entitled "Systems and Methods For Regulating Metabolic Hormone Producing Tissue" published Dec. 1, 2011, U.S. Pat. No. 8,696,616 entitled "Obesity Therapy And Heart Rate Variability" issued Apr. 15, 2014, U.S. Pat. No. 9,427,580 entitled "Devices And Methods For The Treatment Of Metabolic Disorders" issued Aug. 30, 2016, and U.S. Pat. No. 9,168,000 entitled "Meal Detection Devices And Methods" Oct. 27, 2015, which are incorporated by reference herein in their entireties, further describe identifying types of information about a meal and/or a drink. In various embodiments, a sensor includes an image capturing device such as a camera, and a processor is configured to analyze image(s) and/or video(s) captured by the image capturing device, such as to analyze any food intake and/or determine one or more side effects such as patient skin reaction to the drug, patient sedation level, patient disassociation level, vomiting, etc. Facial ID can be used to identify the patient in image(s) captures by the sensor including a camera to help ensure that relevant data is being gathered and analyzed. U.S. Patent Pub. No. 2012/0330684 entitled "Medication Verification And Dispensing" published Dec. 27, 2012, which is incorporated by reference herein in its entirety, further describes image capturing devices. U.S. Patent Pub. No. 2002/0014951 entitled "Remote Control For A Hospital Bed" published Feb. 7, 2002, and U.S. Patent Pub. No. 2007/0251835 entitled "Subnetwork Synchronization And Variable Transmit Synchronization Techniques For A Wireless Medical Device Network" published Nov. 1, 2007, further discuss various sensors and are incorporated by reference herein in their entireties.

Using the universal drug administration device 500 of FIG. 5B and the computer system 700 of FIG. 7 by way of example, the memory 97 of the device 500 can have stored therein an algorithm, and the device's processor 96 can be configured to execute the algorithm to control delivery of a dose of the drug dispensed by the device's dispensing mechanism 20. The device's communications interface 99 can be configured to receive an instruction from a communications interface of the remote computer system 700 requesting a change to at least one variable parameter of the stored algorithm. In response to the instruction, the device's processor 96 can be configured to change at least one variable parameter of the algorithm as requested such that a dose delivered subsequent to the changing of the at least one variable parameter will be controlled by execution of the changed algorithm.

Figure 11:
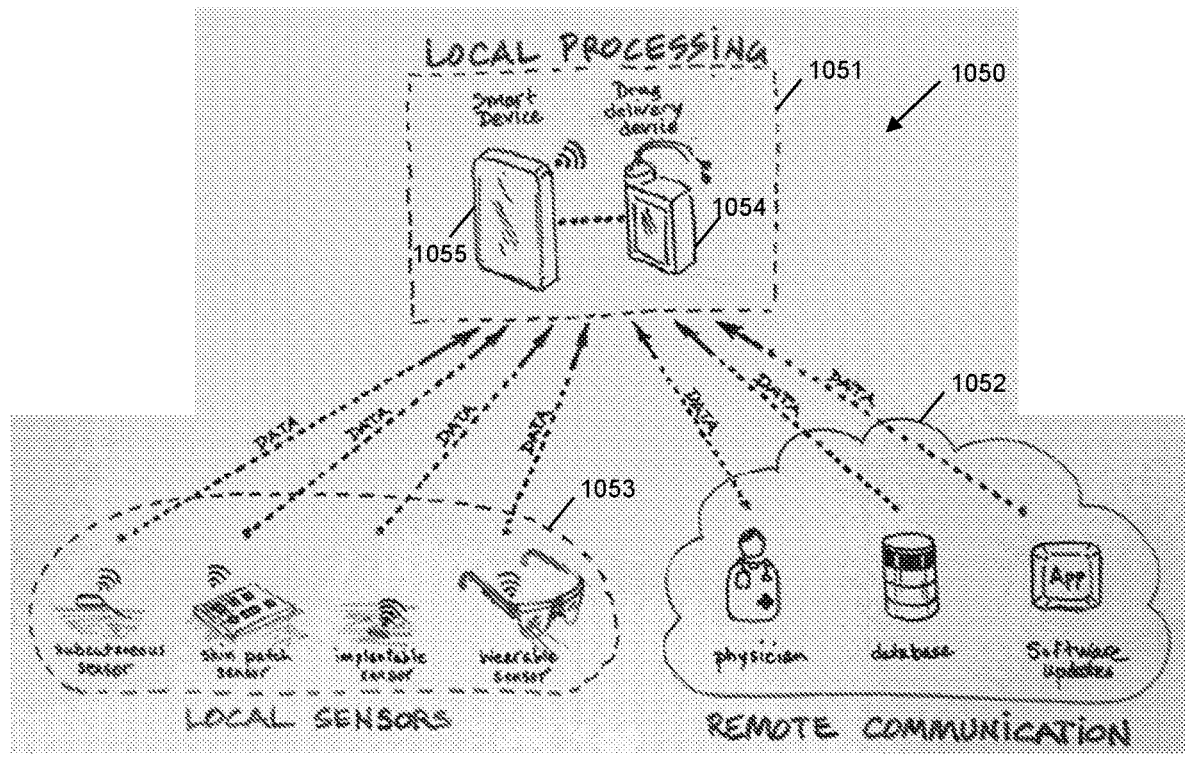
FIG. 11 is a schematic view of one embodiment of a drug administration system including a drug administration device and a remote computer system.

FIG. 11 illustrates one embodiment of a drug administration system 1050 including a local processing system 1051, a remotely located computer system 1052 (remotely located relative to the local processing system 1051) configured to communicate with the local processing system 1051, and local sensors 1053 (local to a patient associated with the local processing system 1051) each configured to communicate with the local processing system 1051.

The local processing system 1051 includes a drug administration device 1054 and a mobile smart device 1055 configured to electronically communicate with the drug administration device 1054. A memory of the device 1054 can have stored therein an algorithm, and the device's processor can be configured to execute the algorithm to control delivery of a dose of the drug dispensed by the device's dispensing mechanism. The device's communications interface can be configured to receive an instruction from a communications interface of the remote computer system 1052 requesting a change to at least one variable parameter of the stored algorithm. In response to the instruction, the device's processor can be configured to change at least one variable parameter of the algorithm as requested such that a dose delivered subsequent to the changing of the at least one variable parameter will be controlled by execution of the changed algorithm. Alternatively, a memory of the smart device 1055 can have the algorithm stored therein, with the remote computer system 1052 instead communicating with the smart device 1055 to control updating of the algorithm, and can be configured to execute the algorithm and thereby cause a command for drug delivery to be provided to the drug administration device 1054.

The smart device 1055 and/or the drug administration device 1054 can be configured to receive data from the sensors 1053 and show information related thereto on a user interface thereof. In this illustrated embodiment, the sensors 1053 include a subcutaneous sensor, a skin patch sensor, an implantable sensor, and a wearable sensor. The received sensor data can be transmitted to the remote system 1052 for analysis that can trigger updating of the algorithm, as discussed herein. The smart device 1055 and/or the drug administration device 1054 can each include one or more on-board sensors in addition to, or in alternative to, any or all the off-board sensors 1053. The on-board sensor data can be transmitted to the remote system 1052 for analysis that can trigger updating of the algorithm, as discussed herein.

Figure 12:
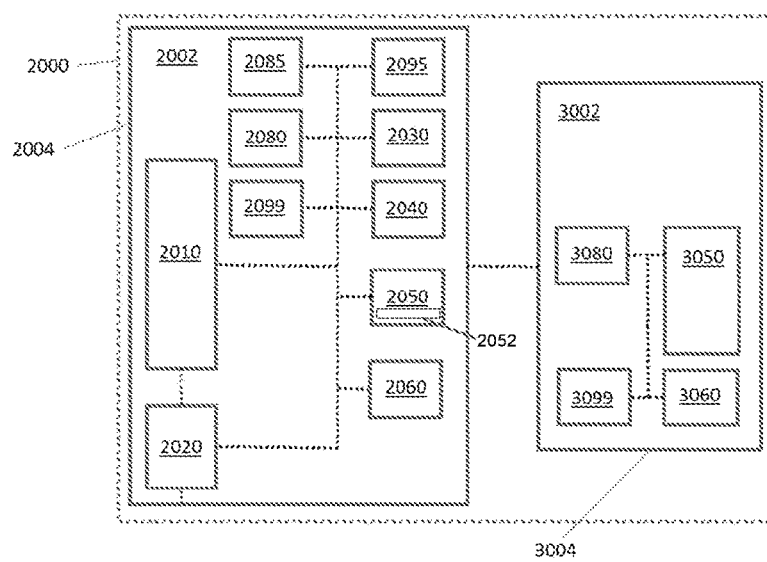
FIG. 12 is a schematic view of another embodiment of a drug administration system including a drug administration device and a remote computer system.

FIG. 12 illustrates another embodiment of a drug administration system 2000 including a universal drug administration device 2002 and a remotely located computer system 3002 configured to communicate with one another. The drug administration device 2002 in this illustrated embodiment includes a housing 2004, a drug holder 2010, a dispensing mechanism 2020, at least one sensor 2030, 2040, a memory 2050 configured to store an algorithm 2052 therein, a processor 2060, a user interface 2080, an indicator 2085, a power supply 2095, and a communications interface 2099. The computer system 3002 in this illustrated embodiment includes a server 3004, a memory 3050, a user interface 3080, a processor 3060, and a communications interface 3099. Additionally, similar to that mentioned above regarding the universal drug administration device 500 of FIG. 5B, a person skilled in the art will appreciate that the universal drug administration device 2000 of FIG. 12 comprising the drug holder 2010, dispensing mechanism 2020, processor 2060, memory 2050, and sensors 2030, 2040 can be provided with a variety of the features described above, in a number of different combinations. For example, the device 2000 may include at least two sensors but not all of the sensors 2030, 2040, 2045, may not have a user interface 2080, etc. While the sensors 2030, 2040 are each included with the device 2000 in this illustrated embodiment, one or more of the sensors 2030, 2040 can be separate from the device 2000 by, e.g., being worn on the patient, being placed in a shared geographical space with the patient, being attached to other equipment or instruments, being part of a mobile phone app used by the patient, etc.

The memory 2050 is configured to store data from the sensors 2030, 2040, however in other embodiments this data can be stored elsewhere, such as in another memory on board the device 2000 and/or in a remote memory accessible to the device 2000 via the communications interface 2099. The algorithm 2052 stored in the memory 2050 represents instructions for the device 2000 regarding how to administer the drug in the drug holder 2010 and is configured to be executed by the processor 2060. The algorithm 2052 is stored in the form of a plurality of data points defining and/or representing instructions, notifications, signals, etc. to control drug administration, with the at least one variable parameter being among the data points such that changing the at least one variable parameter of the algorithm 2052 results in at least one change in how the drug is administered. The at least one variable parameter can be any of a variety of different delivery and/or drug parameters. Examples of variable parameters include a rate of delivery of the drug from the drug holder 2010 to the patient, a time interval between dose deliveries such that doses delivered after the at least one variable parameter is changed are at a different time interval than doses delivered before the change, a dosage amount, a dosage concentration, whether or not any additional doses are delivered such as stopping a second or any subsequent dose or starting to dose again after dosing was previously stopped before a first dose or before any subsequent dose after the first dose, a rate at which a needle of the device is automatically advanced into the patient, a temperature of the drug, etc. The rate at which a needle of the device is automatically advanced into the patient may be important to adjust because the rate being too slow may prevent the needle from penetrating into the patient at all or to its intended depth for effective drug delivery, and the rate being too fast may cause the patient discomfort.

The processor 2060 of the device 2002 is configured to execute the algorithm 2052 to control administration of one or more doses of the drug to the patient. In an exemplary embodiment, the processor 2060 executes the algorithm 2052 to control delivery of at least a first dose of the drug to the patient, changes the at least one variable parameter of the algorithm 2052 in response to an instruction from the remote system 3002, and executes the algorithm 2052 after changing the at least one variable parameter to control delivery of at least one subsequent dose of the drug. In some embodiments, the processor 2060 can change the at least one variable parameter of the algorithm 2052 before execution of the algorithm 2052 to control delivery of the first dose, such as by changing a variable parameter from indicating that dosing was stopped (e.g., because the drug administration device's device operation prevention mechanism is in a state to prevent drug delivery, the drug administration device's power supply lacks sufficient power to deliver a dose, etc.) to indicating that dosing is allowed (e.g., the drug administration device's device operation prevention mechanism is in a state to allow drug delivery, the drug administration device's power supply has sufficient power to deliver a dose, etc.). To execute the algorithm 2052, the processor 2060 is configured to run a program stored in the memory 2050 to access the plurality of data points of the algorithm 2052 in the memory 2050. To change the at least one variable parameter of the algorithm 2052, the processor 2060 is configured to modify or update the data point(s) of the at least one variable parameter in the memory 2050. The processor 2060 can also be configured to execute instructions stored in the memory 2050 to control the device 2000 generally, including other electrical components thereof such as the communications interface 2099, indicator 2085, and user interface 2080.

The processor 2060 can be configured to automatically control delivery of doses of the drug based on one or more predetermined schedules or intervals of dosing for the patient, which can be predetermined prior to an initial dose or can be determined during use of the device 2000 after delivery of the first dose and set such that future doses can be based on the predetermined schedule(s). The predetermined schedule(s) can also be determined by a doctor or other care provider, created automatically based on the algorithm 2052 and/or the sensors 2030, 2040 being used, or some combination of the two. In at least some embodiments, the at least one variable parameter includes a timing between doses, and the instruction to change the variable parameter for a timing between doses can be changed based on a new drug delivery schedule input to the system 3002 by an appropriate medical professional after noticing a decline in a particular clinical outcome of the patient as reflected in data that is received by the system 3002 from the device 2000.

In some instances, a drug administration device may malfunction and not properly deliver a dose despite the device being actuated to deliver the dose. In some instances, a drug administration device may be accidentally actuated, such as by an inhaler being caused to deliver drug before the inhaler is inserted into a patient's mouth or a nasal spray device being caused to deliver drug through its nozzle before the nozzle is inserted into a nostril of a patient. In such instances of device malfunction and/or accidental actuation, the patient may not have received the prescribed amount of drug even though the drug administration device has been actuated at least once to deliver the prescribed amount of drug. It may therefore be beneficial to increase the maximum number of allowable doses, e.g., from one to two, from two to three, from two to four, from three to four, from four to five, from four to six, etc., to allow for the prescribed amount of drug to actually be delivered to the patient. An instruction to change the variable parameter for the maximum number of allowable doses (and/or other variable parameter, such as timing between doses, a locked/unlocked state of the device, dose amount, etc.) can be changed based on an input to the system 3002 by an appropriate medical professional after receiving notification of a need for at least one additional device actuation due to a device malfunction or accidental actuation. The medical professional can receive the notification in any of a variety of ways, such as by being present with the patient when the device malfunction or accidental actuation occurs, by receiving a communication from the patient such as a text message, email, phone call, etc., or other notification mechanism. In an exemplary embodiment, the algorithm can be changed to increase the number of additional allowable device actuations by only one. In other embodiments, the number of additional allowable device actuations can be greater than one. However, limiting additional dose deliveries to one may help prevent drug abuse and/or may allow for more health care professional intervention with the user, e.g., to assess whether additional training is needed if more than one accidental actuation is input as having occurred before the additional dose(s) are authorized, to assess whether device malfunction requires a new device instead of additional dose(s) from the device that malfunctioned, etc.

The processor 3060 of the remote system 3002 is configured to receive and analyze data indicative of information gathered by the drug administration device's one or more sensors 2030, 2040, and, based on the analysis, transmit an instruction to the device 2002 to change at least one variable parameter of the algorithm 2052. The processor 3060 is configured to control drug delivery from the device 2002 through any of a variety of different mechanisms, such as by transmitting a command to the device 2002 using the communications interfaces 2099, 3099 with the device's processor 2060 executing the command to cause drug delivery (e.g., by providing a plurality of data points defining one or more instructions to the device 2002).

Because the algorithm is configured to be altered based on data gathered by one or more of the sensors 2030, 2040, an automated reaction response based on the situational awareness of the patient is possible. In at least some embodiments, the at least one variable parameter is altered to provide adaptive dose adjustment based on various readings and/or data from one or more of the sensors 2030, 2040. For example, a user of the device 2000 can record a cycle time between flare ups of a disease or ailment, at which point the drug dosing schedule as reflected in the algorithm 2052 can be adjusted after analysis by the remote processor 3060 to take this into account for better disease control.

As another example, changes in altitude of a patient can potentially alter the effectiveness of medications and even lead to toxicity in some cases. As such, the duration at which a patient is at a different altitude can be read by one or more of the sensors 2030, 2040 and be used by the remote processor 3060 to adjust subsequent drug dosages by causing the local processor 2060 to change the at least one variable parameter.

In another example, the remote computer system 3002 can be configured to cause a treatment to be discontinued entirely based on one or more sensor readings, and, in at least some embodiments, a patient can be informed as such through the device indicator 2085 and/or user interface 2080. By way of example, glucose levels can lower significantly, activity level can begin to increase, blood pressure can dip, perspiration can increase dramatically, a poor REM cycle of sleep can be detected by a sleep quality sensor, and possible tremors can be detected by a tremor detection sensor. These measured characteristics can be analyzed by the remote processor 3060, which can identify each indicator as being consistent with hypoglycemia, and thus instruct the device 2002, which in this example is an insulin pump configured to deliver insulin, to terminate insulin delivery by changing the at least one variable parameter to reflect no doses, e.g. by changing dose amount to zero or by changing dose frequency to a never-achievable time period. Because dosing is terminated promptly at the beginning of the possible hypoglycemic event rather than waiting until glucose level falls below a normal or safe threshold and only then reacting, the glucose level in the patient can begin to rise again quickly, entering a healthier or normal range and then returning to an ideal range. Embodiments of insulin pumps are further described in U.S. Patent Pub. No. 2009/0069787 entitled "Activity Sensing Techniques for an Infusion Pump System" filed on Sep. 7, 2007 and incorporated herein by reference in its entirety.

For another example, changing the at least one variable parameter can result in an adjusted injection or flow rate speed of each provided dose, e.g., the at least one variable parameter can include injection or flow rate speed. For yet another example, a temperature of a drug can be varied to create constant flow, as discussed in U.S. Patent Pub. No. 2002/0042596 entitled "Method And Apparatus To Sense Temperature In An Implantable Pump" published Apr. 11, 2002 and hereby incorporated by reference in its entirety.

For another example, the system 3002, e.g., the processor 3060 thereof, can analyze data received from the device 2000, such as physiological characteristic data and/or physical characteristic data, and determine that a patient is administering a drug too frequently and thereby creating a risk for a negative side-effect or possibly, an overdose.

The remote system 3002 can be configured to cause updating of the algorithm 2052 in response to receiving data for a specific period of continuous monitoring of a sensed variable, for example, a patient's blood sugar levels as sensed using, e.g., a glucose monitor. For example, with the device 2002 being configured to administer insulin to the patient, the algorithm 2052 can be updated in response to monitoring a patient's blood sugar levels for an hour, a day, a week, a month, etc. The blood sugar level data can be utilized by the system 3002 to determine a modified version of the control algorithm 2052, which when transmitted as an instruction for algorithm updating to the drug administration device 2002, can control the amount or timing of insulin that can be administered to a patient by the processor 2060 executing the algorithm 2052. In at least some embodiments, the control algorithm 2052 can be updated by adding at least one variable parameter thereto, for example when an appropriate medical professional may wish to control administration of the drug via a secondary parameter or control variable not previously accounted for in the algorithm 2052 but that the medical professional deems appropriate after review of sensed data received by the system 3002. In at least some embodiments, the control algorithm 2052 can be updated based on the processor 3060 completing a calibration routine or process for the drug administration device 2002. The calibration process can determine the accuracy of the device's sensors 2030, 2040 and the accuracy of the dosing delivered via the device 2002 to determine one or more calibration variables which can be among the at least one variable parameter of the control algorithm 2052.

In at least some embodiments, instead of being updated automatically by the system 3002 in response to analysis of data received from the device 2002, the control algorithm 2052 can be configured to be updated in response to a demand by a user associated with the drug administration device 2002, such as a patient using the device 2002 who can provide input thereto via the user interface 2080 or a medical professional providing treatment guidance to a patient who can provide input to the remote system 3002, such as at a medical facility such as the medical facility 706 of FIG. 7 or at a mobile location such as the mobile location 710 of FIG. 7. The user may not be aware of the algorithm 2052 at all or in detail and may thus not be particularly requesting a change to the algorithm 2052 but instead be more generally requesting a change in the device's drug delivery which in effect is a request for a change to the algorithm 2052. For example, the user can establish a communication link with the system 3002, e.g., via the device 2002 or a computer system in communication with the system 3002 such as a computer system at a medical facility such as the medical facility 706 of FIG. 7 or a computer system at a mobile location such as the mobile location 710 of FIG. 7, and request an update to the control algorithm 2052 based on a side-effect or clinical outcome the patient is experiencing as indicated by sensor 2030, 2040 data transmitted to the system 3002 and/or by input to the device 2002 via the user interface 2080 and transmitted to the system 3002.

The system 3002 can be configured to automatically update the algorithm 2052 in response to the request by analyzing data received from the device 2002 and adjusting the algorithm 2052 accordingly. Alternately, the system 3002 can be configured to present to the user one or more alternate control algorithm configurations, e.g., one or more sets of different variable parameter settings for the algorithm 2052, to be transmitted to and stored at the device 2002, e.g., in the memory 2050. The selections of alternate control algorithms made available to the user can be determined by the system's processor 3060 based on the sensed information received by the system 3002 and/or based on clinical outcomes reported by the patient. The system 3002 can be configured to allow the user to select one of the presented alternate algorithm configurations, e.g., via the user interface 2080 of the device 2002 or a user interface of the computer system which the user is using to interact with the system 3002, and to transmit the variable parameter settings for the selected algorithm to the device 2002 for the device 2002 to accordingly update the algorithm 2052. In other embodiments, the system 3002 can be configured to allow the user as a medical professional to change the algorithm 2052 based on the medical professional's analysis of data received by the system 3002 from the device 2002, which may allow for a more nuanced algorithm 2052 than alternate algorithms provided by the system 3002 for user selection.

In at least some embodiments, the system 3002 can be configured to mass or bulk update an algorithm stored at each of a plurality of drug administration devices. A mass or bulk update may be desirable, for example, when a new version of device firmware or operating systems have been made available by the manufacturer of the devices. In such a case each of the algorithms that the system 3002 causes to be updated are associated with a related drug administration device, such as each of the devices being of a same model, being in a same manufacturing lot, etc. For another example, a medical professional may desire to initiate a bulk update of the control algorithm on multiple drug administration devices each associated with a patient in a group of patients with a similar diagnosis or for patients experiencing a common side effect. For example, U.S. Patent Pub. No. 2002/0077852 entitled "Infusion Pump With An Electronically Loadable Drug Library And A User Interface For Loading The Library" published Jun. 20, 2002, which is hereby incorporated by reference in its entirety, describes various embodiments of drug delivery parameters and protocols for different drugs deliverable by infusion pumps.

In at least some implementations, the drug administration device 2002 can be configured to autonomously update the control algorithm 2052 without explicit user instructions or without a request from the system 3002 to update the control algorithm 2052. The drug administration device 2002 can be configured to check for control algorithm updates in regard to any one or more of a particular algorithm setting, variable parameter, security update, or the like. The drug administration device 2052 can be configured to continuously seek open communication channels via a wireless network in order to connect with the system 3002 and request that the system 3002 determine the availability of control algorithm updates and, if an update to the device's algorithm 2052 is determined to be available, for the update to be transmitted to the device 2002 so the algorithm 2052 can be changed in accordance with the update. Such a configuration may eliminate the system 3002 sending update requests to devices that are currently unavailable for updating, e.g., due to the device being turned off as no longer being in use by a patient, the device being out of network communication range, etc. Alternatively, upon establishing the communications channel, the drug administration device 2002, e.g., the processor 2060 thereof, can be configured to receive the most recent, available version of the control algorithm from the system 3002 and compare the version received from the system 3002 with the currently installed version of the algorithm 2052 stored in the device's memory 2050 to determine if an update is required and, if so, to update the stored algorithm 2052, e.g., by replacing the algorithm 2052 with the most recent, available version.

Once the drug administration device 2002 is aware that an update of the control algorithm 2052 is available, either due to the device 2002 continuously seeking a channel to check for algorithm updates or the device 2002 periodically pinging the system 3002 with a request for algorithm updates according to a predetermined schedule, the device 2002 can be configured to generate a notification to a user associated with the device 2002, e.g., the patient or a medical professional associated with the patient, identifying further input which is required to install the control algorithm update. The notification can be provided in any number of ways, such as an audio and/or visual alert via the device's user interface 2080, via the system's user interface 3080, or via other computer system accessible to the user such as via an app installed on the user's mobile device.

The control algorithm update can be a mandatory update required by the device manufacturer or by a medical professional in regard to a particular group of patients, such as updates to the variable parameters associated with drug delivery timing or dosage amounts. Alternatively, the control algorithm update can be an optional update that may or may not be applicable based on the configuration, model, and usage of the particular drug administration device 2002. Whether mandatory or optional, the update can be of one or more variable parameters of the algorithm 2052, can be the entire algorithm 2052, or can be a partial portion of the algorithm 2052 such as by adding one or more new variable parameters, removing one or more existing variable parameters, or changing the coefficient of one or more variable parameters. The mandatory and optional control algorithm updates can include algorithm updates that are customized for a specific patient by an appropriate medical professional. Additionally, or alternatively, the available control algorithm updates can be determined based on compiling an ensemble of different data by the system 3002. The ensemble of data can be processed to determine an updated control algorithm providing a greater degree of safety, patient compliance, and/or more accurate sensing or dosing controls which can lead to an improved clinical outcome or patient response.

The device 2002 and at least one additional drug administration device associated with the same patient can each be configured to transmit data to the system 3002. In such a case the system 3002 can be configured to aggregate and compile data from multiple devices, e.g., data sensed by each of the devices and/or data input by a user to each of the devices, to provide insights about patient's drug delivery timing and drug dosage over time. The aggregated data can be correlated with clinical outcomes or self-reported conditions experienced by the patient after administering the drug over time and can allow a medical professional to alter or modify the control algorithm 2052 of the device 2002 (and/or a control algorithm of any of the other devices associated with the patient) based on the time-based responses and trends observed for the patient. Embodiments of multiple interconnected computing devices associated with a drug administration system are further described in U.S. Patent Pub. No. 2014/0243635 entitled "Device For Enabling Patient Self Testing And Treatment Self-Administration And System Using The Device For Managing The Patient's Health Care" published Aug. 28, 2014 and U.S. Patent Pub. No. 2016/0045674 entitled "Supplemental Device for Attachment to an Injection Device" published Feb. 18, 2016, which are each incorporated by reference herein in their entirety.

In at least some implementations, the system 3002 can be configured to aggregate the data received from the device 2002 to provide a display of the drug dosage and clinical outcomes over time as graphical plots, such as on the device's user interface 2080 and/or on the system's user interface 3080. The response plot(s) can display, for example, a particular control variable of the algorithm 2052 that is being tracked, such as sensed data associated with a patient's blood sugar level. The sensed data can be displayed in conjunction with the drug administration data and any lifestyle or health events reported by the patient which can include eating, sleeping, activity levels, or the like. An appropriate medical professional can evaluate the response plot(s) and determine whether any adjustments to the control algorithm 2052 should be made and, if so, cause the system 3002 to push an algorithm update request to the device 2002, such as by the medical professional providing an input to the system 3002 via the user interface 3080.

In at least some implementations, the device 2002, e.g., the processor 2060 thereof, can be configured to perform analysis of the gathered information prior to or instead of the system 3002, e.g., the processor 3060 thereof, performing such an analysis as discussed above. Sharing analysis duties between the system 3002 and the device 2002 may be particularly beneficial for any number of reasons. For example, when the device 2002 is configured to continuously gather information with at least one of its sensors 2030, 2040 continuous gathering of data can yield a relatively large amount of data that may be more easily processed by multiple processors 2060, 3060. For another example, the device 2002 locally processing data indicative of the sensed information may be able to identify and cause a needed algorithm 2052 change before the system 3002 would have been able to receive data indicative of the sensed information and then identify and cause the change based on analysis of the received data. For yet another example, the system 3002 may be receiving data from numerous different drug administration devices in addition to data from the drug administration device 2002 such that data analysis for different devices must be queued and processed for one device at a time. The device 2002 locally processing at least some of the sensed information may thus reduce time lag in algorithm 2052 adjustment by allowing the sensed information to be analyzed more quickly than if the data had to wait in a queue for analysis at the system 3002. For another example, distributed processing may reduce execution time and memory consumption and/or may achieve better load balancing of data that is exchanged between the drug administration device 2002 and the system 3002. As a result, the drug administration device 2002 may receive updates to the control algorithm 2052 more quickly and with less latency compared to drug administration devices or systems which do not support distributed processing. Similarly, in at least some embodiments in which the system 3002 is fully responsible for data analysis or in which the device 2002 and system 3002 share data analysis responsibilities, distributed processing can be shared between the system 3002 and at least one other computer system, such as one or more computing devices located at the medical facility 706 of FIG. 7, at the home base 708 of FIG. 7, and at the mobile location 710 of FIG. 7.

The data that the device 2002 is configured to locally process for purposes of determining whether a change to the algorithm 2052 can vary. For example, the device 2002 can be configured to analyze data gathered by one of its sensors 2030, 2040 and to transmit data gathered by its other ones of the sensors 2030, 2040 to the system 3002 for analysis. For another example, the device 2002 can be configured to analyze data gathered within a first period of time, such as during typical sleep hours, and to transmit data gathered within a second, different time period, such as during typical awake hours when more sensed data may be gathered, to the system 3002 for analysis. For yet another example, the device 2002 can be configured to offload data processing on an as-needed basis, such as when the device 2002 is performing continuous monitoring or similar un-interruptible sensing operations. A patient may request a summarization and/or display of drug delivery data on the drug administration device 2002, such as by providing an input via the interface 2080, while the device 2002 is attempting to continuously monitor sensed information and simultaneously perform a complex drug delivery regimen requiring the control algorithm 2052 to be executed frequently over a short period of time. The drug administration device 2002 can thus be configured to determine ownership for certain high-priority execution tasks while off-loading or otherwise distributing low-priority execution tasks to the system 3002. In this way, the higher priority execution tasks can proceed without overloading the processor 2060 of the drug administration device 2002.

Figure 13:
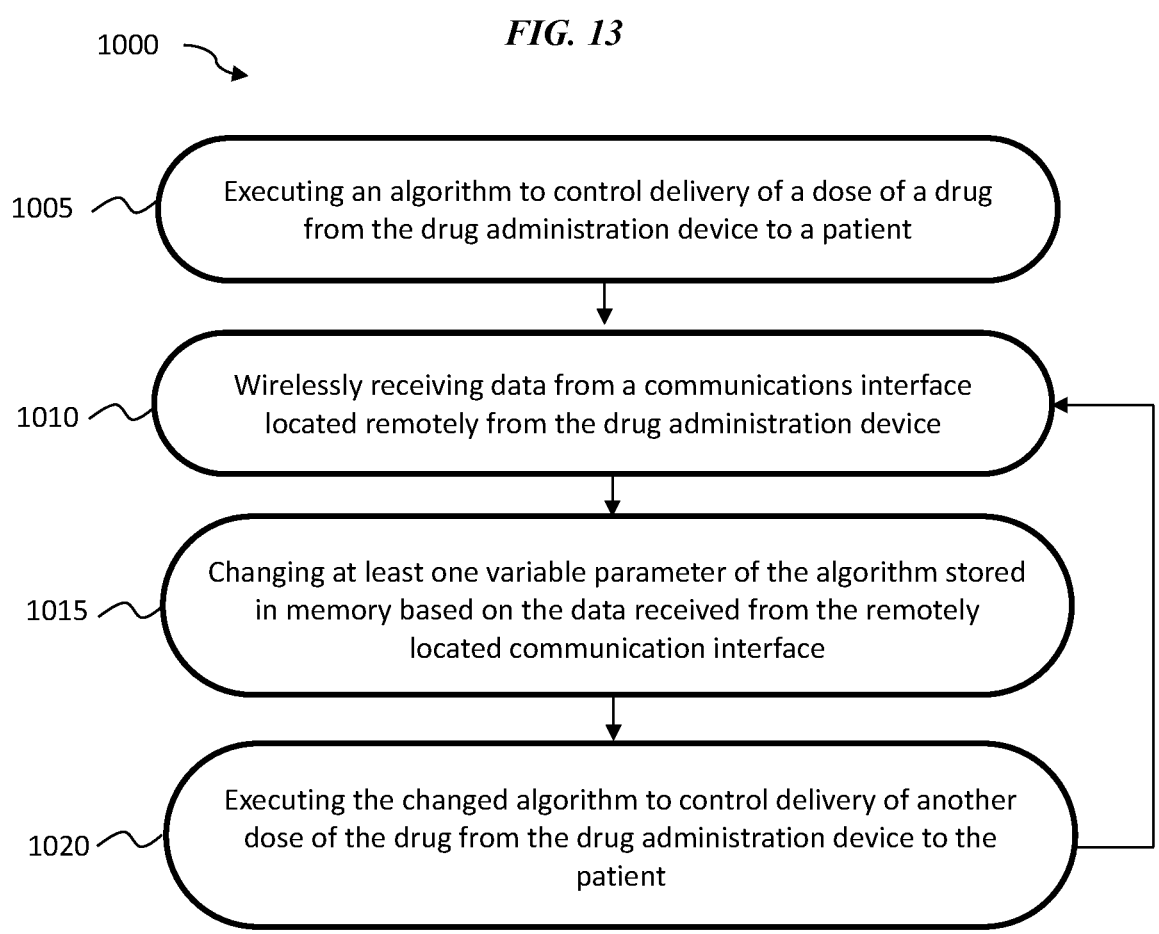
FIG. 13 is a flowchart illustrating one embodiment of a method for administering a drug using a control algorithm.

FIG. 13 is a flow diagram illustrating an exemplary embodiment of a method 1000 for administering a drug using an algorithm. The method 1000 is described with respect to the drug administration device 2002 and system 3002 of FIG. 12 for ease of explanation, but other devices and systems can be similarly implemented as discussed above.

In operation 1005, the drug administration device 2002 executes the algorithm 2052 to control delivery of a dose of a drug from the device 2002 to a patient, e.g., to cause the dispensing mechanism 2020 to release the drug from the drug holder 2010 and to the patient. In operation 1010, the drug administration device 2002 wirelessly receives data from the system 3002 that is located remotely from the device 2002 that includes an instruction to update the algorithm 2052. As discussed above, the system's transmission of the instruction can be triggered by analysis of data received from the device 2002 indicative of information gathered by one or more of the device's sensors 2030, 2040 and/or information otherwise received from the device 2002 such as information input to the device 2002 via the user interface 2080. As also discussed above, the system's transmission of the instruction can be triggered by a medical professional's input of an instruction or request into a computer system in communication with the system 3002, such as via a drug administration app configured on a mobile device at the mobile location 710 of FIG. 7, via a computing device at the medical facility 706 of FIG. 7, etc. The device 2002 can execute the algorithm 2052 a plurality of times to deliver a plurality of doses prior to the device 2002 receiving the instruction in operation 1010 to change the algorithm 2052.

In operation 1015, the drug administration device 2002 changes at least one variable parameter of the algorithm 2052 stored in the memory 2050 based on the data received from the remotely located communication interface in operation 1010. In operation 1020, the drug administration device 2002 executes the modified control algorithm 2052 to control delivery of a dose of a drug from the drug administration device 2002. The device 2002 can execute the modified algorithm 2052 a plurality of times to deliver a plurality of doses prior to the device 2002 receiving another instruction in operation 1010 to again change the algorithm 2052.

In at least some implementations, information indicative of at least some of the data communicated in a secure and anonymized manner from a device, such as any of the drug administration devices of FIGS. 1-5B, any of the drug housings 30, 630 of FIGS. 5B and 6, the packaging 35 of FIG. 5B, etc., to a remote computer system, such as central computer system 700 of FIG. 7, can be provided via visual and/or audio information via the device's user interface. As discussed above, this data can include data sensed by the device's sensor(s). The patient using the device may thus be kept informed of information gathered by the sensor(s).

In at least some implementations, information indicative of at least some of the data received at a device, such as any of the drug administration devices of FIGS. 1-5B, any of the drug housings 30, 630 of FIGS. 5B and 6, the packaging 35 of FIG. 5B, etc., from a remote computer system, such as central computer system 700 of FIG. 7, can be provided via visual and/or audio information via the device's user interface. The patient using the device may thus be kept informed of adjustments made, in response to the data received from the remote computer system, to an algorithm executable on board the device, e.g., by a processor thereof, to administer a dose of a drug to a patient.

In at least some implementations, information related to a patient's drug administration device can be provided to a user, e.g., the patient or a medical professional associated with the patient, via a user interface. In an exemplary embodiment the information is feedback and/or notifications (also referred to as "alerts") with respect to a patient's drug administration, treatment compliance, current medical conditions, and/or configuration of the patient's drug administration device. The feedback and notifications are configured to facilitate proper care of the patient by allowing any discrepancies in drug delivery to be quickly noticed and remedied, if needed, such as if drug delivery did not occur on schedule, and/or to provide reassurance and positive reinforcement to the user by indicating that drug delivery occurred as scheduled. A medical professional may receive data regarding a plurality of patients and thereby monitor drug dosage and drug delivery data associated with patients using the same or different drug administration devices or housings.

In an exemplary embodiment the feedback and/or notifications are provided via a drug administration app or program on a mobile computing device at a mobile location, such as the mobile location 710 of FIG. 7, configured to interoperate with at least one instructing device, such as a central computer system, e.g., the system 700 of FIG. 7, and/or a drug administration device and/or housing, e.g., the drug administration device 500 of FIG. 5B and/or housing 630 of FIG. 6. The drug administration app is configured to receive an instruction to provide a notification from the instructing device.

In at least some embodiments, the drug administration app can be integrated with the health tracking app or similar activity tracking program implemented on the mobile device by the manufacturer of the mobile device. To avoid sharing private or personal data stored in the health tracking app on the mobile device, the drug administration app can be configured to strip personal and private data that may be stored in the health tracking app when the drug administration app is operating to transmit data elsewhere, such as to the instructing device. Similarly, when data is received by the mobile device, the drug administration app can be configured to remove hierarchical condition categories, or other medical coding data, from the data. In at least some embodiments, the drug administration app can be configured to import health or activity data from other health tracking applications which may be installed on the mobile device. In at least some embodiments, the drug administration app can include a dashboard integrating the user's health and activity data with drug administration data, and/or related medical information which may be available from elsewhere, e.g., the drug administration device 500, housing 630, and/or system 700. As a result, the user can view and interact with a consolidated display of health status data and disease management data.

Integrating the drug administration app with the health tracking data and application configured on the mobile device may enable analysis of trends in a patient's medical condition. The drug administration app can be configured to provide lifestyle management advice based on the determined trends and corresponding changes in a patient's medical conditions as sensed or determined by the drug administration device, the housing, and/or the system. In at least some embodiments, the drug administration app can be configured to perform a cost analysis associated with a patient's treatment and determine predicted costs which may be incurred in the future. The drug administration app can be configured to enable a user to access to their personal medical records, schedule medical appointments, and access their patient billing, insurance, and payment information. When used by an appropriate medical professional, the drug administration app may enable faster on-boarding of new medical professionals by providing training on new treatments, medications, or alternate therapies. In these embodiments, the drug administration application can be configured to identify a patient's activity conflicts and adverse reactions to medications and can be configured to propose new or alternate treatments for a patient. Further description of various notifications and provision thereof is provided in U.S. Patent Pub. No. 2014/0081659 entitled "Systems And Methods For Surgical And Interventional Planning, Support, Post-operative Follow-up, And Functional Recovery Tracking" published Mar. 20, 2014, which is incorporated by reference herein in its entirety.

The drug administration app can be configured to provide interactive digital assistance for a medical professional in regard to drug administration data associated with a patient or group of patients. For example, the drug administration app can be configured to provide automated interactions and evaluations of a patient's mental or emotional state. Such interaction and evaluation may be useful to assess a patient's cognitive capability or level of cognitive impairment, as well as detect symptoms of depression, agitation, stress or anxiety. In at least some embodiments, the drug administration app can be configured to answer basic questions asked by a medical professional regarding medication instructions, drug interactions and/or side-effects. Further descriptions of interactive digital assistance that may be provided to medical professionals in regard to drug administration are provided in previously mentioned U.S. Patent Pub. No. 2014/0081659 entitled "Systems And Methods For Surgical And Interventional Planning, Support, Post-operative Follow-up, And Functional Recovery Tracking" published Mar. 20, 2014 and in U.S. Pat. No. 5,363,842 entitled "Intelligent Inhaler Providing Feedback To Both Patient And Medical Professional" issued Nov. 15, 1994, which is incorporated by reference herein in its entirety.

The drug administration app can be configured to provide interactive digital assistance by generating questions to be provided to a patient in regard to the patient's medical conditions and lifestyle management. The drug administration app can be configured to customize the generated questions with respect to a patient's overall wellness and/or the patient's current treatments. In at least some embodiments, the drug administration app can be configured to summarize a patient's physiological data, dosage data, dosage delivery schedule, and/or dosage compliance data so that a user may extract insights and apply or gather other supporting data or metadata. For example, based on processing the aggregated data sources, an algorithm can be applied to the data to determine maintenance or escalation procedures which may be required when a patient's physiological data is above a particular threshold value. Further descriptions of using data to extract or find out supporting data are provided in U.S. Patent Pub. No. 2005/0027791 entitled "Method Of Controlling Delivery Of A Service And Devices For Performing This Method" published Feb. 3, 2005, which is incorporated by reference herein in its entirety.

The digital assistance functionality configured within the drug administration app may provide a patient with better self-administration and self-management of disease prevention and wellness solutions. For example, the digital assistance functionality can be configured to recommend new treatment providers who are located in the patient's geographic area and who may specialize in the patient's particular disease or medical condition. In at least some embodiments, the digital assistance functionality can be configured to identify social networks or online communities that could provide support for the patient based on their needs and medical conditions. Other self-administration and self-management features of the interactive digital assistance functionality configured in the drug administration app 714 can include suggestions for alternate injection sites or drug delivery mechanisms based on self-reported medical condition data and sensed information gathered by sensor(s) of the drug administration device and/or housing. In at least some embodiments, the digital assistance functionality can be configured to generate recommendations for avoiding relapse of drug addiction based on behavioral data and sensed information collected from sensor(s) of the drug administration device and/or housing. Further descriptions of providing suggestions are described in previously mentioned U.S. Patent Pub. No. 2014/0081659 entitled "Systems And Methods For Surgical And Interventional Planning, Support, Post-operative Follow-up, And Functional Recovery Tracking" published Mar. 20, 2014 and in U.S. Patent Pub. No. 2017/0286610 entitled "Systems and Methods for Predicting Metabolic and Bariatric Surgery Outcomes" published Oct. 5, 2017, which is hereby incorporated by reference in its entirety.

In at least some embodiments, feedback/notifications can be provided to a user based on some aspect of data related to the patient's drug administration device exceeding a threshold or based on a rule. In at least some embodiments, feedback/notifications can be provided in a hierarchical manner based on the criticality of certain individual or combined data parameters. For example, when data associated with the operation of the patient's drug administration device, such as reduced needle penetration depth, is combined with a particular physiological condition sensed via at least one sensor of the drug administration device, such as elevated blood sugar levels, the drug administration device's user interface can be configured to notify the user of the drug administration device to take action to correct the malfunctioning device which may be causing elevated blood sugar levels. The feedback/notification can identify the corrective action, such as contacting the patient's medical professional or requesting an updated control algorithm for the drug administration device.

Notifications and feedback can be configured to be transmitted between devices associated with a computing system. In one embodiment, a drug administration app can exchange data with a drug administration device and/or a housing so that a user can configure notification settings of the drug administration device and/or the housing. In at least some embodiments, the drug administration app can be configured to enable a user to configure audible, visual, or tactile notifications.

In some embodiments, feedback/notifications provided to a user, e.g., via a user interface or an app, can include information regarding proper disposal of the drug administration device once drug delivery has been completed therefrom and the drug administration device is no longer needed or if drug delivery has not occurred and the drug delivery device is not empty of drug. Disposal of the drug administration device can be final discarding of the drug administration device (e.g., as medical waste garbage) or can be recycling of the drug administration device. The information regarding proper disposal of the drug administration device can thus be final discarding information or recycling information. Some drugs, such as esketamine, ketamine, and other controlled substances, may be required to be disposed of per a government requirement, e.g., U.S. federal Drug Enforcement Administration requirement, non-U.S. federal requirement, state requirement, or local requirement, to help, e.g., ensure that the drug is not accessed by an unauthorized party. Even if a drug administration device is used properly and delivers such a drug therefrom, disposal of the drug administration device may still be required, e.g., because a residual amount of the drug may be left in the drug administration device that could potentially be accessed by an unauthorized party or by the user after proper use of the drug administration device.

One example regarding proper disposal of the drug administration device is for the user to contact "X" provider to schedule a pick-up of the drug administration device, which can be provided with contact information provided for "X" provider. Another example regarding proper disposal of the drug administration device is for the user to ship the used drug administration devices to "Y" company, which can be provided with "Y" company's mailing address and/or with postage information provided.

In an exemplary embodiment, the information regarding proper disposal of the drug administration device is provided after all prescribed doses have been delivered from the drug administration device, although the information may be provided at other times. In some embodiments, the drug administration device, e.g., a processor thereof, is configured to locally determine that all prescribed doses have been delivered from the drug administration device. For example, the drug administration device can include a counter that counts a number of doses delivered from the drug administration device, and the processor can be configured to determine when the counter reaches a predetermined number corresponding to the number of prescribed doses. For another example, the drug administration device can include a counter that counts down one from the maximum number of prescribed doses each time a dose is delivered from the drug administration device, and the processor can be configured to determine when the counter reaches zero. In other embodiments, the drug administration device is configured to transmit drug delivery information to a remote computer system, such as central computer system 700 of FIG. 7, which is configured to determine that all prescribed doses have been delivered from the drug administration device in any of a variety ways, such as by the examples discussed above. In response to determining that all prescribed doses have been delivered from the drug administration device, the remote computer system can be configured to transmit a request to the device administration device to provide the information regarding proper disposal of the drug administration device.

The information regarding proper disposal of the drug administration device can be provided based on a geographic location of the user. Disposal requirements for medical waste can vary by jurisdiction (e.g., county, city, state, federal), so basing the information regarding proper disposal of the drug administration device on the geographic location of the user can help ensure that local jurisdiction rules are followed. The geographic location of the user can be known, for example, by the drug administration device including a geographic sensor or, for another example, by the user's mobile device including location sensing capability as will be appreciated by a person skilled in the art and the mobile device being configured to communicate with the drug administration device and/or the remote computer system.

The drug administration device and/or the remote computer system, which may include digital Instructions For Use (IFU), can be configured to access a disposal database that includes therein information correlating drug administration device disposal instructions with geographic locations, e.g., in a lookup table correlating each of a plurality of geographic locations with drug administration device disposal instructions specific to that geographic location. The disposal database can be maintained at the remote computer system and/or at another computer system, such as a computer system maintained by a manufacturer of the drug administration device and/or the drug delivered thereby.

In some embodiments, the disposal database also includes carbon footprint information regarding disposal of the drug administration device. Carbon footprint information can be correlated with each of the geographic locations, e.g., in a lookup table. The carbon footprint information can be provided with the drug administration device disposal instructions to help inform users of environmental factors associated with the drug administration device. Alternatively, the carbon footprint information can be calculated once the geographic location of a particular drug administration device is known based on the disposal requirements for that geographic location, e.g., based on the facility that will discard or recycle the drug administration device, and/or based on the geographic location itself, e.g., after a predetermined number of drug administration devices are disposed of from that geographic location the manufacturer of the drug administration device and/or the drug will take an action to reduce carbon footprint such as planting a tree, making a charitable donation, etc.

In some embodiments, instead of the drug administration device providing information regarding proper disposal of the drug administration device, a disposal container can be a smart container configured to contain a plurality of used drug administration devices therein and to provide information, e.g., on a user interface thereof, regarding proper disposal of the drug administration devices contained therein. The container can be configured to communicate data and show information similar to that discussed above regarding the drug administration device. The container being configured to provide information regarding proper disposal of the drug administration devices contained therein based on a geographic location of the container allows the same container to be used at any geographic location yet provide information specific to that geographic location. The containers may therefore be more efficiently manufactured since the containers need not be customized for particular geographic locations. In an exemplary embodiment, the container is configured to provide the information regarding proper disposal of the drug administration devices contained therein after a predetermined threshold number of drug administration devices have been disposed therein. The predetermined threshold number can vary based on the size of the container and the size of the drug administration devices disposed therein, but the predetermined threshold number generally corresponds to a number of drug administration devices that will fill or nearly fill the container. In some embodiments, sites (e.g., hospitals, medical clinics, or other medical care facilities) can be certified as a provider of a particular type of drug administration device and can receive the smart container after being so certified. Sites may need to be certified for certain types of drugs, such as esketamine, ketamine, or other controlled substances that have site certification as a REMS requirement, and hence be certified for drug administration devices that deliver those types of drugs.

In some embodiments, instead of the drug administration device or smart container providing information regarding proper drug administration device disposal, a shipping carton can be a smart carton configured to provide information, e.g., on a user interface thereof, regarding proper disposal of the drug administration devices shipped in the carton. The carton can be configured to communicate data and show information similar to that discussed above regarding the drug administration device. The carton being configured to provide information regarding proper disposal of the drug administration devices shipped therein based on a geographic location of the carton allows the same carton to be used at any geographic location yet provide information specific to that geographic location. The cartons may therefore be more efficiently manufactured since the cartons need not be customized for particular geographic locations.

In some embodiments, instead of the drug administration device, smart container, or smart carton providing information regarding proper drug administration device disposal, the drug administration device, smart container, or smart carton can have a label attached thereto (or otherwise part of the drug administration device, smart container, or smart carton) that is configured to be read electronically to provide information regarding proper drug administration device disposal for the drug administration device, drug administration devices in the smart container, or drug administration devices in the smart carton or smart container. The label can have a variety of configurations. For example, the label can include an integrated circuit configured to communicate the drug holder data from the drug holder. The label can be, for another example, a radio frequency identification (RFID) tag. For yet another example, the label can be in the form of a barcode. The label can be a single label or a plurality of labels. If a plurality of labels are used, each can be a different type from one another (e.g., one including a barcode and another including an RFID tag) from one another, which may help provide redundancy and/or allow for disposal information retrieval even if a certain type of data communication is currently unavailable, e.g., if an RFID scanner is absent or damaged. Various types of readers can be used to electronically read the label as appropriate for the label type, for example a bar code scanner, an RFID scanner, a mobile phone with barcode reading capability, etc. The reader can be configured to show thereon the read information regarding proper drug administration device disposal or the reader can be configured to communicate the read information to a computer system that shows the read information regarding proper drug administration device disposal.

Figure 14:
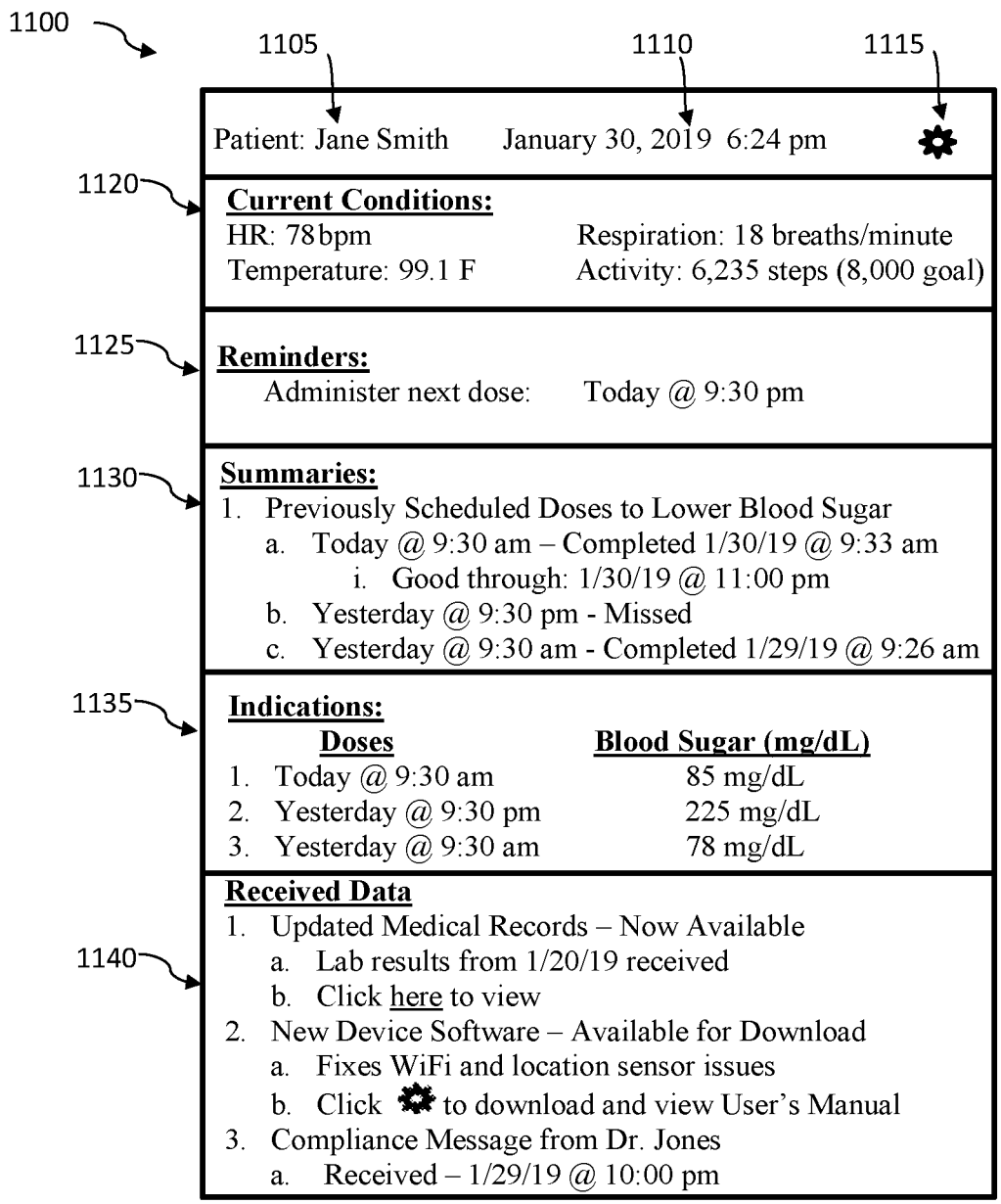
FIG. 14 is a schematic view of one embodiment of a user interface.

FIG. 14 illustrates one embodiment of a user interface 1100 displaying data, feedback, and notifications. In the exemplary embodiment illustrated in FIG. 14, the user interface 1100 is associated with a patient administering insulin via a drug administration device to lower the patient's blood sugar, but other types of drugs and other types of drug administration devices can be used as discussed herein.

The user interface 1100 includes a patient identifier 1105, a date/time identifier 1110, a configuration icon 1115, a current conditions portion 1120, a reminder portion 1125, a summary portion 1130, an indication portion 1135, and a received data portion 1140. In at least some embodiments, the layout and arrangement of the identifiers and portions within the user interface 1100 can be interactively rearranged by the user, as will be appreciated by a person skilled in the art. In this way, the user can create a customizable, dashboard-like, display of data that is organized to suit the user's preferences.

The patient identifier 1105 identifies the patient, "Jane Smith." The user interface 1100 is configured to display the user's name after the user has properly authenticated themselves to the respective device or system they are interacting with to help provide a secure system. A user can authenticate their identity in any number of ways, such as by using single-factor, two-factor, multi-factor, and/or strong authentication methods. A user can authenticate their identity using one or more authentication factors such as a password, pass phrases, a personal identification number (PIN), a challenge response, a security question, an ID card, a security token, a software or hardware token, a fingerprint, a retinal pattern, a signature, the user's face or voice, biometric identifiers, and the like.

The date/time identifier 1110 displays the current date and time. The current date and time may provide the user with temporal context about reminders, notifications, or other schedule based data, such as a reminder when to administer a next dose of a drug.

The configuration icon 1115 is an interactive graphical affordance or icon that, when selected or otherwise activated, causes the user interface 1100 to display additional functionality associated with the settings and configuration of the user interface. Selection/activation of the configuration identifier 1115 is configured to provide a user with tools to configure, not only the display of the user interface 1100, such as the arrangement or ordering of the identifiers and portions within the user interface, but also configurations of the device displaying the user interface 1100. In at least some embodiments, the configuration identifier 1115 is configured to show information indicative of help information regarding correct usage of the patient's drug administration device or housing for which the user interface 1100 is providing information. For example, the configuration identifier 1115 can include an additional graphical affordance or indicator, such as an icon, a symbol, or a number indicating to a user that an update is available to help the user correctly use the patient's drug administration device or housing for which the user interface 1100 is providing information. The indicated update can be associated with an updated version of the software that is available for download and installation on the patient's drug administration device or housing for which the user interface 1100 is providing information. The scope of permissible configuration changes provided by the configuration identifier 1115 can be adjusted as a preference within the system.

The current conditions portion 1120 of the user interface 1100 includes sensor data, e.g., information sensed by sensors, such as sensors 92, 94, 98 of the drug administration device 500 of FIG. 5B, sensors of a mobile device on which the user interface 1100 is shown, or other sensors. In this example, the current conditions portion 1120 displays the patient's heart rate (78 beats per minute), body temperature (99.1 degrees Fahrenheit), respiration rate (18 breaths per minute), and activity level (6,235 steps toward a goal of 8,000 steps per day).

The reminder portion 1125 provides reminders regarding one or more upcoming drug doses and/or regarding other aspects of the patient's treatment plan. In this example, the reminder portion 1125 provides a reminder to "Administer next dose: Today @ 9:30 pm." Thus, the user is being reminded that the next dose is to be administered in approximately three hours, as the current time is "6:24 pm." Other examples that can be provided in the reminder portion 1125 include reminders indicating a current need to manually administer a dose of the drug to the patient and reminders to change a battery of the patient's drug administration device, to charge the battery of the patient's drug administration device, to order a medication refill for the drug administration device, etc. In at least some embodiments, an audible, tactile, and/or visual notification can be provided in conjunction with a reminder appearing in the reminder portion 1125 to help encourage a user's notice of the newly provided reminder and/or provided at a time a reminded action is due to help encourage performance of the action at the proper time.

The summary portion 1130 provides a summary view of previously scheduled doses of the drug to the patient. As in this illustrated embodiment, the summary portion 1120 can also provide an indication of the intended treatment effect of the drug on the patient, as shown by "1. Previously Scheduled Doses to Lower Blood Sugar." As shown in FIG. 14, the summary portion 1130 includes a list of three previously scheduled doses, items a-c. As shown by item a, the summary portion 1130 indicates that the previously scheduled dose was administered "Today @9:30 am," and was successfully delivered ("Completed") on "1/30/19 @ 9:33 am." In this way, the summary portion 1130 provides the user with an intuitive presentation of the timing of the previously delivered doses compared to a predetermined delivery schedule for those doses. As shown by item a, sub-item i, the summary portion 1130 also provides the user with an indication of the estimated remaining duration of the drug's effect on a patient, "Good through: 1/30/19 @11:00 pm." Item c also shows information for a delivered dose ("Yesterday @ 9:30 am—Completed 1/29/19 @ 9:26 am"). The previously scheduled doses shown in the summary portion 1130 can also indicate when a patient missed a previously scheduled dose, shown as item b, "Yesterday @ 9:30 pm—Missed." The summary portion 1130 can be configured to allow scrolling to view additional summary information, e.g., doses scheduled for before "Yesterday @9:30 am." Other portions of the user interface 1100 can also be configured to allow scrolling for viewing of additional information.

In at least some embodiments, the summary portion 1130 can include other interactive graphical affordances, such as tabs or icons, which, when selected or activated, are configured to cause the summary portion 1130 to display dose delivery data over time in a graphical manner, such as a graph or chart. In at least some embodiments, the dose delivery data included in the summary portion 1130 can be provided in association with other clinical outcomes, sensed data events, and/or self-reported medical condition data provided by the patient. In at least some embodiments, the dose delivery data included in the summary portion 1130 can be provided in association with data received from the system 700 or from other data sources which may be accessible via the system 700 and network 702.

The indication portion 1135 provides a correlation between a timing of a previously delivered dose of the drug to the patient from the drug administration device or the housing and a timing of a medical event experienced by the patient. In this illustrated embodiment, the indication portion 1135 includes a list of the three most recent previously scheduled doses and one or more sensed characteristics of the patient, which in this illustrated embodiment includes the patient's blood sugar level measured at the time of each of the previously scheduled doses, e.g., measured by one of the drug administration device's sensors. When insulin was properly administered ("Completed" in the summary portion 1130) according to the previously scheduled times as shown by doses 1 and 3, the patient's blood sugar levels were kept within a normal range as shown by the measurement of 85 mg/dL corresponding to dose 1 completed "Today @9:30 am" and the measurement of 78 mg/dL corresponding to dose 3 completed "Yesterday @9:30 am." However, when the patient missed a dose, dose 2, "Yesterday @ 9:30 pm" ("Missed" in the summary portion 1130), the patient's blood sugar level was 225 mg/dL. The indication portion 1135 can be configured to correlate a timing of a previously delivered dose of a drug with a variety of medical events that may be experienced by the patient at the time of the previously delivered dose. In at least some embodiments, the medical event data may originate from the patient's medical records, and the indication portion 1135 can provide a correlation between the timing of previously delivered doses and medical record data, including for example clinical laboratory results.

The received data portion 1140 displays data that may be received from a remote location, such as the system 700 of FIG. 7 or a remote data source available through the system 700 via network 702. As shown in FIG. 14, the received data portion 1140 in this illustrated embodiment includes updated medical record information, "1. Updated Medical Records—Now Available." The updated medical record information can be received from a medical records database configured within the system 700 of FIG. 7 or a database associated with a computer system located at medical facility 706 of FIG. 7. In an exemplary embodiment, a user may view the updated medical records by clicking or otherwise selecting a uniform resource locator (URL) that the user interface 1100 has provided. In this illustrated example, clicking the word "here" as shown in "b. Click here to view" is configured to cause the user interface 1100 to provide the updated medical records for display. URLs may be used without limit within the user interface 1100 to provide additional data for display to the user.

As also shown in the received data portion 1140, a user may receive data providing help information about the usage of the drug administration device and/or the housing. For example, the received data portion 1140 can provide an indication of the help information as update information, which in this illustrated embodiment is shown as "2. New Device Software—Available for Download." The help information can include new device configuration settings as well as product documentation, such as a user's manual associated with the patient's drug administration device or housing. A user may cause the help information to be transmitted to and installed on the drug administration device or the housing by clicking or otherwise selecting the configuration identifier 1115.

The received data portion 1140 can include data which may be received from a remote based on information sensed or determined by the patient's drug administration device 500 or housing. For example, the received data portion 1140 in this illustrated embodiment includes a received remote data as "3. Compliance Message from Dr. Jones." Based on the patient's drug administration device and/or housing sensor(s) sensing the elevated blood sugar level of 225 mg/dL, which occurred in relation to the drug dosage previously scheduled and not administered "Yesterday @ 9:30 pm," the drug administration device and/or housing can transmit the sensed blood sugar levels (in addition to the drug delivery and compliance data) for display on the user interface 1100 in the received data portion 1140. In this illustrated example, as a result of receiving the sensed blood sugar values (in addition to summary data indicating the missed dosage scheduled for "Yesterday @ 9:30 pm"), the system may notify the patient's medical professional to send a compliance message to the patient to remind the patient, e.g., via notification in the reminder portion 1125, of the appropriate guidance and drug administration schedule necessary to reduce the patient's elevated blood sugar levels. In this way, data that is sensed or otherwise determined by the patient's drug administration device or housing can be transmitted to a remote computer system, where upon receiving the sensed information, the remote computer system can be configured to generate and transmit data associated with the sensed information back to the drug administration device or housing to be provided to a user via the user interface 1100.

Additional descriptions of data and displays of data provided within a user interface, such as user interface 80 of a drug administration device 500 or housing 630 or user interface 2080 of drug administration device 2002, are provided in U.S. Patent Pub. No. 2002/0091454 entitled "Remotely Programmable Infusion System" published Jul. 11, 2002, and U.S. Patent Pub. No. 2008/0139907 entitled "Intelligent Personal Health Management Appliance For The Measurement And Monitoring Of Health Factors And Controlled Delivery Of Drugs" published Jun. 12, 2008, both of which are incorporated by reference herein in their entireties.

All of the devices and systems disclosed herein can be designed to be disposed of after a single use, or they can be designed to be used multiple times. In either case, however, the devices can be reconditioned for reuse after at least one use. Reconditioning can include any combination of the steps of disassembly of the devices, followed by cleaning or replacement of particular pieces, and subsequent reassembly. In particular, the devices can be disassembled, and any number of the particular pieces or parts of the device can be selectively replaced or removed in any combination. Upon cleaning and/or replacement of particular parts, the devices can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

It can be preferred that devices disclosed herein be sterilized before use. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 published Aug. 13, 2009 and entitled "System And Method Of Sterilizing An Implantable Medical Device." It is preferred that device, if implanted, is hermetically sealed. This can be done by any number of ways known to those skilled in the art.

The present disclosure has been described above by way of example only within the context of the overall disclosure provided herein. It will be appreciated that modifications within the spirit and scope of the claims may be made without departing from the overall scope of the present disclosure.

What is claimed is:

1. A drug administration device configured to retain a drug therein, comprising:
  a sensor configured to sense information relating to at least one of the drug administration device and the drug;
  a memory configured to store data therein, the stored data including a key and an algorithm including at least one variable parameter, wherein the key is established with a remotely located server, is unique to the drug administration device and the remotely located server, and uniquely identifies a patient associated with the drug administration device;
  a communications interface configured to wirelessly transmit data indicative of the sensed information to a remotely located communications interface without any identifying patient information and to wirelessly receive data from the remotely located communications interface; and
  a processor configured to use the key to anonymize the data indicative of the sensed information prior to the transmission of the data indicative of the sensed information such that the data does not include any identifying patient information, use the key in decrypting the data received from the remotely located communications interface, use the algorithm in controlling delivery of the drug from the drug administration device to a patient, and to change the at least one variable parameter of the algorithm stored in the memory based on the data received from the remotely located communications interface.

2. The device of claim 1, wherein the drug administration device is one of a syringe, an injector, an inhaler, a nasal spray device, and an infusion pump.

3. The device of claim 1, wherein the processor is configured to use the key in anonymizing all data transmitted from the communications interface to the remotely located communications interface.

4. The device of claim 1, wherein the processor is configured to repeatedly use the key to anonymize multiple sets of data indicative of information sensed by the sensor.

5. The device of claim 1, wherein the communications interface is configured to wirelessly receive data from the remotely located communications interface.

6. The device of claim 5, wherein the processor is configured to use the key in decrypting all data received from the remotely located communications interface.

7. The device of claim 1, wherein the communications interface is configured to wirelessly receive data from the remotely located communications interface, the data includes information regarding proper disposal of the drug administration device after the drug has been delivered from the drug administration device.

8. The device of claim 7, wherein the processor is configured to cause a notification of the information regarding proper disposal information to be provided to a user of the drug administration device.

9. The device of claim 1, further comprising a label including information regarding proper disposal of the drug administration device after the drug has been delivered from the drug administration device.

10. The device of claim 1, wherein the processor is configured to control delivery of the drug from the drug administration device based at least in part on the sensed information.

11. The device of claim 1, wherein the drug comprises at least one of infliximab, golimumab, ustekinumab, daratumumab, guselkumab, epoetin alfa, risperidone, esketamine, ketamine, and paliperidone palmitate.

12. A drug administration system, comprising:
a server including:
  a communications interface configured to wirelessly receive data and wirelessly transmit data,
  a memory configured to store a key therein and an algorithm including at least one variable parameter therein, wherein the key uniquely identifies the drug administration device and a patient associated with the drug administration device, and
  a processor; and
a drug administration device including:
  a memory configured to store the key therein, the key being unique to the drug administration device and the server,
  a communications interface configured to wirelessly transmit data to the communications interface of the server without any identifying patient information and to wirelessly receive data from the communications interface of the server, and
  a processor;
wherein the processor of the server is configured to use the key to anonymize all data transmitted to the communications interface of the drug administration device prior to the transmission thereof; and
wherein the processor of the drug administration device is configured to use the key to anonymize all data transmitted to the communications interface of the server prior to the transmission thereof such that the data does not include any identifying patient information, to use the key in decrypting the data received from the remotely located communications interface, to use the algorithm in controlling delivery of a drug from the drug administration device to a patient, and to change the at least one variable parameter of the algorithm stored in the memory based on the data received from the remotely located communications interface.

13. The system of claim 12, wherein the drug administration device is one of a syringe, an injector, an inhaler, a nasal spray device, and an infusion pump.

14. The system of claim 12, wherein the processor of the server is configured to use the key to decrypt all data received from the communications interface of the drug administration device; and
wherein the processor of the drug administration device is configured to use the key to decrypt all data received from the communications interface of the server.

15. The system of claim 12, wherein the processor of the server is configured to automatically cause the data received from the communications interface of the drug administration device to be uploaded into at least one of an Electronic Health Record (EHR) of a patient associated with the drug administration device and a patient monitoring form for the drug's Risk Evaluation and Mitigation Strategies (REMS).

16. The system of claim 12, wherein the drug administration device also includes a sensor configured to sense information relating to at least one of the drug administration device and the drug, and the data transmitted to the communications interface of the server includes data indicative of the sensed information.

17. The system of claim 16, wherein the processor of the drug administration device is configured to control delivery of the drug from the drug administration device to a patient based at least in part on the sensed information.

18. The system of claim 12, wherein the data transmitted to communications interface of the server includes data in response to a data request received from the server.

19. The system of claim 12, wherein the drug comprises at least one of infliximab, golimumab, ustekinumab, daratumumab, guselkumab, epoetin alfa, risperidone, esketamine, ketamine, and paliperidone palmitate.

20. A drug administration method, comprising:
establishing a unique key for wireless communications between a drug administration device and a server located remotely from the drug administration device, the key being stored in a memory of the drug administration device and in a memory of the server, wherein the key uniquely identifies the drug administration device and a patient associated with the drug administration device;
sensing, with a sensor of the drug administration device, information relating to at least one of the drug administration device and a drug;
anonymizing, with a processor of the drug administration device, data indicative of the sensed information using the key stored in the memory of the drug administration device such that the data does not include any identifying patient information; and
using the key stored in the memory of the drug administration device in decrypting, with the processor of the drug administration device, data received from the server;

using an algorithm stored in the memory of the drug administration device to control delivery of a drug from the drug administration device to the patient; and changing at least one variable parameter of the algorithm stored in the memory based on the data received from the remotely located communications interface.

21. The method of claim 20, wherein the drug administration device is one of a syringe, an injector, an inhaler, a nasal spray device, and an infusion pump.

22. The method of claim 20, further comprising, controlling, with the processor of the drug administration device, delivery of the drug from the drug administration device based at least in part on the sensed information.

23. The method of claim 20, wherein the data includes information regarding proper disposal of the drug delivery device after the drug has been delivered from the drug delivery device.

24. The method of claim 23, further comprising causing, using the processor, a notification of the information regarding proper disposal information to be provided to a user of the drug administration device.

25. The method of claim 20, wherein the drug comprises at least one of infliximab, golimumab, ustekinumab, daratumumab, guselkumab, epoetin alfa, risperidone, esketamine, ketamine, and paliperidone palmitate.

* * * * *